(12) United States Patent
Whitman

(10) Patent No.: US 12,268,595 B2
(45) Date of Patent: *Apr. 8, 2025

(54) SYSTEMS AND METHODS FOR AFFIXING A PROSTHESIS TO TISSUE

(71) Applicant: MICRO INTERVENTIONAL DEVICES, INC., Newtown, PA (US)

(72) Inventor: Michael P. Whitman, Newtown, PA (US)

(73) Assignee: MICRO INTERVENTIONAL DEVICES, INC., Newtown, PA (US)

( * ) Notice: Subject to any disclaimer, the term of this patent is extended or adjusted under 35 U.S.C. 154(b) by 807 days.

This patent is subject to a terminal disclaimer.

(21) Appl. No.: 17/212,495

(22) Filed: Mar. 25, 2021

(65) Prior Publication Data

US 2021/0205082 A1    Jul. 8, 2021

Related U.S. Application Data

(63) Continuation of application No. 14/961,885, filed on Dec. 7, 2015, now Pat. No. 10,959,840, which is a
(Continued)

(51) Int. Cl.
*A61F 2/24*    (2006.01)
*A61B 17/068*    (2006.01)
*A61B 17/064*    (2006.01)

(52) U.S. Cl.
CPC .......... *A61F 2/2418* (2013.01); *A61B 17/068* (2013.01); *A61F 2/2409* (2013.01); *A61B 2017/0647* (2013.01); *A61F 2/2427* (2013.01)

(58) Field of Classification Search
CPC .... A61B 2017/0647; A61B 2017/0645; A61B 2017/0648; A61B 2017/0649; A61B 17/844; A61B 17/0401
See application file for complete search history.

(56) References Cited

U.S. PATENT DOCUMENTS 3,534,411 A    10/1970 Shiley
3,897,035 A    7/1975 Solo
(Continued)

FOREIGN PATENT DOCUMENTS

EP    0790038    8/1997
EP    1595504    11/2005
(Continued)

OTHER PUBLICATIONS

Second Office Action issued Oct. 19, 2020 in corresponding Chinese Patent Application 201680078175.1.
(Continued)

*Primary Examiner* — Ashley L Fishback
(74) *Attorney, Agent, or Firm* — DUANE MORRIS LLP

(57) ABSTRACT

Systems and methods recited herein provide for affixation of a prosthetic valve to surrounding tissue, by at least one anchor and an anchor deployment device. The surgical anchor includes a distal end tapered to a distal tip configured to pierce and anchor into tissue; a proximal head; and a tension component integrally connected with the distal end and the proximal head; wherein the tension component is configured to exert a force on the proximal head when the distal end is anchored into the tissue.

13 Claims, 47 Drawing Sheets

Related U.S. Application Data continuation-in-part of application No. 14/737,408, filed on Jun. 11, 2015, now abandoned.

(60) Provisional application No. 62/088,680, filed on Dec. 7, 2014, provisional application No. 62/010,680, filed on Jun. 11, 2014.

(56) References Cited

U.S. PATENT DOCUMENTS

| | | | |
|---|---|---|---|
| 3,959,960 A | 6/1976 | Santos | |
| 4,204,541 A | 5/1980 | Kapitanov | |
| 4,488,523 A | 12/1984 | Shichman | |
| 4,669,473 A | 6/1987 | Richard et al. | |
| 4,741,330 A | 5/1988 | Hayhurst | |
| 4,873,976 A | 10/1989 | Schreiber | |
| 4,884,572 A | 12/1989 | Bays et al. | |
| 4,968,315 A | 11/1990 | Gattuma | |
| 4,969,892 A | 11/1990 | Burton et al. | |
| 4,978,265 A | 12/1990 | De Wan | |
| 5,053,046 A | 10/1991 | Janese | |
| 5,059,206 A | 10/1991 | Winters | |
| 5,127,412 A | 7/1992 | Cosmetto et al. | |
| 5,356,424 A | 10/1994 | Buzerak et al. | |
| 5,370,661 A | 12/1994 | Branch | |
| 5,372,146 A | 12/1994 | Branch | |
| 5,478,353 A | 12/1995 | Yoon | |
| 5,505,735 A | 4/1996 | Li | |
| 5,562,704 A | 10/1996 | Tamminmaki et al. | |
| 5,569,264 A | 10/1996 | Tamminmaki et al. | |
| 5,584,859 A | 12/1996 | Brotz | |
| 5,601,557 A | 2/1997 | Hayhurst | |
| 5,694,782 A | 12/1997 | Alsenz | |
| 5,782,844 A | 7/1998 | Yoon et al. | |
| 5,782,861 A | 7/1998 | Cragg et al. | |
| 5,792,142 A | 8/1998 | Galitzer | |
| 5,814,051 A | 9/1998 | Wenstrom, Jr. | |
| 5,860,991 A | 1/1999 | Klein et al. | |
| 5,964,782 A | 10/1999 | Lafontaine et al. | |
| 5,976,127 A | 11/1999 | Lax | |
| 5,976,139 A | 11/1999 | Bramlet | |
| 5,993,475 A | 11/1999 | Lin et al. | |
| 6,010,525 A | 1/2000 | Bonutti et al. | |
| 6,027,523 A | 2/2000 | Schmieding | |
| 6,030,410 A | 2/2000 | Zurbrugg | |
| 6,120,525 A | 9/2000 | Westcott | |
| 6,159,234 A | 12/2000 | Bonutti et al. | |
| 6,174,323 B1 | 1/2001 | Biggs et al. | |
| 6,203,553 B1 | 3/2001 | Robertson et al. | |
| 6,206,895 B1 | 3/2001 | Levinson | |
| 6,221,092 B1 | 4/2001 | Koike et al. | |
| 6,231,561 B1 | 5/2001 | Frazier et al. | |
| 6,231,592 B1 | 5/2001 | Bonutti et al. | |
| 6,238,355 B1 | 5/2001 | Daum | |
| 6,331,182 B1 | 12/2001 | Tiefenbrun et al. | |
| 6,387,113 B1 | 5/2002 | Hawkins et al. | |
| 6,468,293 B2 | 10/2002 | Bonutti et al. | |
| 6,500,184 B1 | 12/2002 | Chan et al. | |
| 6,569,187 B1 | 5/2003 | Bonutti et al. | |
| 6,663,633 B1 | 12/2003 | Pierson, III | |
| 6,669,707 B1 | 12/2003 | Swanstrom et al. | |
| 6,692,499 B2 | 12/2004 | Tormala et al. | |
| 6,884,251 B2 | 4/2005 | Spence et al. | |
| 6,966,916 B2 | 11/2005 | Kumar | |
| 7,037,315 B2 | 5/2006 | Sancoff et al. | |
| 7,087,073 B2 | 8/2006 | Bonutti | |
| 7,104,949 B2 | 9/2006 | Anderson et al. | |
| 7,147,652 B2 | 12/2006 | Bonutti et al. | |
| 7,166,127 B2 | 1/2007 | Spence et al. | |
| 7,195,634 B2 | 3/2007 | Schmieding et al. | |
| 7,220,265 B2 | 5/2007 | Chanduszko et al. | |
| 7,235,090 B2 | 6/2007 | Buckman et al. | |
| 7,361,185 B2 | 4/2008 | O'Malley et al. | |
| 7,390,329 B2 | 6/2008 | Westra et al. | |
| 7,416,554 B2 | 8/2008 | Lam et al. | |
| 7,569,062 B1 | 8/2009 | Kuehn et al. | |
| 7,621,948 B2 | 11/2009 | Herrmann et al. | |
| 7,651,509 B2 | 1/2010 | Bojarski et al. | |
| 7,682,374 B2 | 3/2010 | Foerster et al. | |
| 7,736,378 B2 | 6/2010 | Maahs et al. | |
| 7,780,701 B1 | 8/2010 | Meridew et al. | |
| 7,780,702 B2 | 8/2010 | Shiono | |
| 7,833,238 B2 | 11/2010 | Nakao | |
| 7,850,712 B2 | 12/2010 | Conlon et al. | |
| 7,927,282 B2 | 4/2011 | Hettrick et al. | |
| 8,070,802 B2 | 12/2011 | Lamphere et al. | |
| 8,241,227 B2 | 8/2012 | Ohnishi et al. | |
| 8,337,525 B2 | 12/2012 | Stone et al. | |
| 8,361,113 B2 | 1/2013 | Stone et al. | |
| 8,366,766 B2 | 2/2013 | Berreklouw | |
| 8,382,776 B2 | 2/2013 | Ducharme | |
| 8,425,539 B2 * | 4/2013 | Binmoeller | A61B 1/041 606/155 |
| 8,500,760 B2 | 8/2013 | Mclawhorn | |
| 2001/0041916 A1 | 11/2001 | Bonutti | |
| 2003/0074021 A1 | 4/2003 | Morriss et al. | |
| 2003/0078604 A1 | 4/2003 | Walshe | |
| 2003/0078671 A1 | 4/2003 | Lesmiak et al. | |
| 2003/0092969 A1 | 5/2003 | O'Malley et al. | |
| 2003/0093117 A1 | 5/2003 | Saadat | |
| 2003/0097148 A1 | 5/2003 | Valimaa et al. | |
| 2004/0087981 A1 | 5/2004 | Berube et al. | |
| 2004/0092985 A1 | 5/2004 | Parihar et al. | |
| 2004/0138707 A1 | 7/2004 | Greenhalgh | |
| 2004/0147958 A1 | 7/2004 | Lam et al. | |
| 2004/0220596 A1 | 11/2004 | Frazier et al. | |
| 2004/0220610 A1 | 11/2004 | Kriedler et al. | |
| 2005/0021057 A1 | 1/2005 | St. Goar et al. | |
| 2005/0033398 A1 | 2/2005 | Seguin | |
| 2005/0038449 A1 | 2/2005 | Sancoff et al. | |
| 2005/0055027 A1 | 3/2005 | Yeung et al. | |
| 2005/0075654 A1 | 4/2005 | Kelleher | |
| 2005/0125011 A1 | 6/2005 | Spence et al. | |
| 2005/0143734 A1 | 6/2005 | Cachia et al. | |
| 2005/0177180 A1 | 8/2005 | Kaganov et al. | |
| 2005/0187568 A1 | 8/2005 | Klenk et al. | |
| 2005/0192599 A1 | 9/2005 | Demarais | |
| 2005/0216040 A1 | 9/2005 | Gertner et al. | |
| 2005/0222665 A1 | 10/2005 | Aranyi | |
| 2005/0228413 A1 | 10/2005 | Binmoeller et al. | |
| 2005/0234508 A1 | 10/2005 | Cummins et al. | |
| 2005/0251175 A1 | 11/2005 | Weisenburgh et al. | |
| 2005/0256532 A1 | 11/2005 | Nayak et al. | |
| 2005/0273138 A1 | 12/2005 | To et al. | |
| 2005/0283189 A1 | 12/2005 | Rosenblatt | |
| 2006/0004364 A1 | 1/2006 | Green et al. | |
| 2006/0030884 A1 | 2/2006 | Yeung et al. | |
| 2006/0030885 A1 | 2/2006 | Hyde | |
| 2006/0190042 A1 | 8/2006 | Stone et al. | |
| 2006/0207608 A1 | 9/2006 | Hirotsuka et al. | |
| 2006/0235413 A1 | 10/2006 | Denham et al. | |
| 2006/0247644 A1 | 11/2006 | Bhatnagar et al. | |
| 2006/0282008 A1 | 12/2006 | Ryan | |
| 2006/0282084 A1 | 12/2006 | Blier | |
| 2006/0282088 A1 | 12/2006 | Ryan | |
| 2006/0287661 A1 | 12/2006 | Bolduc et al. | |
| 2007/0016286 A1 | 1/2007 | Herrmann et al. | |
| 2007/0073320 A1 | 3/2007 | Mikkaichi et al. | |
| 2007/0083229 A1 | 4/2007 | Deutsch | |
| 2007/0112362 A1 | 5/2007 | Mikkaichi et al. | |
| 2007/0112425 A1 | 5/2007 | Schallet et al. | |
| 2007/0118213 A1 | 5/2007 | Loulmet | |
| 2007/0142837 A1 | 6/2007 | Dreyfuss | |
| 2007/0154515 A1 | 7/2007 | Johnson et al. | |
| 2007/0185530 A1 | 8/2007 | Chin-Chen et al. | |
| 2007/0203511 A1 | 8/2007 | Vardi | |
| 2008/0027477 A1 | 1/2008 | Obermiller et al. | |
| 2008/0051837 A1 | 2/2008 | To et al. | |
| 2008/0132948 A1 | 6/2008 | Surti et al. | |
| 2008/0161850 A1 | 7/2008 | Weisenburgh et al. | |
| 2008/0228030 A1 | 9/2008 | Godin | |
| 2008/0228193 A1 * | 9/2008 | Matityahu | A61M 37/0069 424/422 |

(56) References Cited

U.S. PATENT DOCUMENTS

| | | | |
|---|---|---|---|
| 2008/0294251 A1* | 11/2008 | Annest | A61B 17/00234 623/3.1 |
| 2008/0300547 A1 | 12/2008 | Bakos | |
| 2008/0300629 A1 | 12/2008 | Surti | |
| 2009/0005800 A1 | 1/2009 | Franer et al. | |
| 2009/0012560 A1 | 1/2009 | Hunter et al. | |
| 2009/0024163 A1 | 1/2009 | Zeiner et al. | |
| 2009/0082790 A1 | 3/2009 | Shad et al. | |
| 2009/0088780 A1 | 4/2009 | Shiono et al. | |
| 2009/0198107 A1 | 8/2009 | Park et al. | |
| 2009/0216264 A1 | 8/2009 | Friedman et al. | |
| 2009/0228040 A1 | 9/2009 | Mas et al. | |
| 2009/0236401 A1 | 9/2009 | Cole et al. | |
| 2009/0240264 A1 | 9/2009 | Tuval et al. | |
| 2009/0248067 A1 | 10/2009 | Maiorino | |
| 2009/0248071 A1 | 10/2009 | Saint et al. | |
| 2009/0275960 A1 | 11/2009 | Provenza et al. | |
| 2009/0287245 A1 | 11/2009 | Ostrovsky et al. | |
| 2009/0287304 A1 | 11/2009 | Dahlgren et al. | |
| 2010/0010457 A1 | 1/2010 | Ewers et al. | |
| 2010/0049213 A1 | 2/2010 | Serina et al. | |
| 2010/0049289 A1 | 2/2010 | Lund et al. | |
| 2010/0087854 A1 | 4/2010 | Stopek et al. | |
| 2010/0094341 A1 | 4/2010 | Raju | |
| 2010/0113873 A1 | 5/2010 | Suzuki et al. | |
| 2010/0016885 A1 | 10/2010 | Eidenschink et al. | |
| 2011/0028995 A1 | 2/2011 | Miraki et al. | |
| 2011/0054539 A1 | 3/2011 | Knopfle et al. | |
| 2011/0166649 A1 | 7/2011 | Gross et al. | |
| 2011/0178534 A1 | 7/2011 | Whitman et al. | |
| 2011/0178535 A1 | 7/2011 | Whitman | |
| 2011/0178537 A1 | 7/2011 | Whitman | |
| 2011/0190811 A1 | 8/2011 | Shanley | |
| 2011/0208290 A1 | 8/2011 | Straubinger | |
| 2011/0288583 A1 | 11/2011 | Goraltchouk et al. | |
| 2012/0022586 A1 | 1/2012 | Whitman et al. | |
| 2012/0059395 A1 | 3/2012 | Kehdy et al. | |
| 2012/0111338 A1 | 5/2012 | Weitraub | |
| 2012/0116418 A1 | 5/2012 | Belson et al. | |
| 2012/0179172 A1 | 7/2012 | Paul, Jr. et al. | |
| 2012/0245634 A1 | 9/2012 | Kaplan | |
| 2012/0296345 A1 | 11/2012 | Wack et al. | |
| 2012/0323317 A1 | 12/2012 | Karapetian et al. | |
| 2013/0046373 A1 | 2/2013 | Cartledge et al. | |
| 2013/0144378 A1 | 6/2013 | Quadri et al. | |
| 2013/0197578 A1 | 8/2013 | Gregoire et al. | |
| 2013/0211426 A1 | 8/2013 | Whitman et al. | |
| 2013/0211450 A1 | 8/2013 | Whitman | |
| 2013/0218267 A1 | 8/2013 | Braido et al. | |
| 2014/0039548 A1 | 2/2014 | Whitman et al. | |
| 2014/0039549 A1 | 2/2014 | Belsky et al. | |
| 2014/0236289 A1 | 8/2014 | Alkhatib | |
| 2015/0045781 A1 | 2/2015 | Abboud et al. | |
| 2015/0272737 A1 | 10/2015 | Dale | |
| 2016/0361161 A1 | 12/2016 | Braido | |

FOREIGN PATENT DOCUMENTS

| | | |
|---|---|---|
| EP | 1728474 | 12/2006 |
| WO | 93/14705 | 8/1993 |
| WO | 96/06565 | 3/1996 |
| WO | 96/39082 | 12/1996 |
| WO | 99/21490 | 5/1999 |
| WO | 00/40158 | 7/2000 |
| WO | 00/59383 | 10/2000 |
| WO | 01/85035 | 11/2001 |
| WO | 02/091928 | 11/2002 |
| WO | 03/059173 | 7/2003 |
| WO | 2005/004727 | 1/2005 |
| WO | 2005/018426 | 3/2005 |
| WO | 2005/058239 | 6/2005 |
| WO | 2005/112784 | 12/2005 |
| WO | 2005/115256 | 12/2005 |
| WO | 2007/051107 | 5/2007 |
| WO | 2007/075981 | 7/2007 |
| WO | 2007/098212 | 8/2007 |
| WO | 2008/045635 | 4/2008 |
| WO | 2008067384 | 6/2008 |
| WO | 2008/116203 | 9/2008 |
| WO | 2010/053708 | 5/2010 |
| WO | 2010-127873 | 11/2010 |
| WO | 2013/022798 | 2/2013 |

OTHER PUBLICATIONS

Communication pursuant to Rule 164(1) EPC dated Nov. 22, 2019 for European Application No. 16873687.4.

Partial Supplementary European Search Report, dated Feb. 20, 2018, issued in European Patent Application No. 15806837.9 (16 pages).

Extended European Search Report, dated Oct. 24, 2017, issued in European Patent Application No. 15806896.5 (8 pages).

Extended European Search Report, dated Oct. 30, 2017, issued in European Patent Application No. 17181453.6 (8 pages).

Extended European Search Report, dated Nov. 27, 2017, issued in European Patent Application No. 11735207.0 (9 pages).

Supplementary European Search Report, dated Aug. 1, 2017, issued in European Patent Application No. 11735203.9 (2 pages).

Supplementary European Search Report, dated Aug. 10, 2017, issued in European Patent Application No. 11735207.0 (2 pages).

International Search Report and Written Opinion of the International Searching Authority issued Apr. 21, 2017, in International Patent Application No. PCT/US2016/065196.

Extended European Search Report, dated Dec. 14, 2016, issued in European Patent Application No. 14763744.1.

Partial Supplementary European Search Report, dated Aug. 19, 2016, issued in European Patent Application No. 14763744.1 (9 pages).

International Search Report and Written Opinion, dated Nov. 23, 2015, in International Patent Application No. PCT/US2015/035191.

International Search Report and Written Opinion, dated Mar. 11, 2011, issued in corresponding International Application No. PCT/US2011/021946.

International Search Report and Written Opinion, dated Apr. 8, 2011, issued in corresponding International Application No. PCT/US2011/021952.

International Search Report and Written Opinion, dated Jun. 1, 2011, issued in corresponding International Application No. PCT/US2011/021949.

International Search Report and Written Opinion, dated Mar. 23, 2011, issued in corresponding International Application No. PCT/US2011/021947.

European Supplementary Search Report, dated Jun. 13, 2013, issued in corresponding European Patent Application No. 11735202.1.

International Search Report and Written Opinion, dated Sep. 8, 2014, issued in corresponding International Application No. PCT/US2014/30868.

Extended European Search Report issued in European Patent Application No. 11735204.7, dated Sep. 2, 2015.

International Search Report and Written Opinion issued in PCT/US2015/035427, dated Sep. 16, 2015.

* cited by examiner

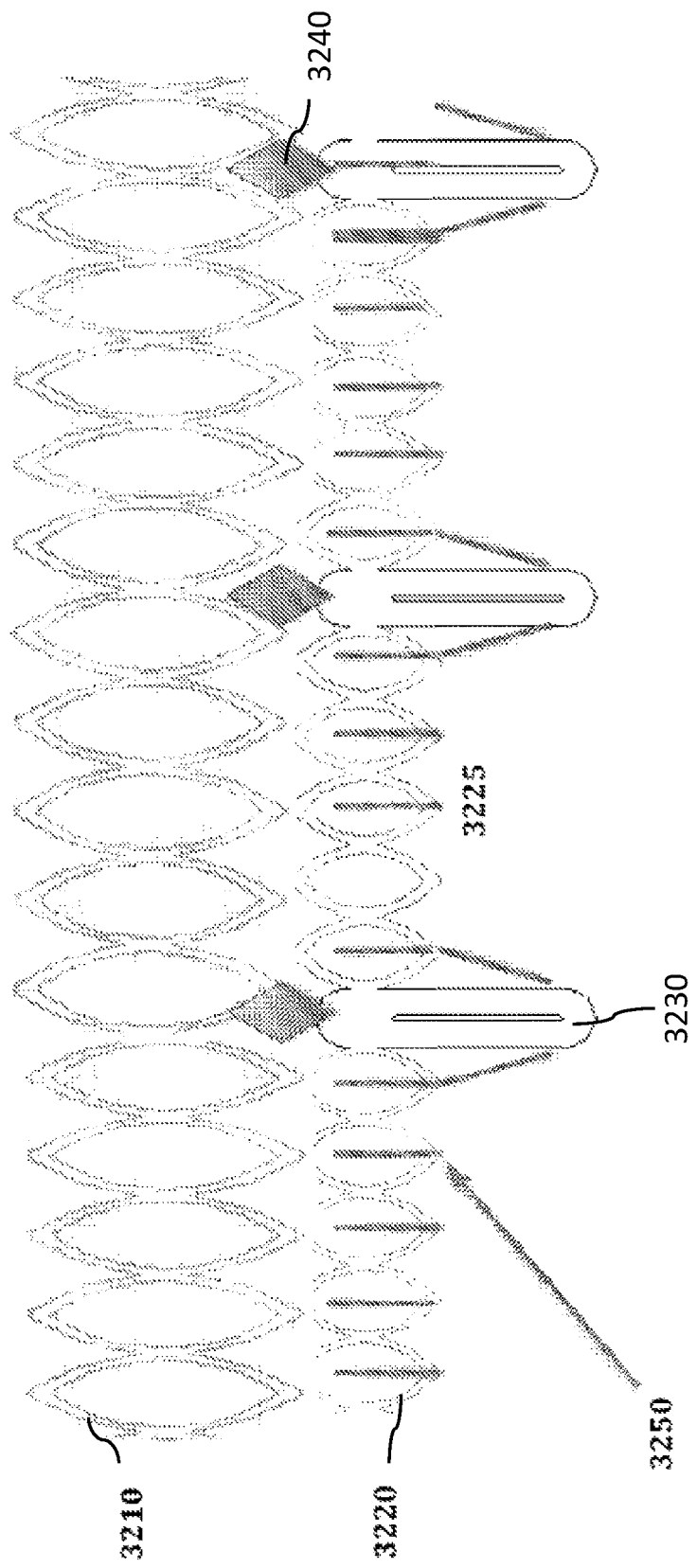

Valve 3205

3240

SYSTEMS AND METHODS FOR AFFIXING A PROSTHESIS TO TISSUE

CROSS-REFERENCE TO RELATED APPLICATIONS

This application is a continuation application of co-pending U.S. patent application Ser. No. 14/961,885, filed Dec. 7, 2015, which claims the benefit of U.S. Provisional Application Ser. No. 62/088,680, filed on Dec. 7, 2014, the entire contents of which are incorporated by reference herein.

The U.S. patent application Ser. No. 14/961,885 is also a continuation-in-part of U.S. patent application Ser. No. 14/737,408, filed Jun. 11, 2015, which claims the benefit of the filing date of U.S. Provisional Application Ser. No. 62/010,680, filed on Jun. 11, 2014, and which is also incorporated by reference herein in its entirety.

Further, each of the following is hereby incorporated by reference hereto in its entirety: U.S. patent application Ser. No. 14/321,476, filed Jul. 1, 2014, U.S. patent application Ser. No. 14/301,106, filed Jun. 10, 2014, U.S. patent application Ser. No. 13/843,930, filed Mar. 15, 2013, PCT Application No. PCT/US14/30868, filed Mar. 17, 2014, U.S. patent application Ser. No. 13/010,769, filed Jan. 20, 2011, U.S. Provisional Application Ser. No. 61/296,868, filed on Jan. 20, 2010, U.S. patent application Ser. No. 13/010,766, filed on Jan. 20, 2011, U.S. patent application Ser. No. 13/010,777, filed on Jan. 20, 2011, and U.S. patent application Ser. No. 13/010,774, filed on Jan. 20, 2011.

FIELD OF THE INVENTION

The present invention relates to an anchoring device and method, and systems and methods for affixing a prosthesis to tissue.

BACKGROUND INFORMATION

Heart valve replacements have been developed to counter heart valve failure, either from heart valve regurgitation (i.e., the failure of the heart valve to properly close), or from heart valve stenosis (i.e., the failure of the heart valve to properly open). Though early efforts at heart valve repair and replacement included open surgery, more recent developments have included percutaneous surgical applications.

Percutaneous heart valve repair, however, has shown certain disadvantages. For example, percutaneous repair involves modified surgical techniques, which can limit the benefits of the procedure. Annular rings may lack effectiveness, and include risks of erosion, perforation, and coronary artery thrombosis. Edge-to-edge repair can be technically demanding, and may lack long term durability. Depending upon the particular valve failure, combinations of different repair techniques may be necessary, further complicating the procedure and limiting its effectiveness.

In contrast, heart valve replacement has provided certain advantages, limiting the risks associated with heart valve repair, and applying to a broader scope of patients. Open surgery solutions for heart valve replacement, however, carry significant risks to the patient. Therefore, a less invasive, percutaneous heart valve replacement is needed.

Existing percutaneous solutions include U.S. Pat. No. 7,621,948, describing a percutaneously inserted heart valve prosthesis, which can be folded inside a catheter for delivery to the implant location. Another percutaneous solution is available from CardiAQ Valve Technologies, Inc., described in U.S. Patent Application Publication No. 2013/0144378. Other percutaneous prosthetic valves include Neovasc Tiara, Valtech Cardiovalve, ValveXchange, Lutter Valve, and valves from Medtronic, Inc. and Edwards Lifesciences Corporation.

In providing a percutaneous heart valve replacement, challenges include providing an implant that may be folded into a catheter for delivery, and can emerge from the catheter to fit properly into the implant site and serve its function as a valve. The implant valve must therefore be small enough to be folded into the catheter, but must be large enough, upon implantation, to provide the functions of the valve, without being so large as to obstruct ventricular flow.

Moreover, fixing the heart valve implant to the implant site may be challenging, as the implant site may form an irregular shape, may lack calcium to secure the valve, or may cause difficulty in fixing the implant valve with the proper orientation.

Further, although long-standing surgical methods for the implantation and the design of aortic valve prosthesis have proven both safe and reliable over the past few decades, it has been well documented that the transition of these same prosthetic designs and surgical methods, to mitral valve replacement, has fallen far short both in terms of safety and reliability.

The reason for this failure is simple: the aortic and mitral valves differ in a number of substantive ways. For example, in a body of operable patients the aortic valve will consist of more rigid, calcified tissue, whereas the mitral valve will be composed of muscular tissue that dilates and constricts, to some extent, throughout the cardiac cycle. This seemingly innocuous difference is one of several that have caused aortic prosthesis to fail in the mitral arena. That is, aortic prosthesis may rely on radial pressure to 'force fit' in a particular location. But, the mitral valve lacks the necessary rigidity and consistency of size that allow radial pressure to succeed as a means of engagement in the aortic arena.

The ineffectiveness of radial pressure to reliably secure a prosthesis in certain cardiac procedures has also had implications regarding the invasiveness of those procedures. For example, in the case of certain anchoring approaches and all suture dependent approaches, the need for tensioning the anchoring device or suture has generally required that a surgery be far more invasive than might be otherwise necessary. The reason for this is simple: a surgeon will require more direct access to the prosthesis in order to manually tension the anchors or sutures employed.

Another dilemma in prosthetic related cardiac surgeries results from the drastic structural variance between individual hearts when circumstances dictate that radial pressure will not serve as an adequate means of securement. The distance between the interior tissues surrounding the mitral valve and the coronary sinus, circumflex artery, or electrophysiological conduction system, for example, vary materially between patients. Furthermore, the depth required for a certain anchor or suture to reliably affix a prosthesis is often not present between the operable tissue and these fragile structures. The potential health risks created by this dilemma have not been sufficiently addressed by the current technologies in this space, and it is difficult to envision an anchoring technology that would maintain a deployment depth necessary to consistently secure a prosthesis without running the risk of damaging nearby cardiac features.

The aforementioned examples serve to highlight the inability of long standing aortic valve replacement technologies to be effectively employed in alternate surgical implications within the heart. The drawbacks associated with the heightened level of invasiveness and the implications of structural inconsistencies are two of many problems yet to be solved for the growing number of cardiac patients in the world today. All of these differences, though, can be overcome by means of a proprietary anchoring technology, capable of bridging the gap in structural discrepancy described above.

SUMMARY

The device and surgical methodology described below can be considered as having three main components: a deployment mechanism, an anchor and a prosthesis. Together, these three features can be used to reliably reach and secure the prosthetic valve to the soft tissues of the human heart, such that the prosthesis can address ailments such as heart valve insufficiency or stenosis. Per their unique designs, the low-profile deployment system ensures that the surgery is minimally invasive, while the TCAT (Transcatheter Anchoring Technology) anchors serve to overcome the aforementioned structural and functional difficulties of securing a prosthesis to locations such as the mitral valve.

Where radial pressure has proven a viable means of securement for aortic valve prosthesis, anchors will serve as the most efficient method of securement in mitral valve replacement. The design of the anchor addresses various problems associated with anchoring or suturing a prosthesis within the heart. First, the tension component serves a dual purpose in the anchor's design: it pulls the anchor head component in a proximal direction after deployment, allowing the barbs to set more securely, and also allows for the prosthesis to remain in more constant contact with the tissues of the heart, despite their fluctuating throughout the cardiac cycle. This means that where other anchoring technologies, or suturing methods, require tensioning in order to most effectively secure a prosthesis to the implant site, the anchor tensions itself. This allows for a procedure to be completed on a level of significantly less invasiveness to the patient, encouraging faster recovery times and minimizing detrimental outcomes.

Moreover, the proprietary design of the anchor, namely with regard to its tension component, may overcome a number of difficulties presented by valve replacement surgeries, particularly in the case of mitral valve replacement. That is, this design is better suited to encourage constant contact between a prosthesis and the tissues of the heart, particularly when those tissues expand and contract. The anchor design is also better suited to pull the tissues surrounding the mitral valve into apposition with the prosthesis, thereby reducing health risks associated with blood flowing around the exterior perimeter of the prosthesis. In other words, when the walls surrounding the mitral valve dilate during the cardiac cycle, the tension spring component can counter that outward force, so as to minimize gaps that would be created whilst minimizing potential damage to the soft tissues surrounding the anchors' barbs.

The anchors described below, in applying this tension component, provide active fixation to prosthetic valves. Previous anchor devices employing a threaded screw, for example, will not properly anchor into soft tissue. Active fixation of a prosthetic valve benefits from the proprietary design of the anchors described below, having a tensioning component that is integrally formed to the anchor, allowing for spontaneous tensioning force, without intervention, after the anchor is deployed into tissue.

Further described below is a compliant valve using active fixation (i.e., the anchor deployment) to affix the valve to the native heart tissue. The prosthetic valve described below may include varying rigidity, e.g., by varying the wall thickness of the frame making up the valve. The valve may be compliant on the inflow side, above a more rigid annular ring, and even more rigid leaflet posts or struts. If the valve is soft and malleable on its inflow side, when the prosthesis is applied to native tissue in a heart valve, the prosthesis may form its shape to the shape of the native tissue. The benefits of such a malleable valve include a better seal of the valve inflow track, which allows for improved tissue in-growth into the prosthetic. Further, the more rigid annular cells and leaflet posts allow for greater support at the outflow side of the valve, where the valve fatigue is greatest.

Accordingly, in accordance with example embodiments of the present invention, a system for fixing a prosthetic valve device to tissue is provided.

In an exemplary embodiment, a surgical anchor includes a distal end tapered to a distal tip configured to pierce and anchor into tissue, a distal end tapered to a distal tip configured to pierce and anchor into tissue, a proximal head, and a tension component integrally connected with the distal end and the proximal head, wherein the tension component is configured to exert a force on the proximal head when the distal end is anchored into the tissue.

The tension component may include an elastomer overmolded to the distal end and the proximal head. The tension component includes a spring. The anchor may be configured to engage with the tissue and resist proximal movement. The tension component may exert the force on the proximal head of the deployed anchor, urging the proximal head of the anchor in a proximal direction. The proximal head may include a non-deforming material.

In an exemplary embodiment, a surgical device includes an anchor, wherein the anchor includes, a distal end tapered to a distal tip configured to pierce and anchor tissue, a proximal head having a width greater than a width of a corresponding anchor receptacle of a prosthetic valve, and a tension component between the distal end and the proximal head, wherein the distal end of the anchor is configured to be driven by a deployment device through the corresponding anchor receptacle of the prosthetic valve into tissue adjacent to the prosthetic valve, and further wherein a proximal end of the proximal head of the deployed anchor is configured to be brought into apposition with the corresponding anchor receptacle, such that, after deployment of the anchor into tissue, the tension component is in a tensioned state to exert a pulling force on the proximal head of the anchor so that the proximal head acting on the anchor receptacle of the prosthetic valve will approximate the prosthetic valve with the tissue.

In an exemplary embodiment, a deployment device includes a retractable sheath covering a cavity for housing a prosthetic valve in a retracted state, a plurality of deployment arms, each arm including a cavity for housing a surgical anchor, a force delivery device, and a shaft connecting the force delivery device to the deployment arms, wherein each of the deployment arms is configured to rotate from a retracted position aligned with an axis of the deployment device to a deployed position directed radially away from the axis, and wherein the force delivery device is configured to exert a force through the shaft and the deployment arms to drive the surgical anchor into tissue from the cavity of the deployment arms.

The force delivery device may include at least one of the following: springs, expandable gas, and/or compressed fluid.

The force delivery system may include a canister housing an expanding gas and a solenoid configured to control the release of the expanding gas.

Each of the deployment arms may include a pin in communication with the force delivery device via the shaft, the pin configured to transfer the force from the force delivery device to a surgical anchor housed in the cavity of the deployment arm. The pin may be configured to drive the anchor into tissue. The prosthetic valve may be delivered to an implant site by the retractable sheath, the prosthetic valve device being folded for insertion into the retractable sheath and self-expandable after the retractable sheath retracts and exposes the prosthetic valve device.

The deployment device may include at least one prosthetic grip which holds the prosthetic valve device in place prior to and during anchor deployment. The prosthetic valve device may be delivered to an implant site by the retractable sheath, the prosthetic valve device being folded for insertion into the retractable sheath and expandable by the deployment arms after the retractable sheath retracts and exposes the prosthetic valve device. The prosthetic valve may be configured for release simultaneously with anchor deployment. One of a pulling and pushing driving force on the anchors may drive the anchors from the deployment arms.

In an exemplary embodiment, a prosthetic valve includes a plurality of anchor receptacles, a plurality of inflow cells situated in the proximal direction of the prosthetic valve, wherein the inflow cells are malleable, and a plurality of annular cells situated medially in the prosthetic valve, forming a circular outflow track, wherein the annular cells are more rigid than the inflow cells, and a plurality of leaflet posts integral to, and extending distally beyond, the annular cells in the outflow direction of the prosthetic valve, wherein the leaflet posts are more rigid than the annular cells.

The plurality of the inflow cells may extend radially in a distal direction. Each of the anchor receptacles may be configured to receive an anchor including a distal end tapered to a distal tip configured to pierce and anchor into tissue, a proximal head, and a tension component, situated between the distal end and the proximal head, wherein the anchor receptacles are large enough to permit the passage of the distal end of the anchor through the anchor receptacle and into surrounding tissue, and small enough to prevent the passage of the proximal head through the anchor receptacle, such that, after deployment of the anchor the tension component is situated in a tensioned state against the anchor receptacle and the tissue to bring the prosthetic valve into apposition with the tissue.

The prosthetic valve may further include valve leaflets connected between the leaflet posts, and a woven covering.

In an exemplary embodiment, a prosthetic valve includes a plurality of inflow cells situated in the proximal direction of the prosthetic valve, and a plurality of ring struts extending radially from the inflow cells, wherein the ring struts lay flat to the prosthetic valve when retracted, and form a ring around the inflow cells of the valve when deployed.

BRIEF DESCRIPTION OF THE DRAWINGS

FIG. 32A is an illustration of a frame for a prosthetic valve, in accordance with an example embodiment of the present invention.

DETAILED DESCRIPTION

As set forth in greater detail below, example embodiments of the present invention allow for the effective and reliable deployment of specially designed TCAT anchors, by means of a proprietary catheter-based delivery mechanism, for the purposes of securing a prosthesis to the tissues of the human heart.

Figure 1:
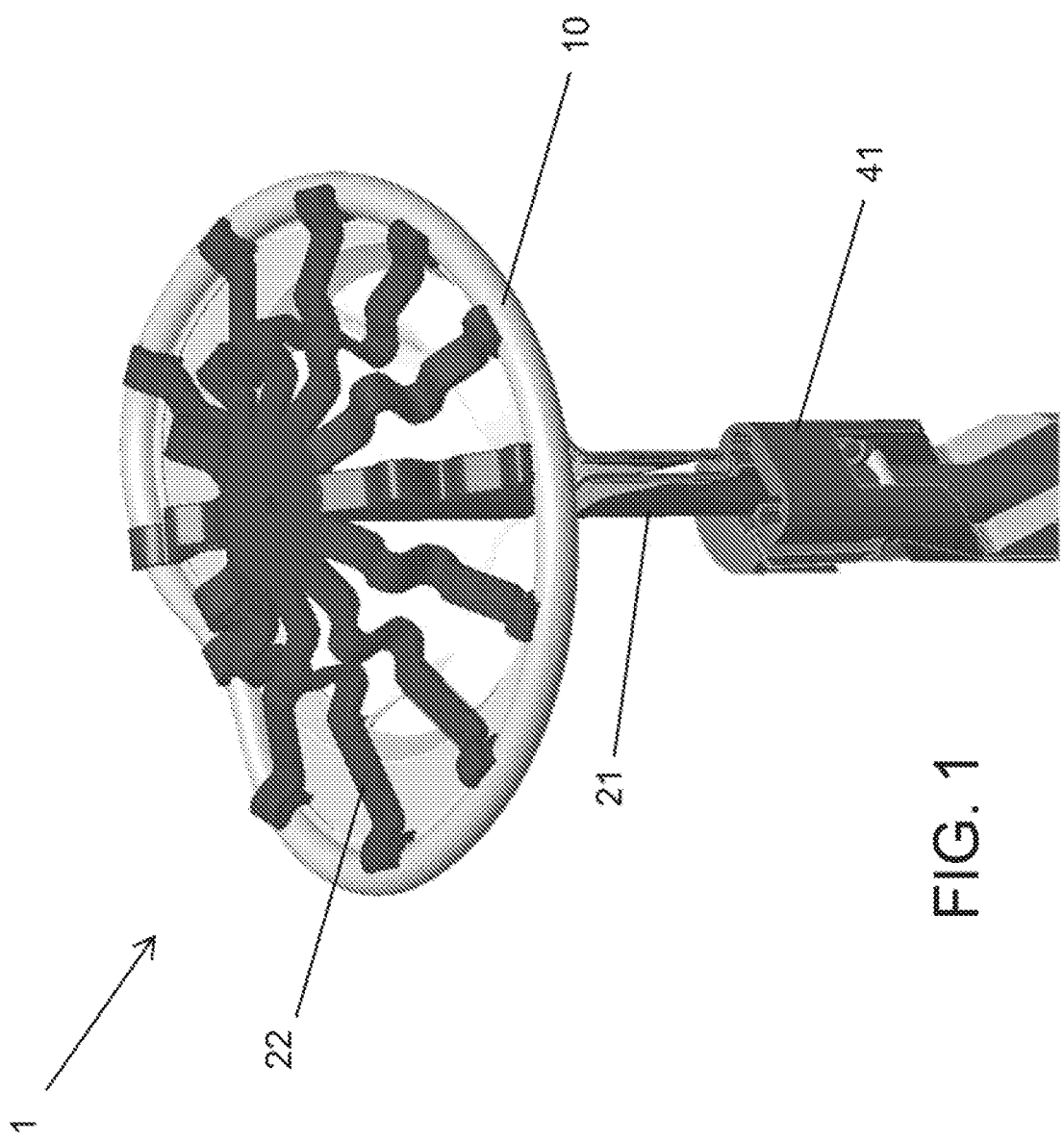
FIG. 1 is an illustration of the heart valve replacement prosthesis, the applicator shaft, the spring arms, and the driver, in accordance with an example embodiment of the present invention.

FIG. 1 illustrates heart valve replacement prosthesis 1 having ring 10, which, in an exemplary embodiment, may be elastic. FIG. 1 further illustrates applicator 20 having applicator shaft 21 and spring arms 22. Spring arms 22 may be affixed to the distal end of the applicator shaft 21, and may connect the distal end of the applicator shaft 21 to the ring 10 of the replacement prosthesis 1. FIG. 1 further illustrates driver 40, as will be described in more detail below.

As will be generally understood, as described by, for example, U.S. Pat. No. 7,621,948, the entirety of which is hereby incorporated by reference as if fully disclosed herein, the replacement prosthesis 1 of the present invention may be delivered to an implant site by first collapsing the replacement prosthesis 1 into a collapsed or folded position, such that the prosthesis fits within a cavity of a catheter. The catheter, including the collapsed or folded prosthesis, is advanced percutaneously to an implant site. Once the distal end of the catheter is adjacent to the implant site, the collapsed prosthesis may be pushed or forced through the distal end of the catheter.

Heart valve replacement prosthesis 1 may be formed of compliant, elastic material such as deformable plastic or nitinol, such that once the collapsed prosthesis emerges from the distal end of the catheter, the ring 10 may elastically return to an un-collapsed, or expanded formation, as illustrated in FIGS. 1 to 10. The prosthesis 1, including ring 10, may be maneuvered in the implant site, where it may be pressed into position in the implant site.

As further illustrated in FIGS. 1 to 10, ring 10 may, in an exemplary embodiment of the present invention, take on the shape of the implant site, which may be an irregular shape (e.g., non-circular). In the exemplary embodiments illustrated in FIG. 1 to 10, the ring 10 is formed to a non-circular, irregular shape. In this manner, the heart valve replacement prosthesis of the present invention may be adapted to a wide variety of implant sites, to address a wide variety of heart valve failures.

Figure 2:
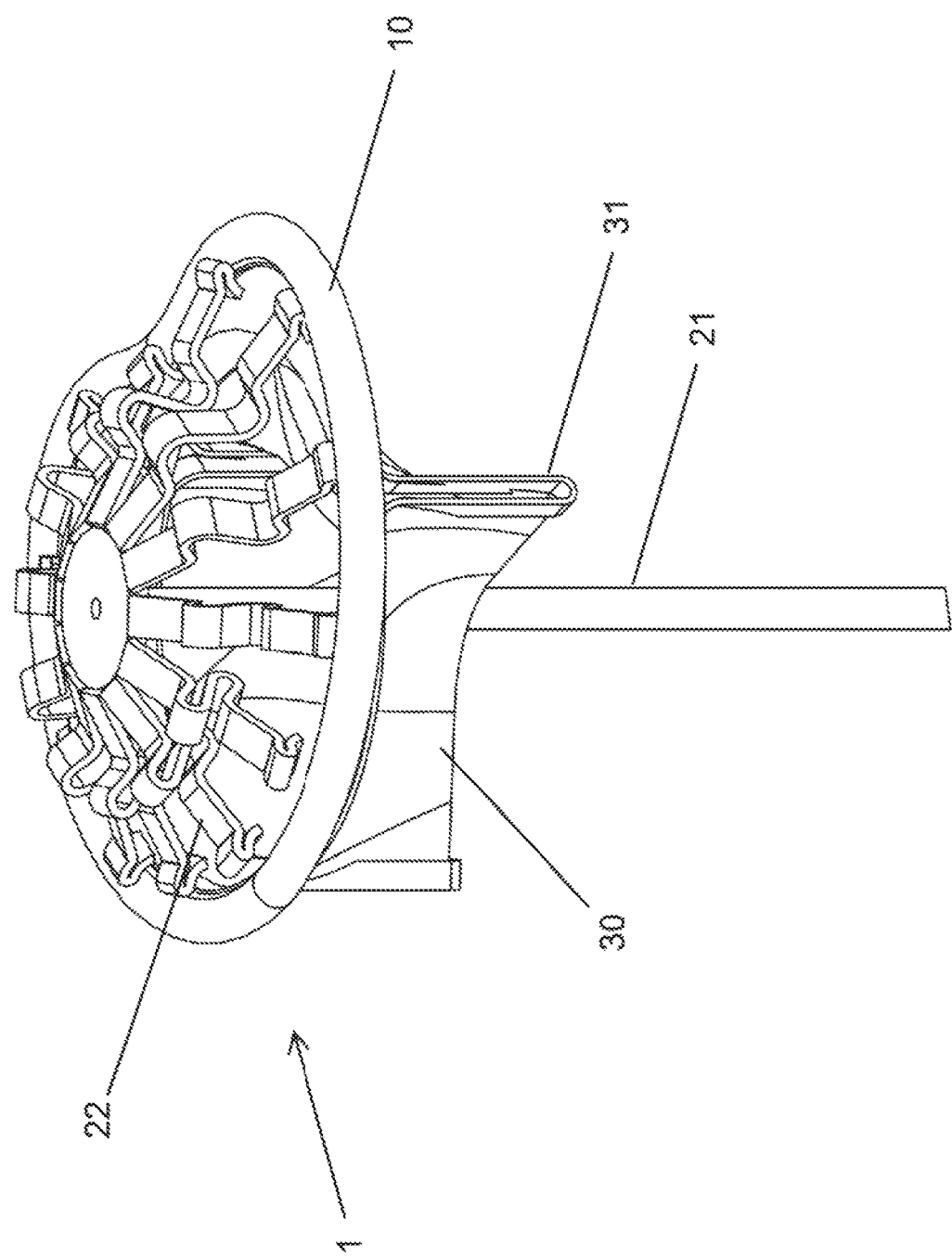
FIG. 2 is an illustration of the heart valve replacement prosthesis, the applicator shaft, and the spring arms, in accordance with an example embodiment of the present invention.

As illustrated in FIG. 2, heart valve replacement prosthesis 1 further includes leaflets 30, which perform the valve function. Leaflets 30 are connected to ring 10, and are further held in proper position by valve struts 31. Leaflets 30 are configured to prevent the flow of fluid in a first fluid flow direction, and to permit the flow of fluid in a second fluid flow direction.

FIGS. 2 through 8 illustrate an exemplary embodiment of the fixing of the replacement prosthesis 1 to the tissue of the implant site.

As illustrated in FIG. 2, replacement prosthesis 1 is expanded from the catheter, with ring 10 in a nearly fully expanded formation. Applicator shaft 21 extends from the proximal direction through and to the distal side of the ring 10. Spring arms 22 are connected to the distal end of the applicator shaft 21, such that the distal end of the applicator shaft 21 forms the apex of a conical shape formed by the spring arms 22 about the axis of the applicator shaft 21. Once delivered to the implant site, applicator shaft 21 may be used to press ring 10 into the tissue of the implant site, by pulling the applicator shaft 21 in a proximal direction, such that the force in the proximal direction is transferred to the spring arms 22, which in turn exert a force in a proximal and radial direction against the ring 10. Because the spring arms include spring elements 23, such as springs or spring-like ribbons, each spring arm is flexible to absorb force independently of the other spring arms. In this manner, ring 10 is further able to achieve an irregular shape, to meet the shape of any implant tissue. FIGS. 2 to 8 illustrate various spring arms 22 being extended or compressed to a different degree.

Figure 3:
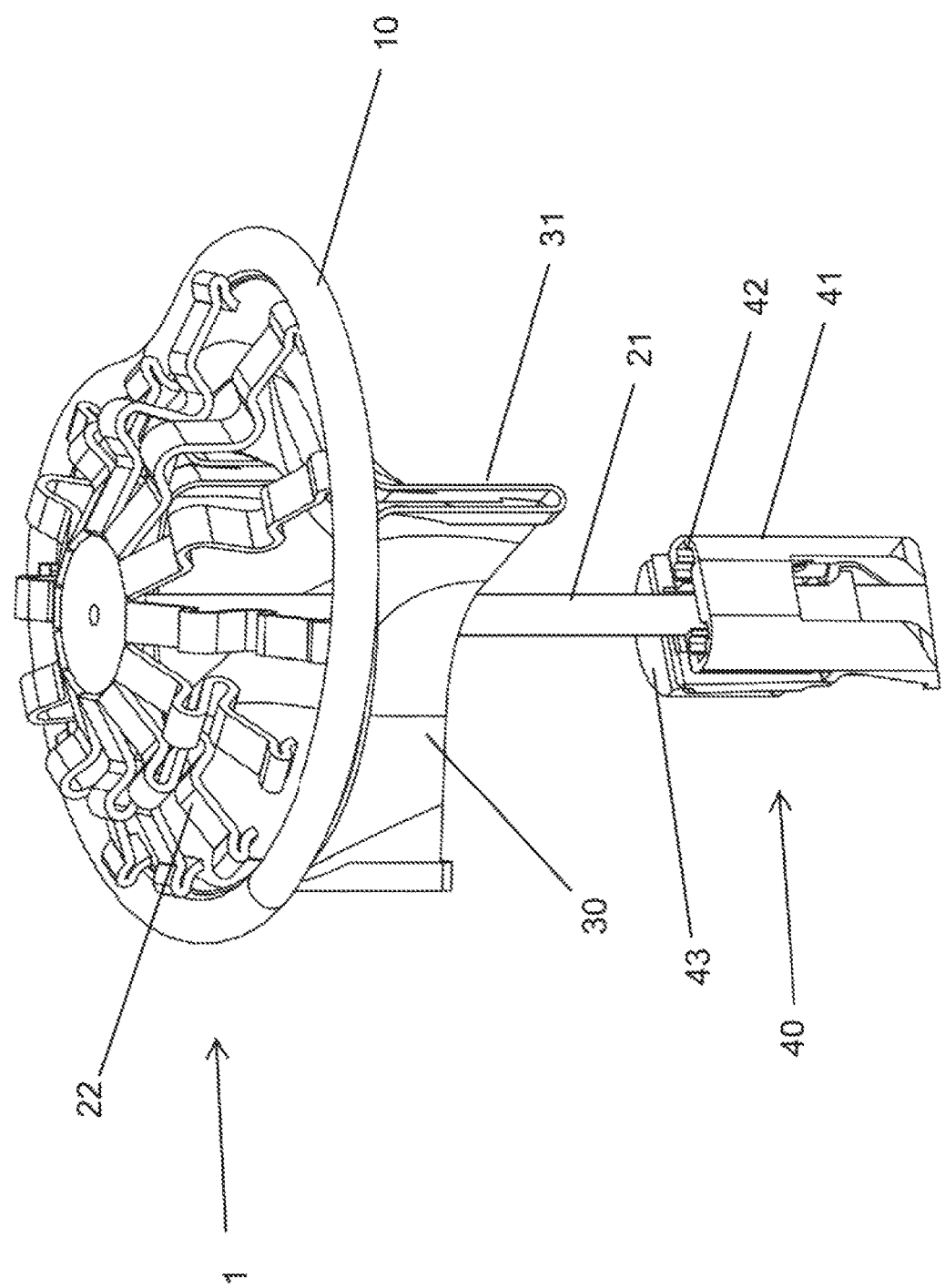
FIG. 3 is an illustration of the heart valve replacement prosthesis, the applicator shaft, the spring arms, and the driver, in accordance with an example embodiment of the present invention.

As illustrated in FIG. 3, once the prosthesis 1 is in place at the implant site, driver 40 may be actuated to fasten the ring 10 to the tissue of the implant site. Driver 40 includes firing arm 41, having anchor outlets 42, and a guide 43. Driver 40 may be operated to slide or otherwise move along the applicator shaft 21. Guide 43 and firing arm 41 may be situated on opposite sides of the applicator shaft 21, as illustrated in FIG. 3.

Figure 4:
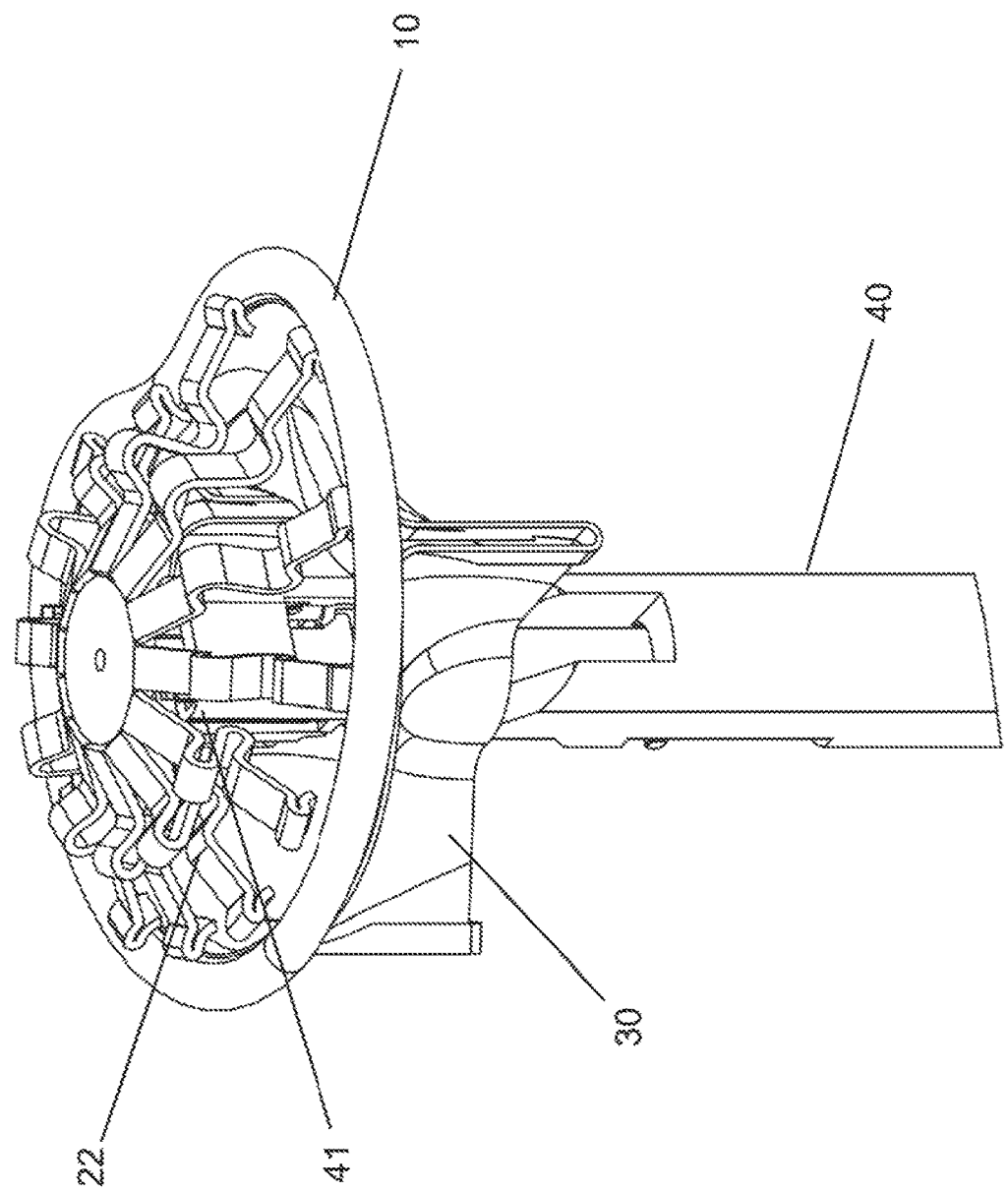
FIG. 4 is an illustration of the heart valve replacement prosthesis, the applicator shaft, the spring arms, and the driver, in accordance with an example embodiment of the present invention.

As illustrated in FIG. 4, driver 40 is moved to the distal end of the applicator shaft 21, where the applicator shaft 21 meets the spring arms 22.

Figure 5:
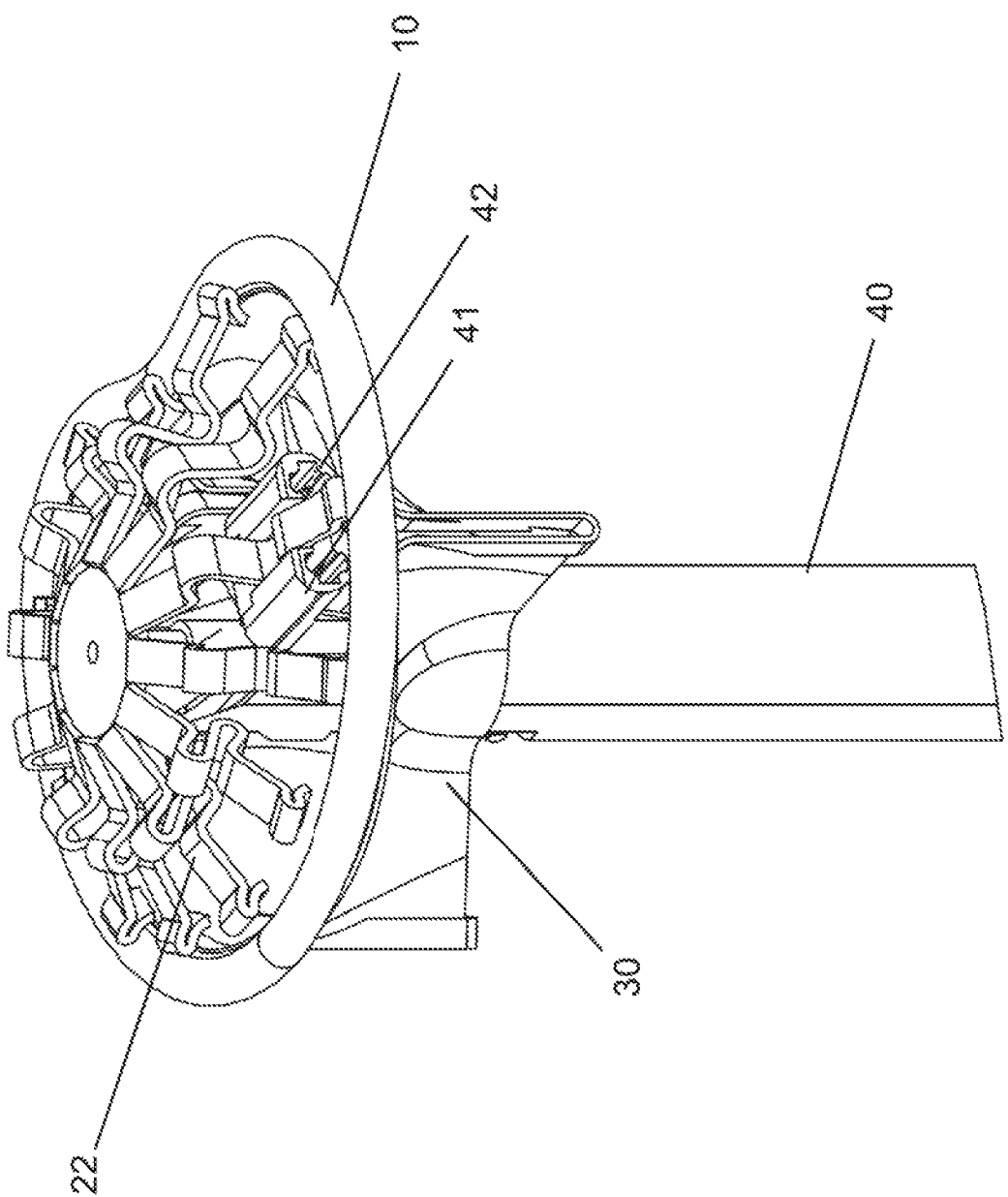
FIG. 5 is an illustration of the heart valve replacement prosthesis, the applicator shaft, the spring arms, and the driver, in accordance with an example embodiment of the present invention.

As illustrated in FIG. 5, firing arm 41 is configured to rotate from a position aligned with the axis defined by the applicator shaft 21 to a position directed radially away from the applicator shaft 21, so that the anchor outlets 42 of the firing arm are directed towards the ring 10.

Figure 6:
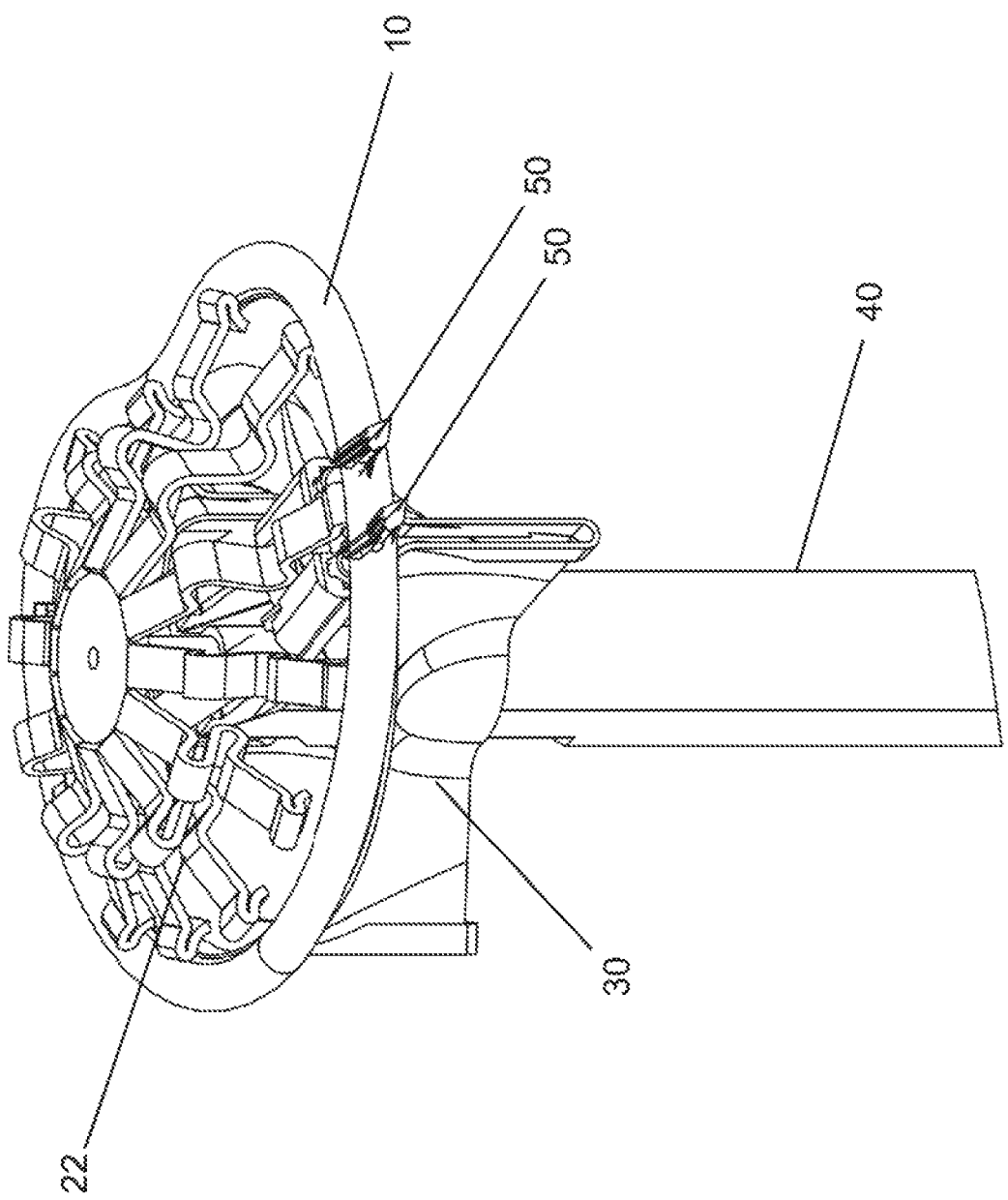
FIG. 6 is an illustration of the heart valve replacement prosthesis, the applicator shaft, the spring arms, and the driver, in accordance with an example embodiment of the present invention.

As illustrated in FIG. 6, firing arm 41 may be configured to drive anchors 50 through anchor outlets 42. Anchors 50 may be driven through ring 10, and into surrounding tissue of the implant site, fixing or fastening the ring 10 to the tissue of the implant site.

Figure 7:
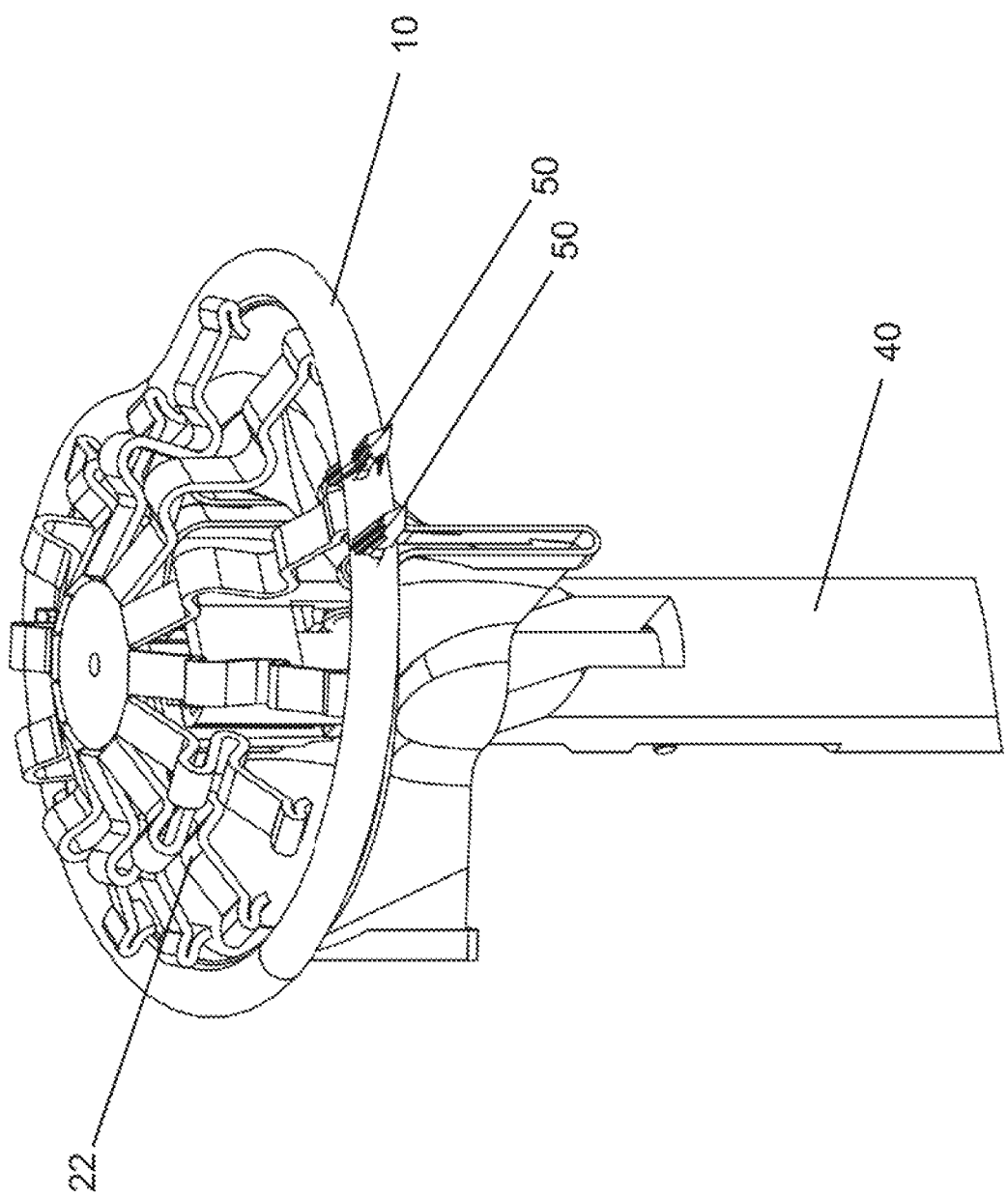
FIG. 7 is an illustration of the heart valve replacement prosthesis, the applicator shaft, the spring arms, and the driver, in accordance with an example embodiment of the present invention.
Figure 8:
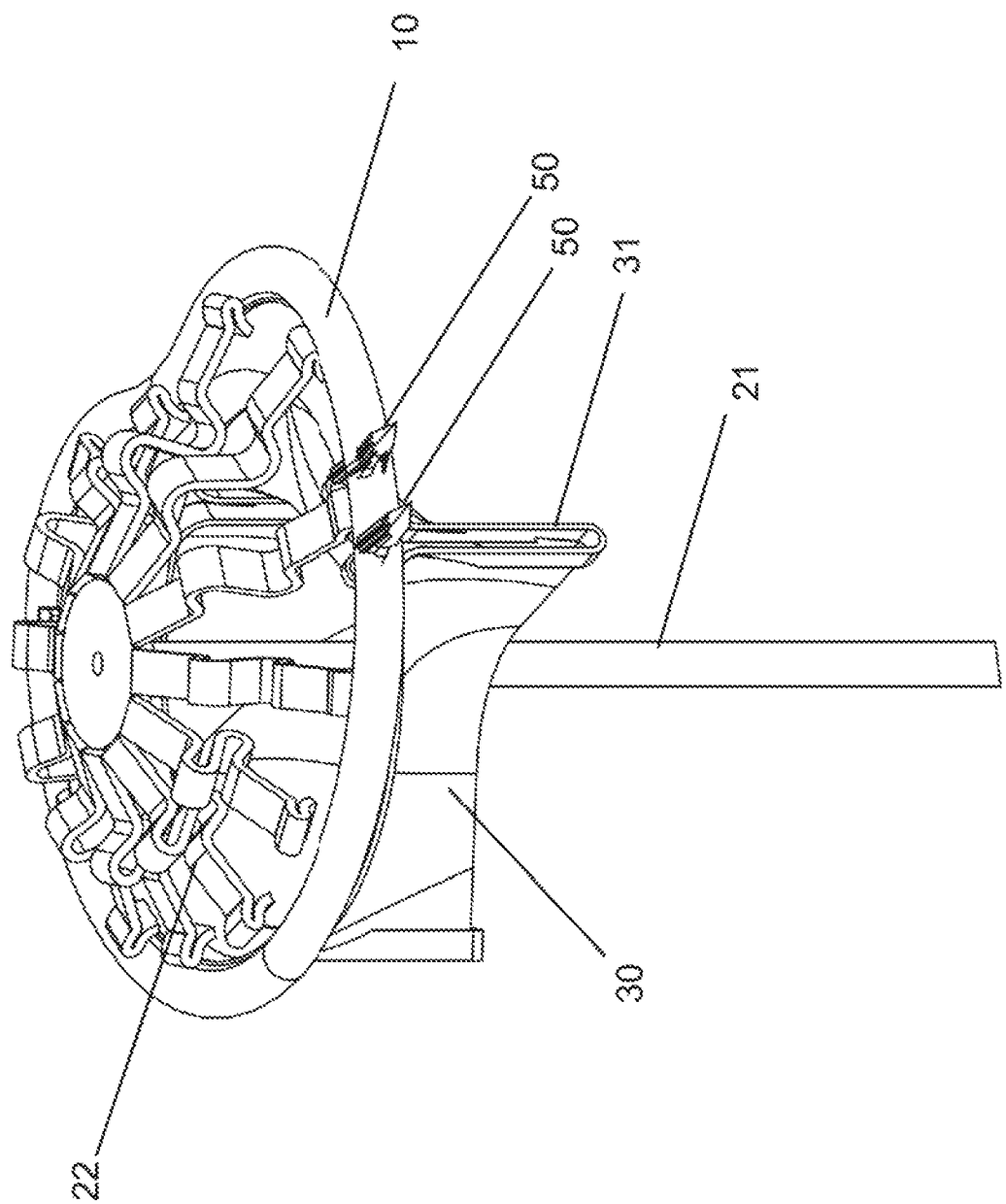
FIG. 8 is an illustration of the heart valve replacement prosthesis, the applicator shaft, the spring arms, and the driver, in accordance with an example embodiment of the present invention.

As illustrated in FIG. 7, once anchors 50 are driven into ring 10 and the surrounding tissue, firing arm 41 may be rotated back into alignment with the axis defined by the applicator shaft 21, so that the driver 40 may be retracted from the distal end of the applicator 20, as illustrated in FIG. 8.

In an exemplary embodiment of the present invention, the driving of anchors 50 may be repeated by driver 40 and firing arm 41, so as to drive anchors 50 around the ring 10. A plurality of anchors 50 may be loaded into a cartridge or tray of anchors, such that additional anchors may be loaded into a position to be driven into ring 10 and the surrounding tissue. Driver 40 may index the driving of each anchor 50 to the position of each spring arm 22 about the periphery of the ring 10. In the alternative, applicator shaft 21 may have grooves or other markings to which driver 40 may index the driving of each anchor 50.

Figure 9:
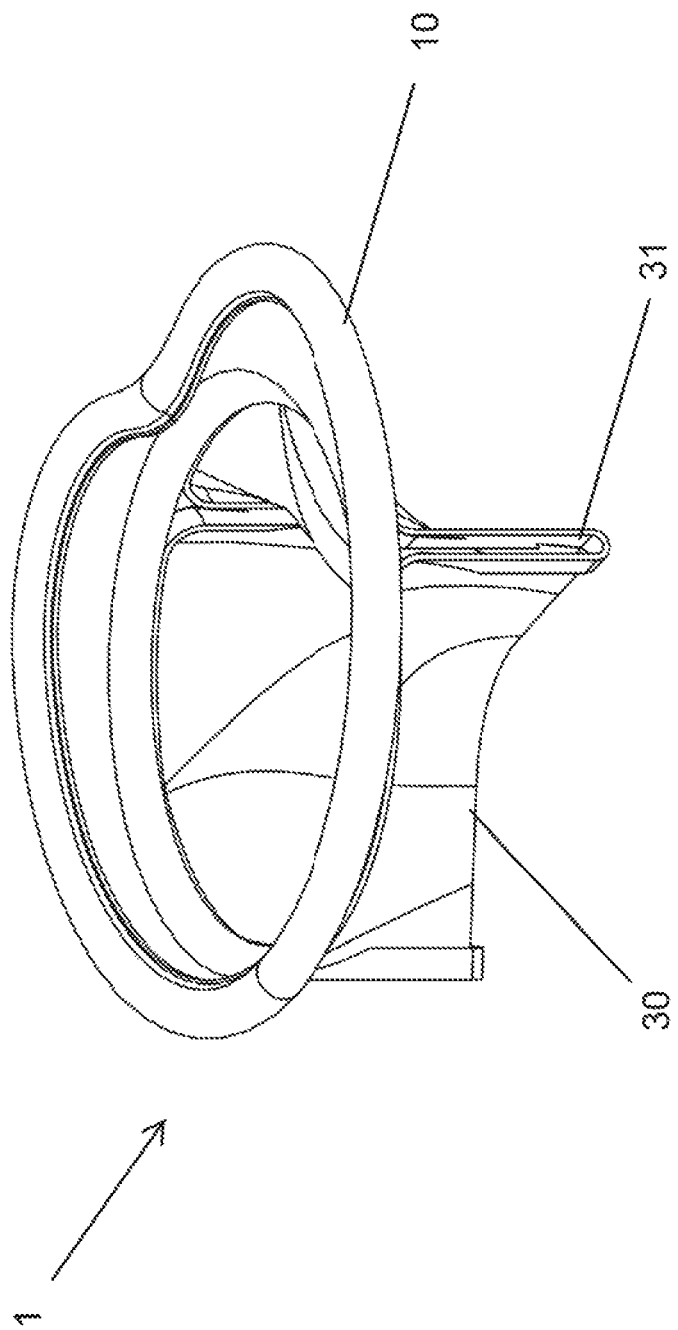
FIG. 9 is an illustration of the heart valve replacement prosthesis in accordance with an example embodiment of the present invention.

As illustrated in FIG. 9, heart valve replacement prosthesis 1 is shown alone, absent applicator 20, driver 40, or anchors 50.

Figure 10:
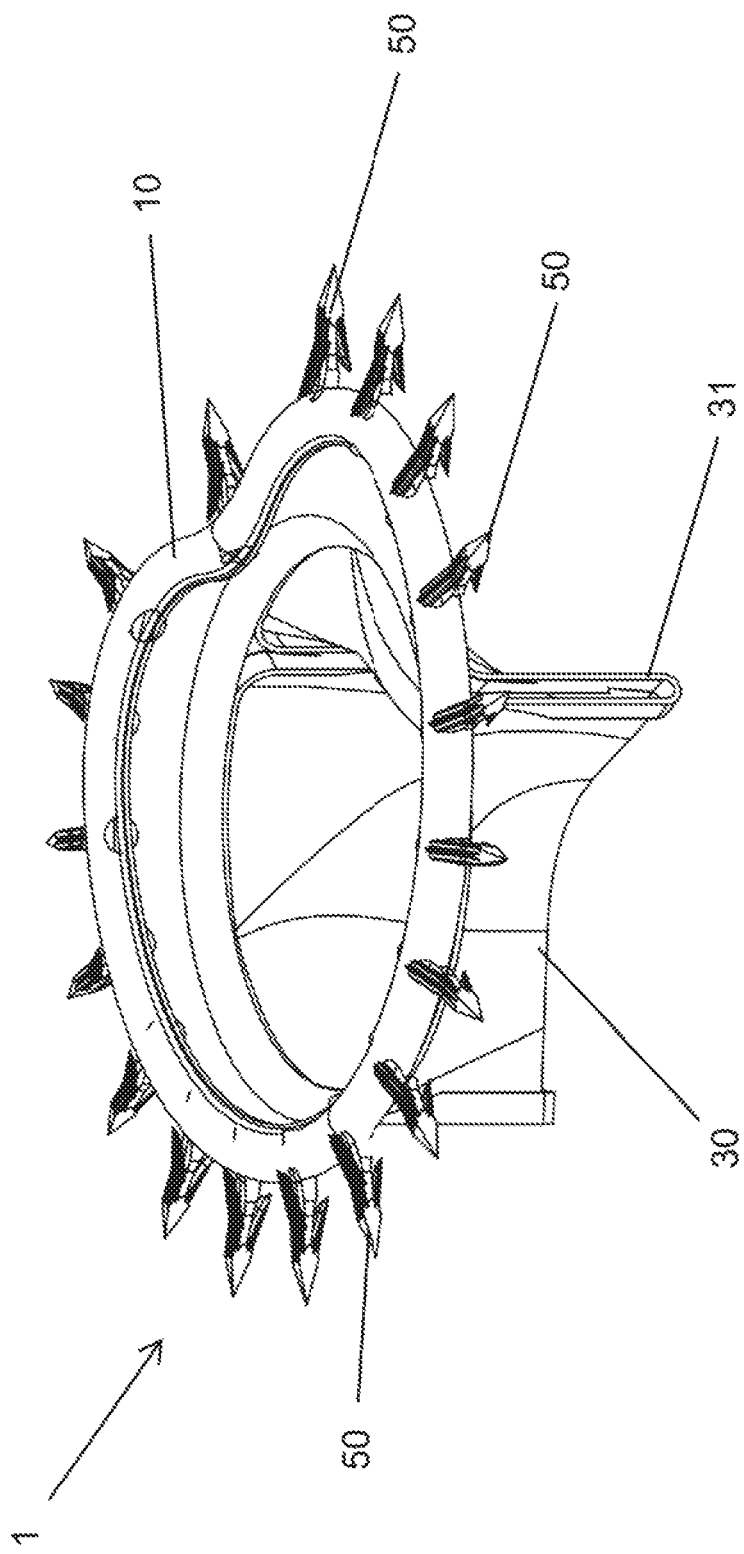
FIG. 10 is an illustration of the heart valve replacement prosthesis in accordance with an example embodiment of the present invention.

FIG. 10 illustrates the heart valve replacement prosthesis 1 after the driver 40 has completed driving a plurality of anchors 50 about the periphery of ring 10, and further after the applicator 20, including applicator shaft 21 and spring arms 22, have been withdrawn. To withdraw the applicator 20, the applicator shaft 21 may be moved in a distal direction, extending spring arms 22 further beyond the distal side of the ring 10, and permitting the conical structure formed by the spring arms 22 to collapse. Once collapsed, the spring arms 22 may be permitted to pass through ring 10 with the withdrawal of the applicator shaft 21, so that the entire applicator 20 may be withdrawn from the implant site.

Anchors 50 may be any of the anchors described herein, in U.S. Patent Provisional Application No. 61/296,868, filed Jan. 20, 2010, U.S. patent application Ser. No. 13/010,766, filed Jan. 20, 2011, U.S. patent application Ser. No. 13/828, 256, filed Mar. 14, 2013, U.S. patent application Ser. No. 13/843,930, filed Mar. 15, 2013, U.S. patent application Ser. No. 14/301,106, filed Jun. 10, 2014, U.S. Patent Provisional Application No. 62/088,680, filed Dec. 7, 2014, and U.S. patent application Ser. No. 14/737,408, filed Jun. 11, 2015, each of which is incorporated by reference in their entirety as if fully disclosed herein.

Figure 11:
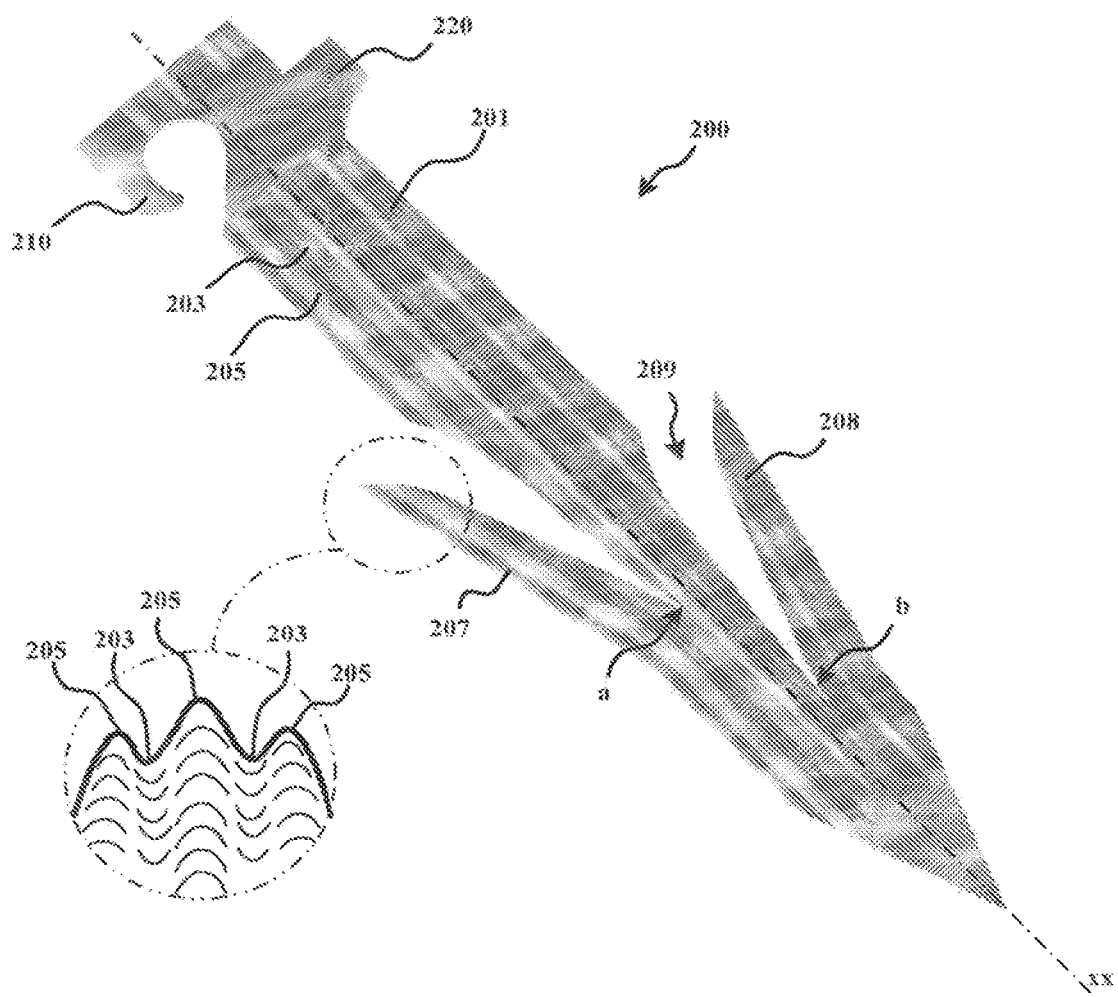
FIG. 11 is an illustration of an anchor in accordance with an exemplary embodiment of the present invention.

For example, FIG. 11 shows an anchor or implant 200 which is configured to be driven into a tissue. The anchor 200 includes a corrugated body 201. The body 201 includes grooves 203 that extend axially along the length of the body 201. Thus, extending circumferentially around the body 201, a plurality of grooves 203 alternate with a plurality of ridges 205. Further, the anchor body 201 includes a pair of wings or split portions 207 and 208. The split portions 207 and 208 are formed by respective splits or cuts 209 into the body 201. In this regard, the splits 209 may be formed by making a cut radially into the body 201 and extending in an axial direction. Thus, the two split portions 207 and 208 are attached to the remainder of the body 201 at a distal position and extend proximally to free ends. The free ends include a plurality of sharp protrusions along a curved surface. These points are formed due to the corrugations. In particular, the ridges 205 form the sharp protrusions, as illustrated in the inset partial side view in FIG. 11, which are advantageous for gripping tissue and preventing distal sliding of the anchor 200. Although each split portion 207 and 208 includes three such protrusions as illustrated, it should be understood that the anchor 200 may be designed such that one or more of the split portions has any other number of protrusions, including a single sharp protrusion. For example, if a larger number of sharp protrusions are desired, the body 201 could be more densely corrugated (i.e., a greater number of alternating grooves 203 and ridges 205 could be provided) and/or the angle of the cut or slice could be adjusted. Further, the length of proximal extension of the projections may be adjusted by varying the depth of the grooves 203 with respect to the ridges 205.

The split portions 207 and 208 do not substantially impede distal insertion into tissue but resist proximal movement from an insertion location by engaging the tissue. It has been discovered that the combination of the pointed and/or sharp-edged proximal ends of the split portions 207 and 208 with the alternating ridges on the proximal end of the split portions creates improved performance.

Further, the split portions or wings 207 and 208 are axially offset from each other. For example, split 207 is axially located at position along axis xx and split 208 is axially located at position b along axis xx. This allows for greater structural strength of the other portions of the body 201 as compared to a non-offset configuration. In particular, since the cuts progress continually radially inward as they progress distally, a non-offset portion would have a substantially smaller amount of material in cross-section at the distal end of the cut. This would lead to a mechanically weak point or region along the axis of the body and could lead to mechanical failure, especially in anchors of small dimensions. Although the anchors 200 utilize a pair of wings 207 and 208 to anchor the anchors 200 against proximal retraction from a tissue, it should be appreciated that any number of wings may be provided, and that as an alternative or in addition to the wings 207 and 208, any other appropriate anchoring structure(s), e.g., anchoring filaments, may be provided.

The distal tip of the anchor 200 is pyramidal, with a sharp point, and a plurality of surfaces separated by edges that converge at the sharp point. Although four planar surfaces are provided, it should be appreciated that any appropriate suitable number of surfaces may be provided and that one or more or all of the surfaces may be non-planar.

The anchor 200 may include one or more shoulders, formed by the junction of a wing 207, 208, with the body 201, or otherwise defined by the area of the anchor 200 where the wing 207, 208, extends proximally and radially outwardly from the distal end, or distal thereto. As illustrated in FIG. 11, wings 207, 208, have a relaxed, uncompressed position, but may be compressed to a second, compressed position, in closer approximation with the body 201. Further, the body 201 may be flexible, such that forces experienced in the proximal end may influence the position of the body or stem 201 with respect to the wings 207, 208, and the distal end.

The anchor 200 may be produced by first forming the body 201 with the corrugations, e.g., by injection molding or extrusion, and subsequently forming split portions 207 and 208, e.g., by cutting radially into the side of the body 201. As illustrated, the cut is curved, with an angle (at the proximal entry point), relative to the longitudinal axis xx of the body 201, that gradually decreases from the proximal initial cutting location toward the distal end of the anchor 200 and eventually becoming linear. Although the split or cut of the illustrated example is made with a curved or varying angle with respect to the longitudinal axis xx of the body 201, it should be understood that any appropriate cut, including a linear cut, may be made.

Although the anchor 200 includes two wings or split portions spaced equally around the radial periphery of the body 201, it should be appreciated that any number of split portions, including a single split portion may be provided and at any appropriate spacing around the radial periphery of the anchor 200.

Modern manufacturing processes allow for near nano technology applications. This allows the anchors to be manufactured in a size and complexity that may not have been possible in years past. The anchor 200 may be injection molded of either absorbable or non-absorbable polymers and then processed (e.g., by cutting) to add the features of the wings 207 and 208. Although the anchors 200 are formed of polymer, it should be appreciated that any appropriate material may be used, e.g., metal or a composite material. The anchors 200 may have a diameter of, e.g., one millimeter, or approximately one millimeter, and a length that is in a range from, e.g., 5 millimeters to 10 millimeters. According to some example embodiments, the diameter is less than one millimeter. According to some example embodiments, the diameter is in a range from 0.8 millimeters to 1.2 millimeters. It should be understood, however, that other dimensions may be provided.

Figure 12:
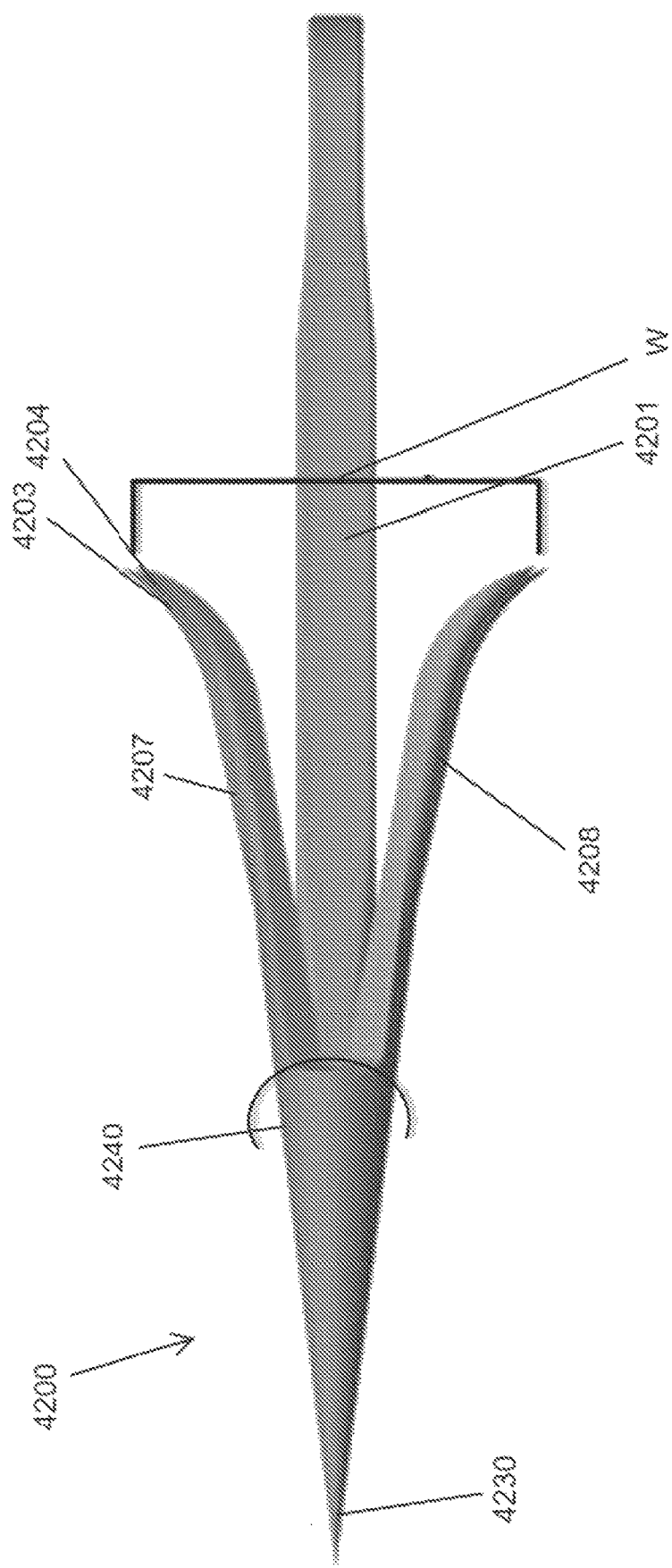
FIG. 12 is an illustration of an anchor in accordance with an exemplary embodiment of the present invention.

In an exemplary embodiment of the present invention, the anchor 4200 illustrated in FIG. 12 is described. Anchor 4200 includes a distal tip 4230, and a stem 4201 extending proximally from the base of distal tip 4230. Stem 4201 joins the base of distal tip 4230 at shoulder 4240. Wings or barbs 4207, 4208 extend proximally, and, to some degree, radially, from the base of distal tip 4230, and join the base of distal tip 4230 at shoulder 4240. Barbs 4207, 4208 extend proximally and radially from the distal tip 4230 to free ends. The free ends may flare further radially outward, as illustrated in FIG. 12. Unlike the wings or split portions 207, 208 described above, wings or barbs 4207, 4208 are not formed from cuts or splits to the body of the anchor, so that the thickness of stem 4201 may be unaffected by the inclusion of barbs 4207, 4208. Wings or barbs 4207, 4208 may have a relaxed, uncompressed position, illustrated in FIG. 12. In the uncompressed position, barbs 4207, 4208 are unbiased, having a barb opening W. Barbs 4207, 4208 may be compressed into closer approximation with stem 4201. Varying amounts of compression may be applied to the barbs, such that the greater the compression, the closer approximation of the barbs to the stem. Barbs 4207, 4208 may include protrusions at the free ends of the barbs, to engage with tissue once the anchor has been deployed. While two barbs 4207, 4208 are illustrated, it should be appreciated that any number of barbs may be provided. Similarly, any number of protrusions at the free ends of the barbs may be provided, including one sharp protrusion.

Stem 4201 may be flexible, able to be bent or flexed with respect to barbs 4207, 4208 and distal tip 4230. Once deployed into tissue, a flexible stem provides for a different profile of forces acting on the anchor 4200, as compared to an anchor having a rigid or stiff stem. A flexible shaft, able to flex in relation to the barbs and the distal tip, creates a living hinge between these elements of the anchor. Forces acting on the anchor from its proximal end may be at least partially absorbed by the flexible stem, so that the impact of these forces on the wings or barbs of the anchor may be reduced. In certain tissue environments, a flexible shaft may be more likely to prevent a levering action by the anchor, and may thereby prevent the anchor from partially or even completely pulling out of the tissue.

Further, the anchors 50, 200, 4200 may include any of the features of the fasteners or other analogous implants disclosed in U.S. Provisional Patent Application Ser. No. 61/296,868, filed on Jan. 20, 2010, in U.S. patent application Ser. No. 13/010,766, filed on Jan. 20, 2011, and U.S. patent application Ser. No. 14/301,106, filed on Jun. 10, 2014, each of which is incorporated by reference in its entirety as if fully disclosed herein, and may be driven using any mechanism disclosed therein.

To fire the anchors, a force delivery system may be situated at the proximal end of the driver. The force delivery system may use any mechanisms of nearly instantaneous force transfer, such as springs, gas, compressed fluid, or the like. Force is transferred through the shaft of the driver, which may be a rigid shaft or a flexible shaft, depending on the application. The force is used to displace a firing mechanism at the distal end of the shaft, which in turn exerts a driving force on the anchors to drive the anchors from the firing arms and into the prosthetic valve and the surrounding tissue. The driving force may result from a pushing force delivery system, which directs force in the distal direction of the driver, or a pulling force delivery system, which directs force in the proximal direction of the driver, depending on the application.

Figure 13:
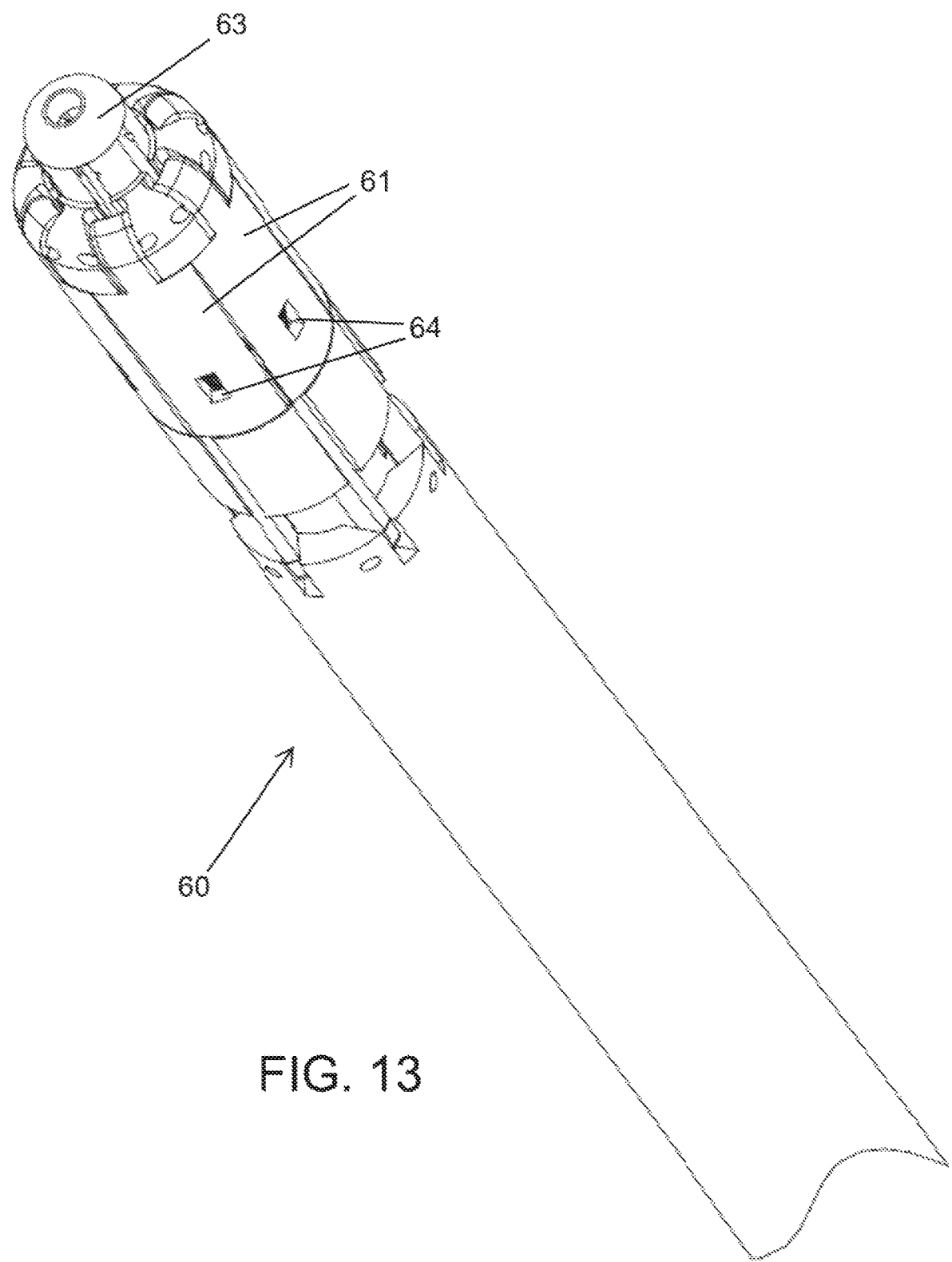
FIG. 13 is an illustration of the driver of the heart valve replacement prosthesis in accordance with an example embodiment of the present invention.
Figure 14:
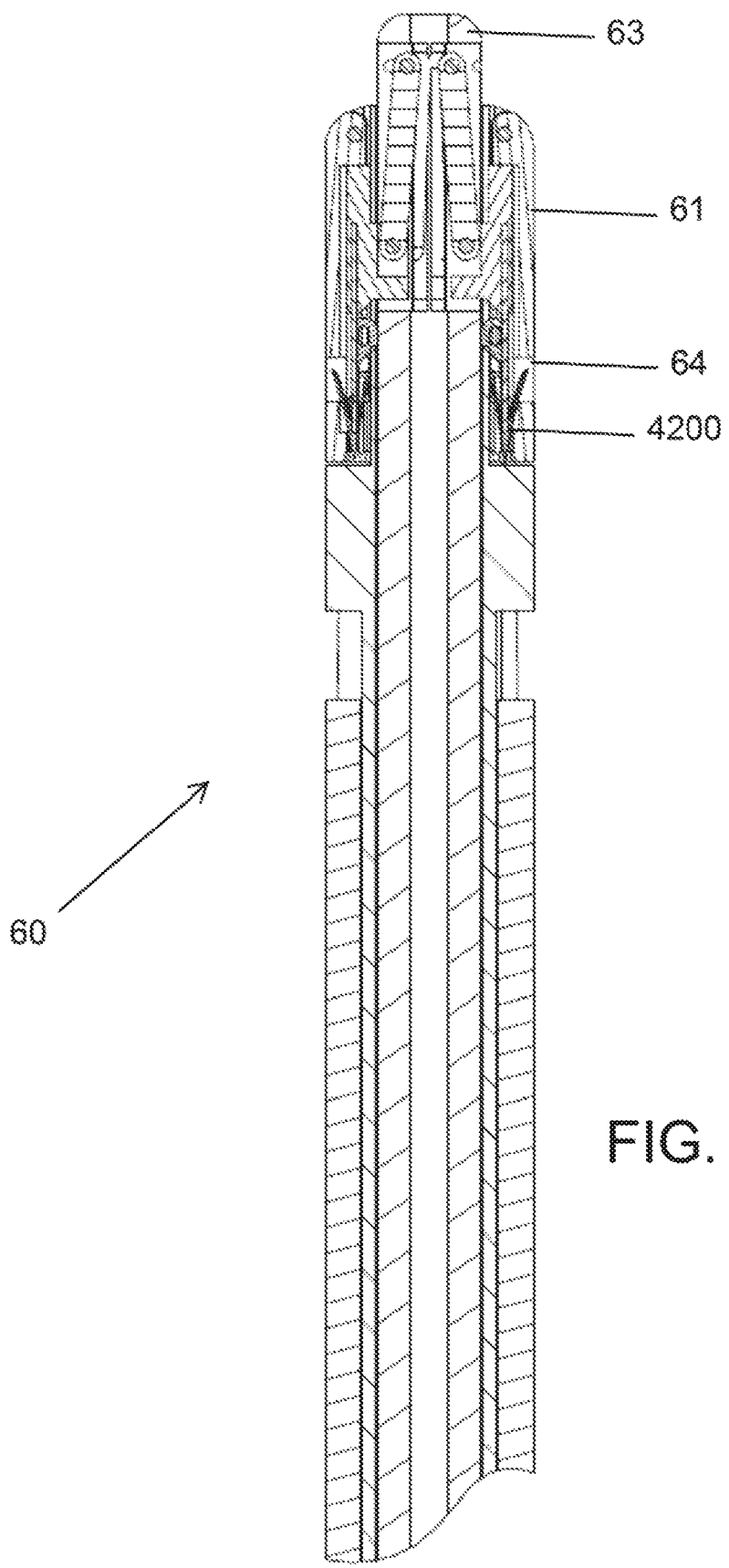
FIG. 14 is an illustration of a cross-sectional view of the driver of the heart valve replacement prosthesis in accordance with an example embodiment of the present invention.

In an exemplary embodiment of the present invention, a plurality of firing arms may be provided around the applicator, as illustrated in FIGS. 13 to 20. FIGS. 13 and 14 show driver 60 having, at its distal end, a plurality of firing arms 61 situated annularly around tubular guide 63. Guide 63 may surround an applicator shaft, much like guide 43. Firing arms 61 are in a retracted position against the driver and parallel to the axis of the driver. FIG. 14 also shows anchors 4200 provided in the firing arms 61. Windows 64 allow for the barbs 4207, 4208 to be stored in the firing arm 61 in their relaxed position before being driven from the anchor outlet and into the ring 10 and the surrounding tissue.

Figure 15:
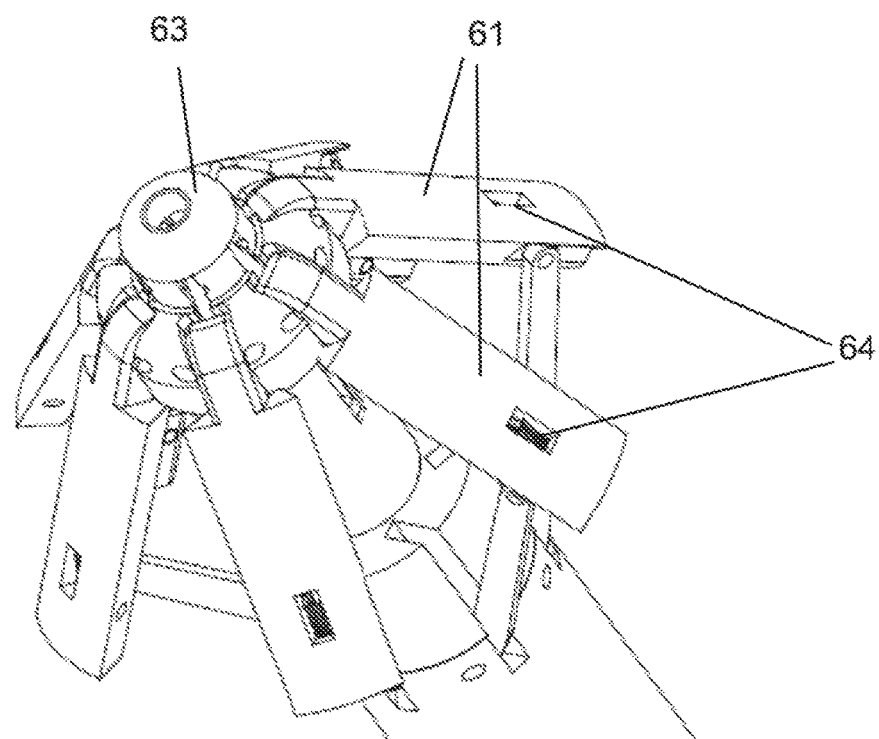
FIG. 15 is an illustration of the driver of the heart valve replacement prosthesis in accordance with an example embodiment of the present invention.
Figure 16:
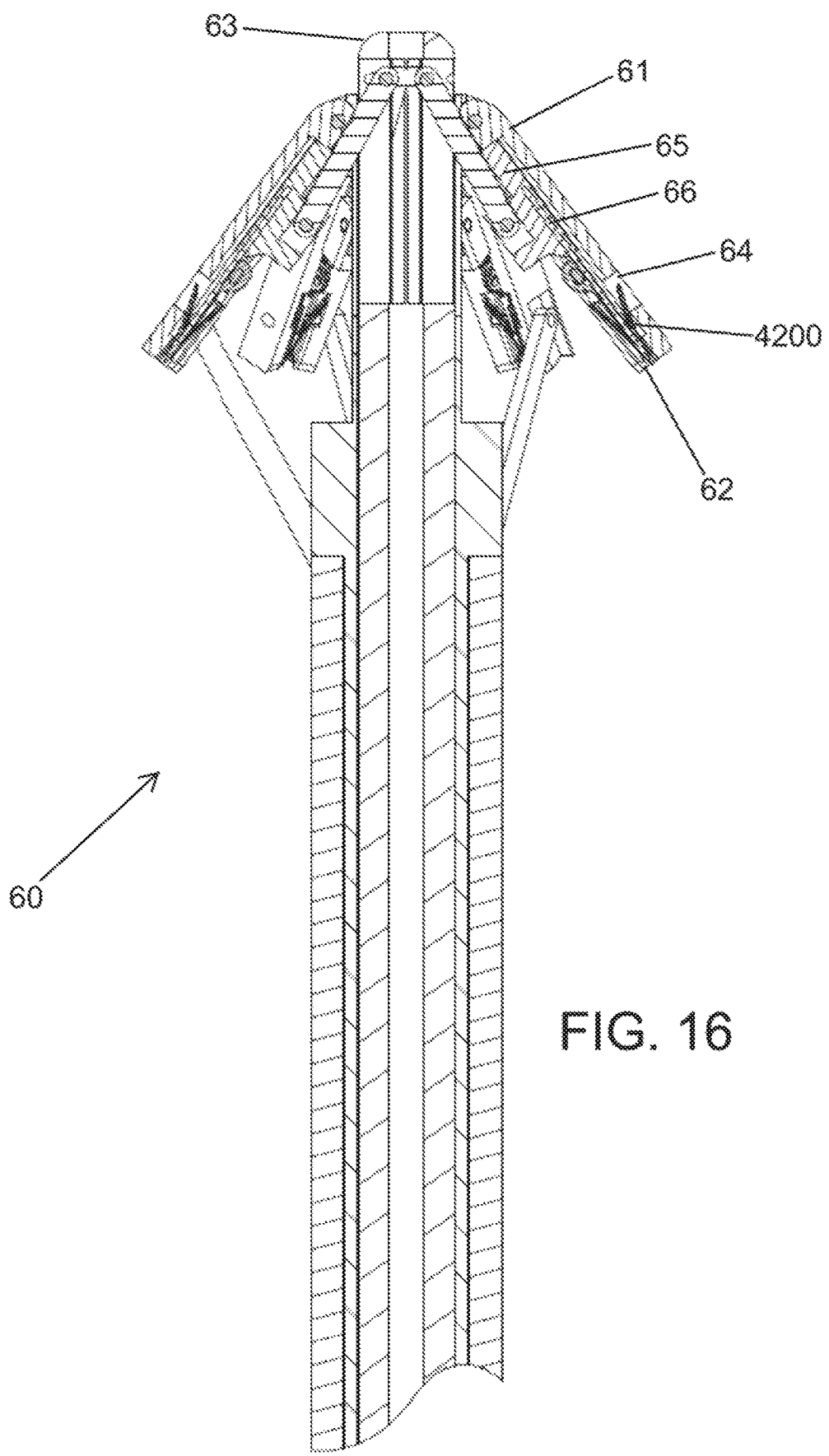
FIG. 16 is an illustration of a cross-sectional view of the driver of the heart valve replacement prosthesis in accordance with an example embodiment of the present invention.

FIGS. 15 and 16 illustrate the driver 60 in which the firing arms have been moved from the retracted position to a firing position. The movement of the firing arms from the retracted position of FIGS. 13 and 14 to the firing position of FIGS. 15 and 16 may be achieved by manual or electric actuation of a translating force, for example, by a screw or a sliding mechanism, or by any other mechanical operation. Firing arms 61 are hinged to driver 60 at the distal end of the driver, so that the firing arms 61 open radially outwardly from a position proximal to the hinges and the distal end of the driver 60. The firing position of the firing arms may be at an angle of less than 90 degrees from the axis of driver 60. An acute angle of firing arms 61 allows for an angled anchor delivery into ring 10 and the surrounding tissue, and therefore greater control of the placement of the anchors in the surrounding tissue.

As illustrated in FIG. 16, firing arms 61 include firing mechanisms 65 and fingers 66, for driving anchors 4200 through anchor outlets 62. Guide 63 is connected to firing mechanisms 65 and fingers 66, so that the application of a proximal or pull force to the guide will translate the force in a proximal direction to the firing mechanisms 65 and finger 66. Fingers 66 abut shoulder 4240 of anchor 4200, and may transfer the pull force from the guide 63 and firing mechanism 65 to anchor 4200.

Figure 17:
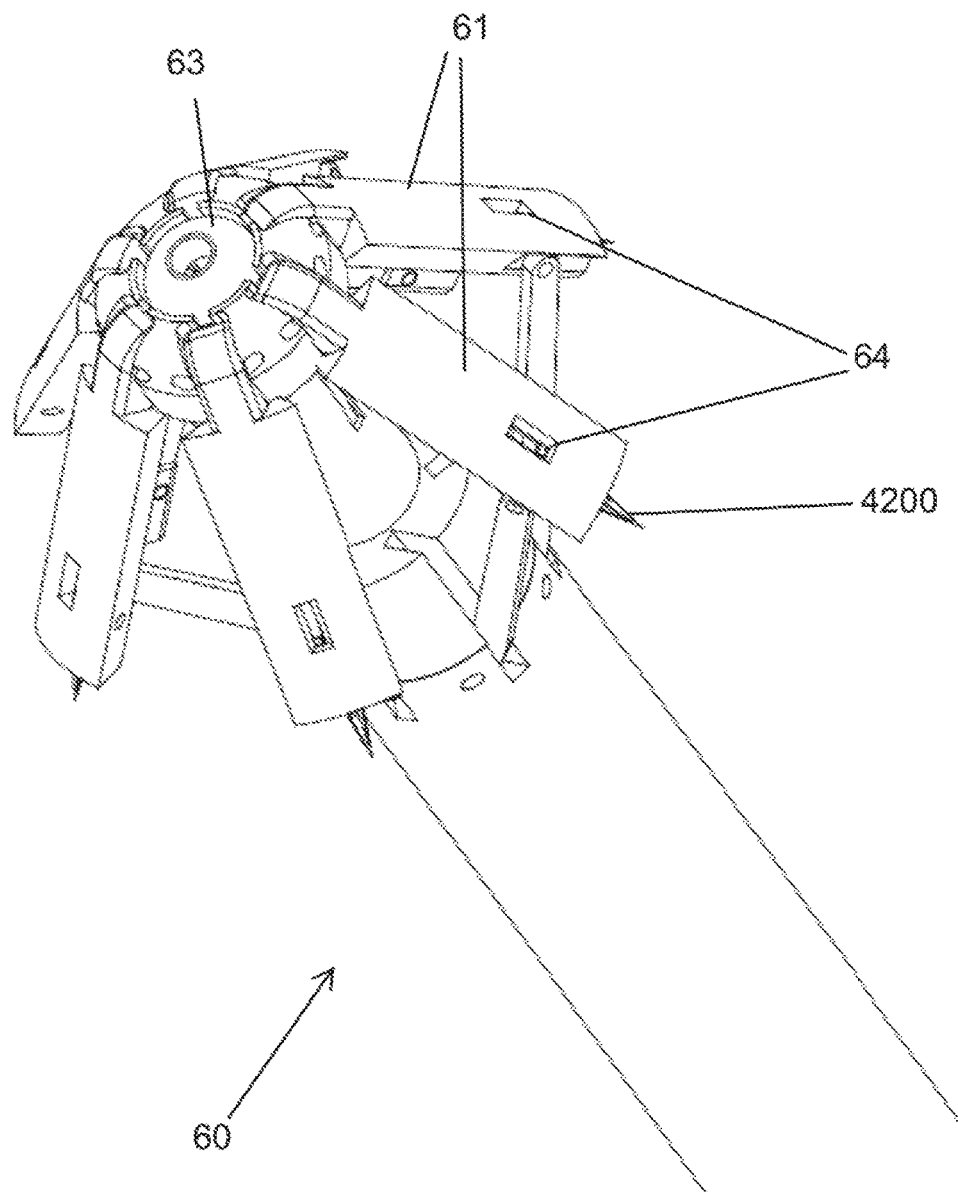
FIG. 17 is an illustration of the driver of the heart valve replacement prosthesis in accordance with an example embodiment of the present invention.
Figure 18:
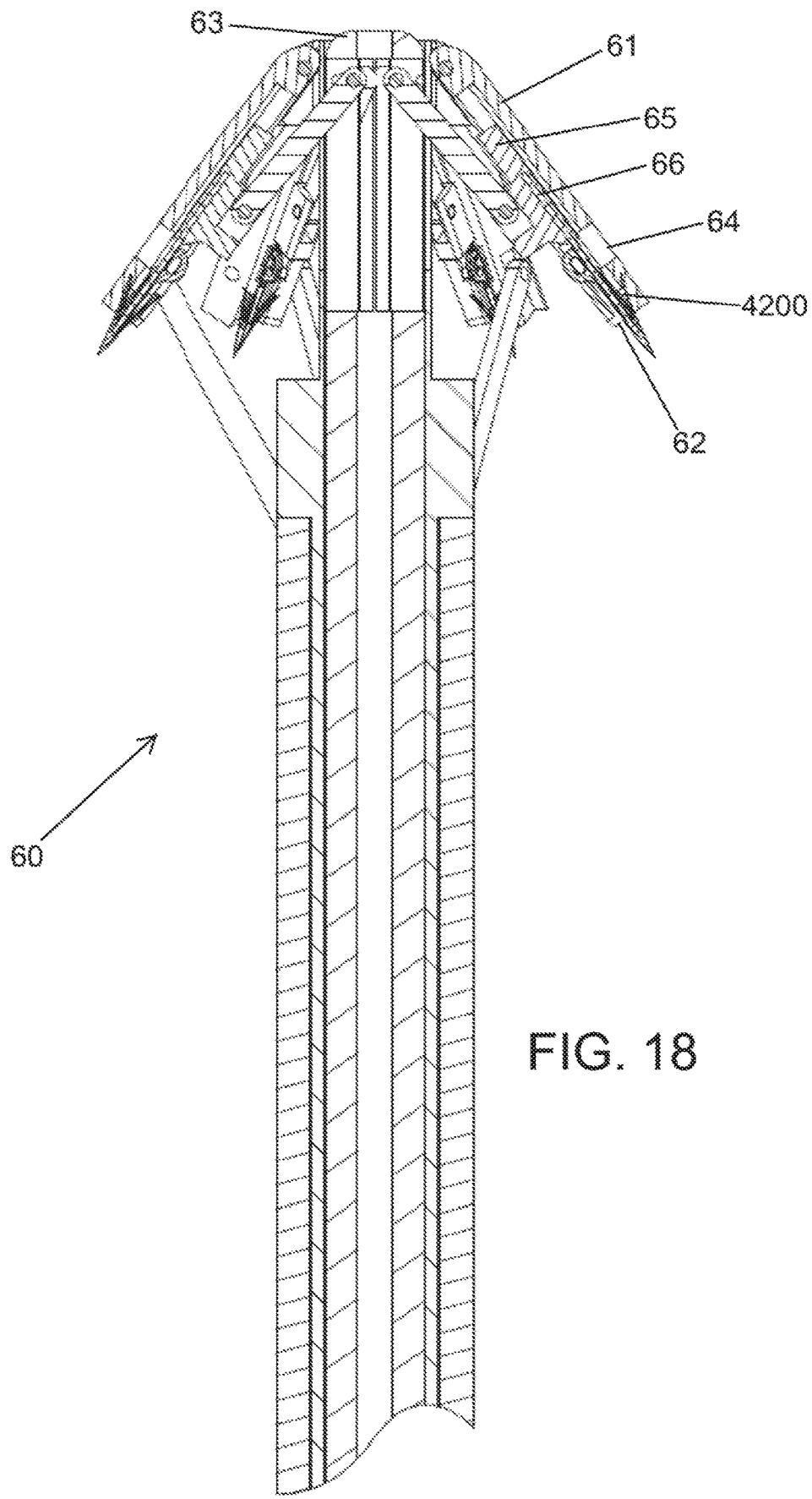
FIG. 18 is an illustration of a cross-sectional view of the driver of the heart valve replacement prosthesis in accordance with an example embodiment of the present invention.
Figure 19:
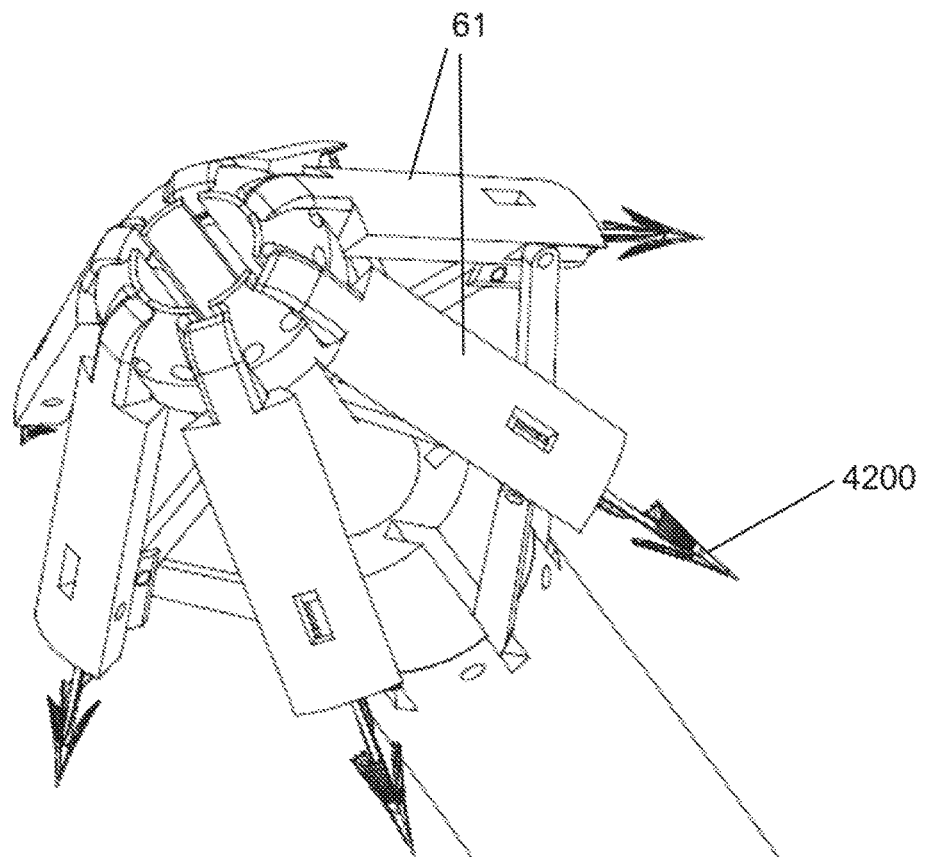
FIG. 19 is an illustration of the driver of the heart valve replacement prosthesis in accordance with an example embodiment of the present invention.
Figure 20:
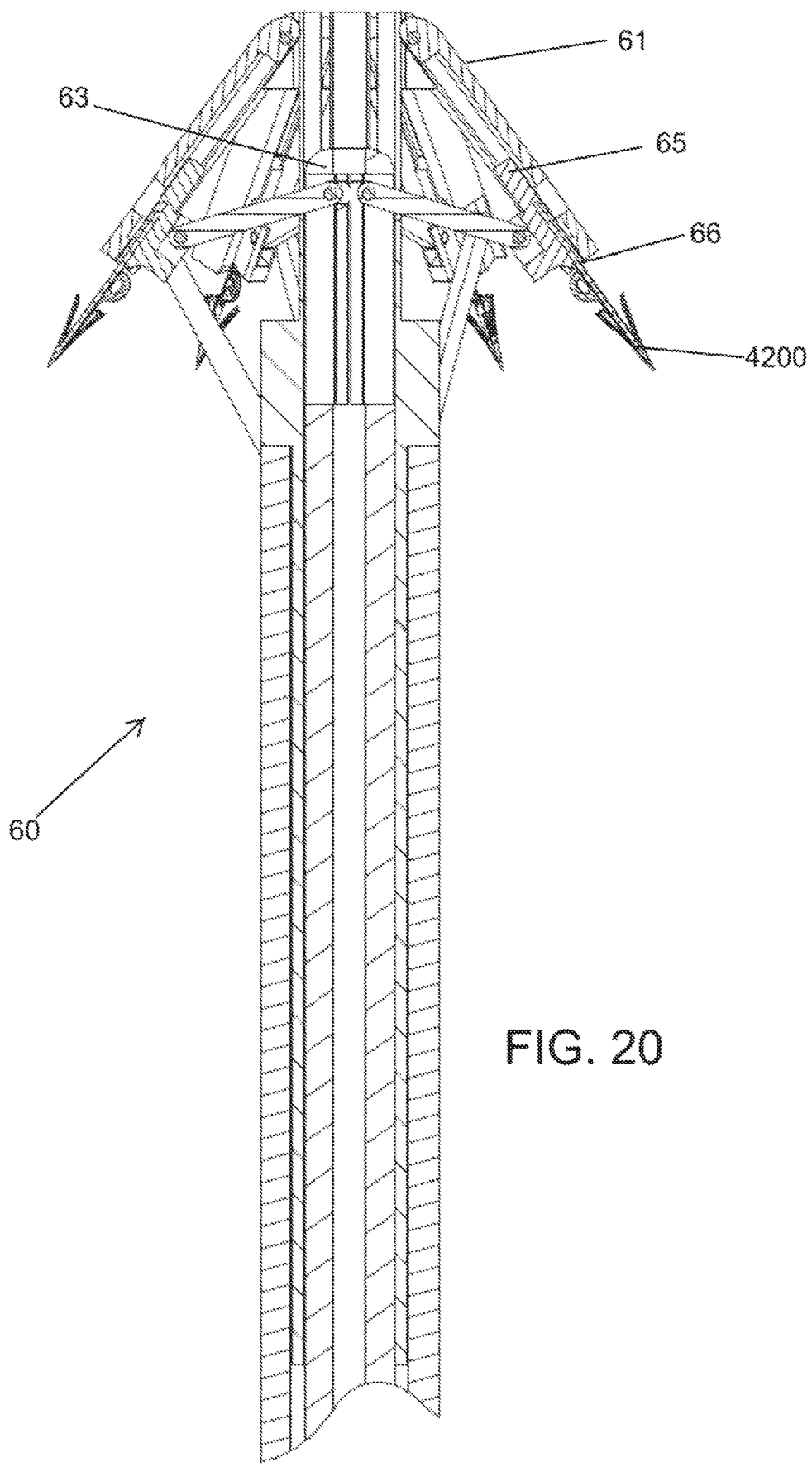
FIG. 20 is an illustration of a cross-sectional view of the driver of the heart valve replacement prosthesis in accordance with an example embodiment of the present invention.

FIGS. 17, 18, 19, and 20 illustrate the firing of anchors 4200. Anchors 4200 are fired by exertion of a proximal or pulling force, pulling guide 63 in a proximal direction with respect to driver 60. As shown in FIGS. 17 and 18, guide 63 is drawn nearly level with the hinged ends of firing arms 61, and, as shown in FIGS. 19 and 20, guide 63 is drawn to a recessed position with respect to the hinged ends of firing arms 61. The proximal force drawing guide 63 is transferred to firing mechanisms 65, and in turn to finger 66, which then transfers the driving force to shoulder 4240 of anchor 4200, driving anchor 4200 through anchor outlet 62, into ring 10 and the surrounding tissue. In this manner, all of the firing arms 61 may fire anchors 4200 at the same time.

FIGS. 21A-22D illustrate the 'ball and socket' version of the TCAT anchor 2101, where FIGS. 21A-21D show the tension spring 2104 in a relaxed state and FIGS. 22A-22D show tension spring 2104 in a tensioned state. It is worth noting that the TCAT anchors 2101 are of an identical design in these figures, only shown in alternate states of compression. FIGS. 23A-24D show the 'angular' version of TCAT anchor 10, where FIGS. 23A-23D display the tension spring 2104 in a relaxed state and FIGS. 24A-24D show tension spring 2104 in a tensioned state. Again, FIGS. 23A-23D and 24A-24D all show TCAT anchor 2310 per the same design, but in alternate states. TCAT anchors 2101 and 2310 are different embodiments, though features (namely, anchor head 2106, barb 2105, and spring 2104) are identical in both formulations.

Figure 26A:
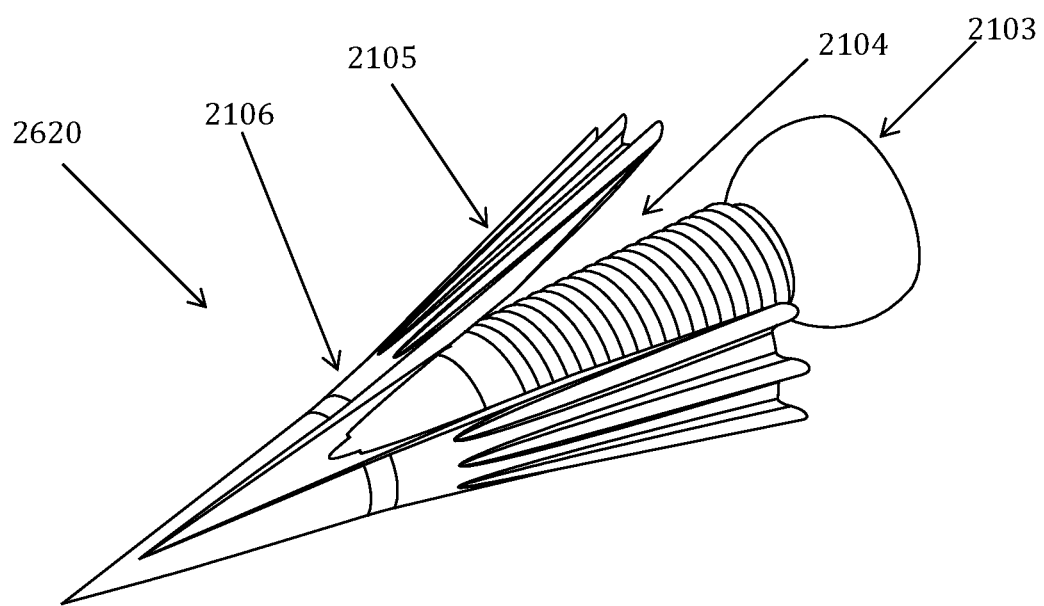
FIG. 26A is a standard depiction of TCAT anchor 2620, in a relaxed state, that highlights anchor head 2106, barbs 2105, tension spring 2104 and anchor cap swivel 2103.
Figure 26B:
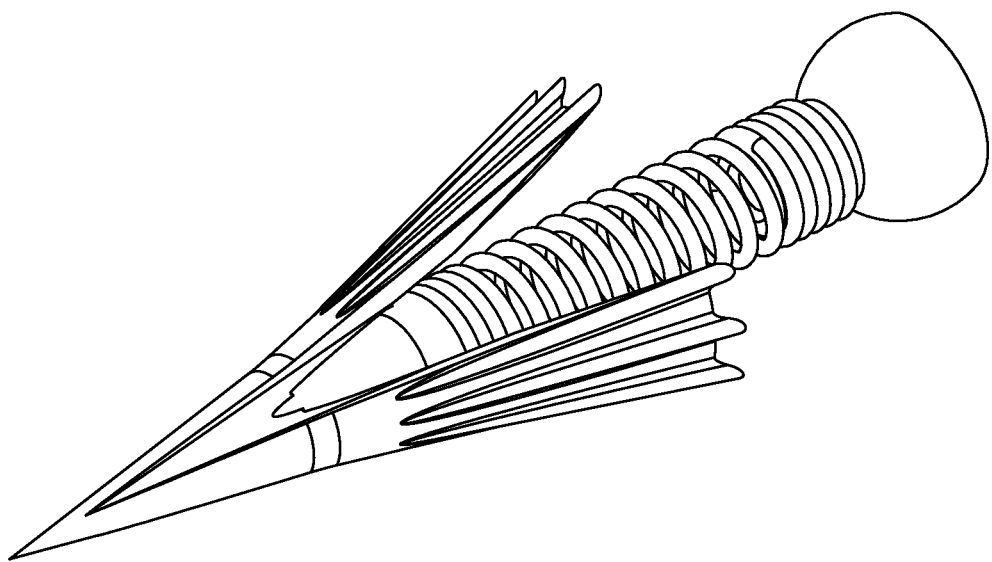
FIG. 26B illustrates TCAT anchor 2620 from FIG. 26A in a tensioned state.
Figure 27A:
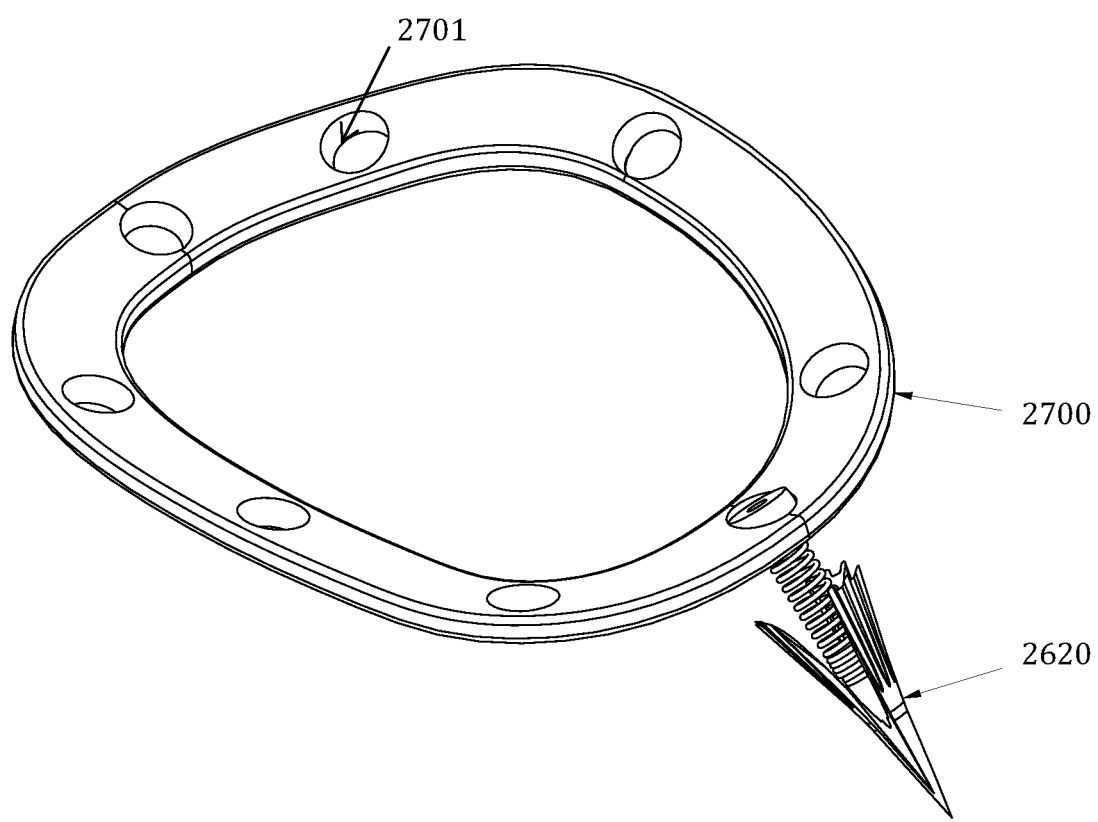
FIG. 27A is a drawing of prosthesis 2700, with eyelets 2701, and featuring a single TCAT anchor 2620 in its tensioned state.
Figure 27B:
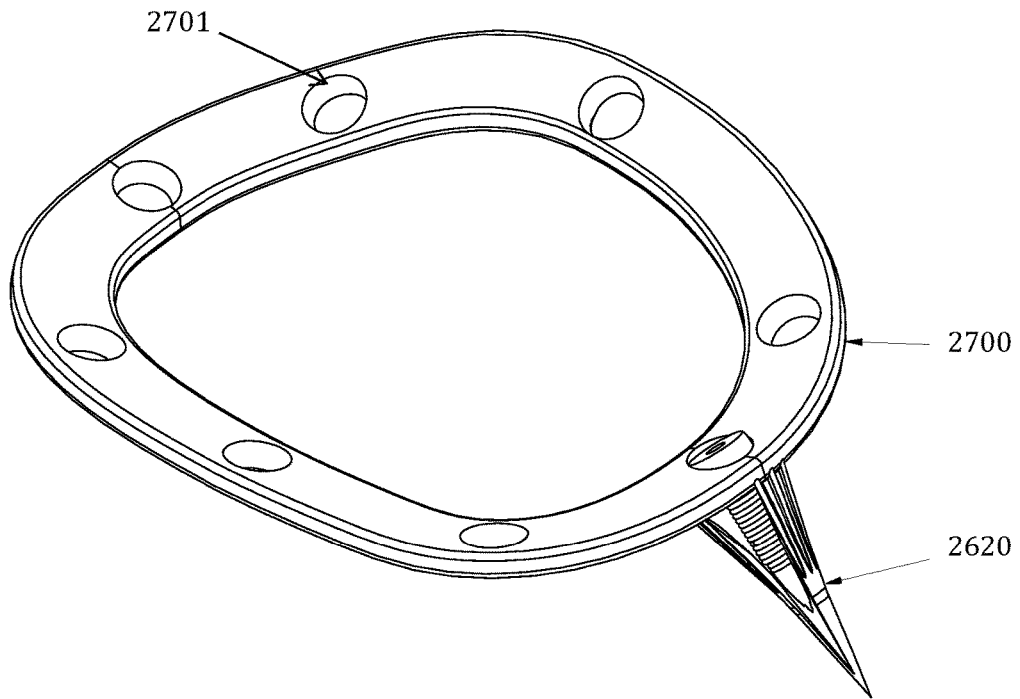
FIG. 27B shows prosthesis 2700, having eyelets 2701, where a single TCAT anchor 2620 is in its relaxed state.
Figure 27C:
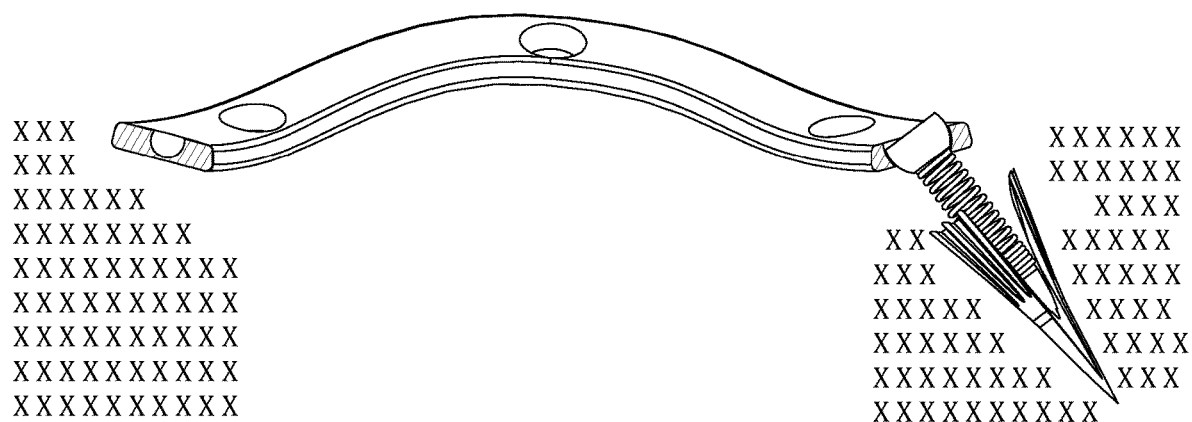
FIG. 27C is a cross-sectional view of FIG. 27 A. X's have been used to denote areas of tissue, as though the prosthesis 2700 where being used in a mitral valve replacement surgery.

FIGS. 26A and 26B offer a third embodiment of the TCAT anchor 2620, in its compressed and tensioned states, respectively, referred to as the 'ball-head' formulation hereafter, such that proper utilization would require its being used in tandem with prosthesis 2700 in FIGS. 27A-27C. This version differs only slightly from the 'ball and socket' formulation in that the TCAT anchor 2620 lacks anchor cap 2102, as in FIGS. 21A-21D and 22A-22D. Prosthesis 2700 features eyelet 2701, which is designed to receive TCAT anchor 2620 such that anchor cap swivel 2103 will fit securely within the eyelet at any number of various angles of deployment. Per this embodiment, the force exerted by tension spring 2104 after deployment will serve to hold anchor cap swivel 2103 firmly within the eyelet 2701 of the prosthesis.

The TCAT anchors 2101 or 2310 may be manufactured as four individually molded components that may be assembled together to form one individual TCAT anchor. These components may be molded from polypropylene, or some other polymer, in an example embodiment. Though, the tension spring 2104 component may be composed of a metal-based material. As suggested in FIG. 21A, one embodiment of the device could be assembled by simply rotating the proximal end of tension spring 2104 around the threaded, proximal portion of anchor head 2106 and threading the proximal end of tension spring 2104 around the threaded distal portion of anchor cap swivel 2103. In this embodiment, anchor cap 2102 might require, for example, an adhesive or some such alternate means of securement, if a pressure fit between components where not employed. Anchor cap 2102 and anchor cap swivel 2103 might be molded as a single component in a more simplified TCAT anchor formulation. Whereas, this embodiment would require only the force created by the tension of spring's 2104 coil to assure that the four individual components are held firmly together. TCAT anchor 2620 could be manufactured and assembled in the same fashion, though without the anchor cap 2102 component.

Figure 25A:
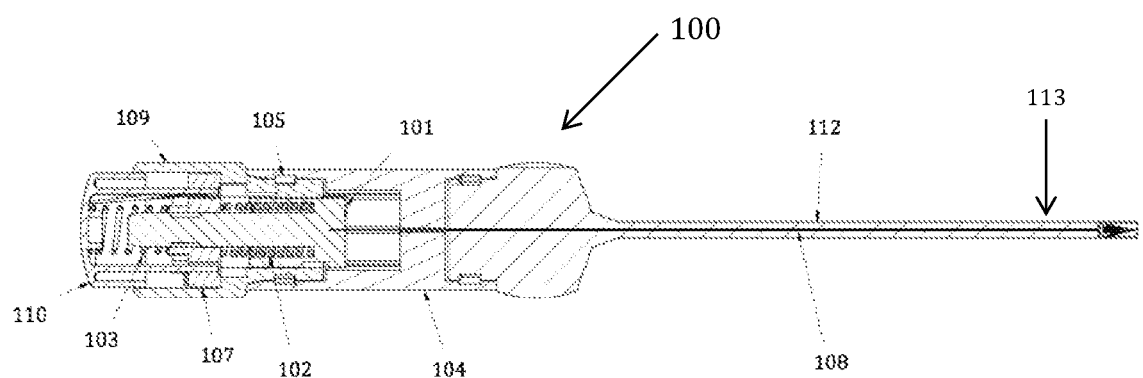
FIG. 25A is a cross-sectional illustration of TCAT deployment mechanism 100, which describes the following components in a clockwise succession: rearm knob 109, knob retention ring 105, cam 101, steerable catheter 112, torquable catheter head 113, pusher wire 108, handle 104, deployment compression spring 102, latch base 107, release button compression spring 103, and release button 110.
Figure 25B:
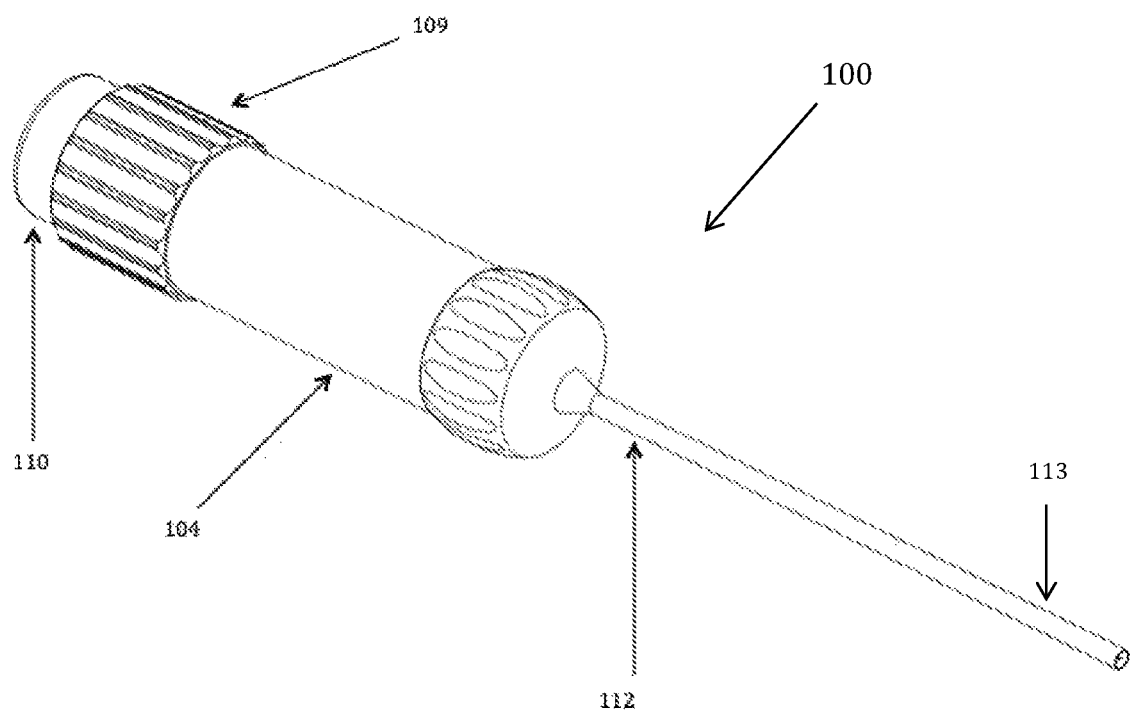
FIG. 25B is a conventional depiction of TCAT deployment mechanism 100. Only rearm knob 109, steerable catheter assembly 112, torquable catheter head 113, handle 104, and release button 110 are visible in this illustration.
Figure 25C:
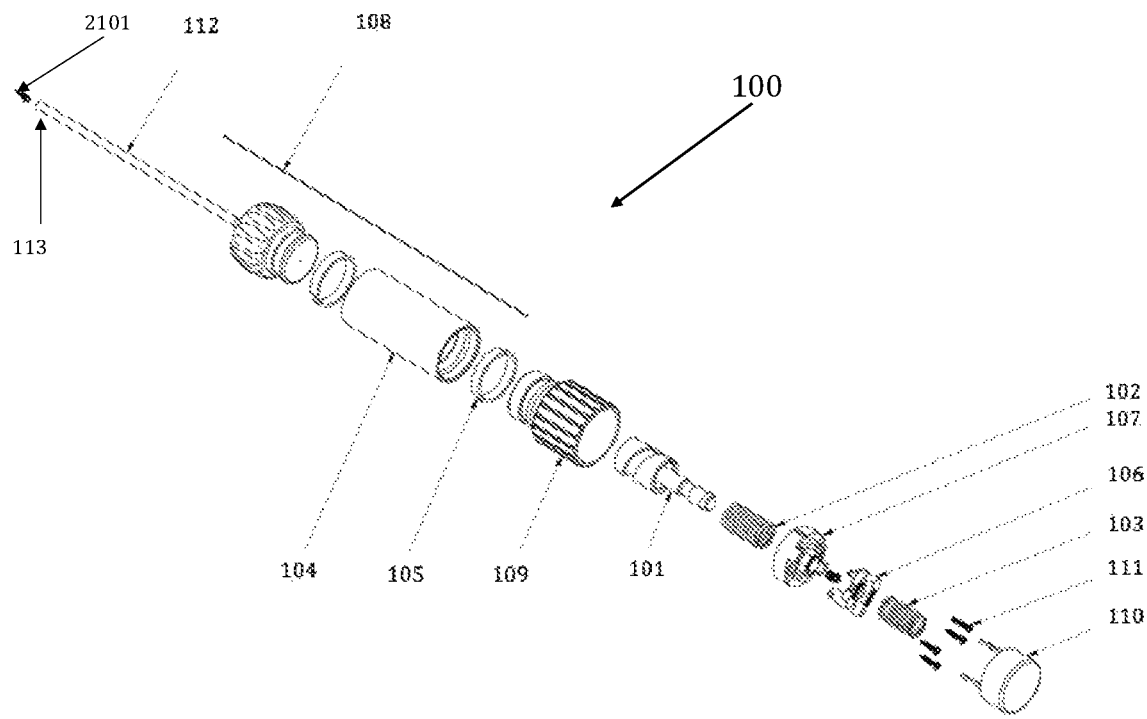
FIG. 25C is a component specific rendering of TCAT deployment mechanism 100 prior to assembly, where the following components are labeled numerically: TCAT anchor 2101, steerable catheter assembly 112, pusher wire 108, deployment compression spring 102, latch base 107, latch 106, release button compression spring 103, screws 111, release button 110, cam 101, rearm knob 109, knob retention ring 105, handle 104, and torquable catheter head 113.

TCAT deployment mechanism 100, as described in FIGS. 25A-25C, could be similarly constructed as is alluded to in the component specific depiction of FIG. 25C. Again, the components may be molded from polymer materials or stainless steel in the case of the spring and screw components. The knob retention rings 105 at either end of the handle 104 are partially collapsible to allow them to be secured in place on the distal end of the steerable catheter assembly 112 and the proximal end of the rearm knob 109. The knob retention rings 105 then require some inward pressure in order to partially collapse and be inserted within handle 104, where once in place, and lacking inward force, they would expand into a corresponding groove on the interior of handle 104. Once expanded, they would ensure that the handle 104 remain firmly attached to steerable catheter assembly 112 and rearm knob 109. Most of the components could be assembled similarly, where a corresponding latch within the interior of rearm knob 109 twists into the locking groove on the exterior of cam 101's proximal end. Similar locking mechanisms could serve to connect cam 101 to latch base 107 as well as latch base 107 to release button 110. In this embodiment, screws 111 would be required to secure latch 106 to latch base 107, but otherwise, self-securing components could be the primary means of assembling the device, as previously described.

Figure 21A:
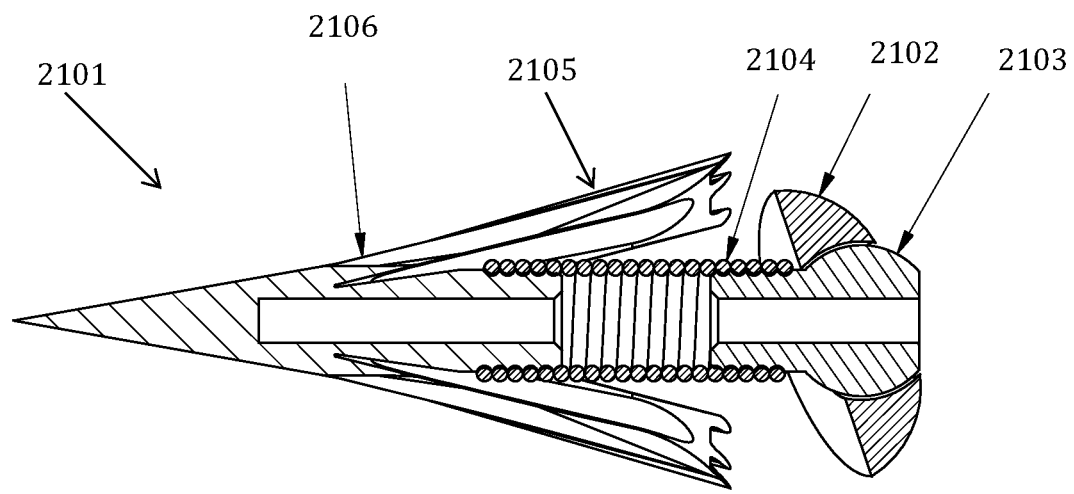
FIG. 21A is a cross-sectional illustration of the 'ball and socket embodiment' of a TCAT anchor 2101, in its relaxed state, which demonstrates components: anchor cap 2102, anchor cap swivel 2103, tension spring 2104, and anchor head 2106. An individual barb 2105 is also denoted.
Figure 21B:
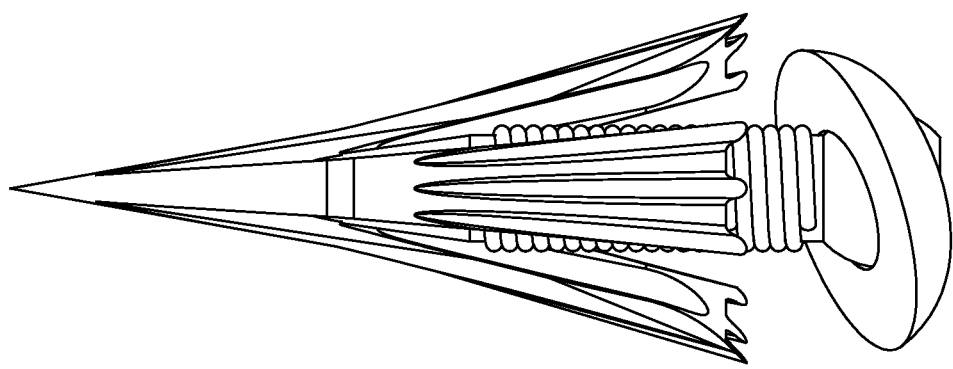
FIG. 21B is a non-sectional illustration of the same embodiment of FIG. 21A.
Figure 21C:
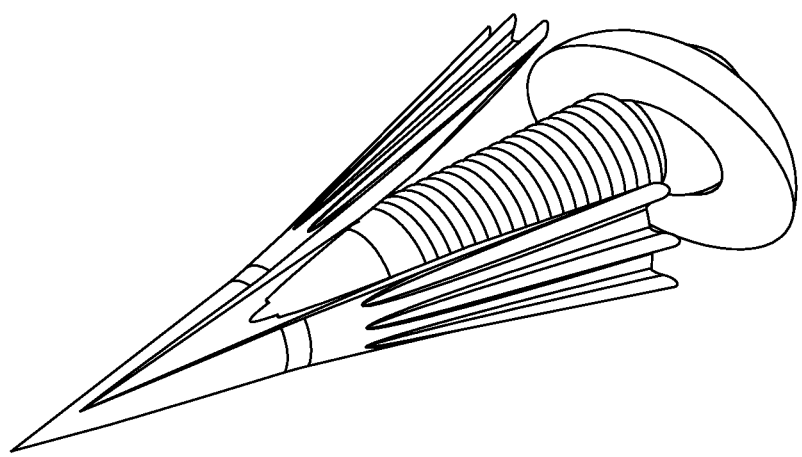
FIG. 21C is an isometric illustration of FIG. 21A.
Figure 21D:
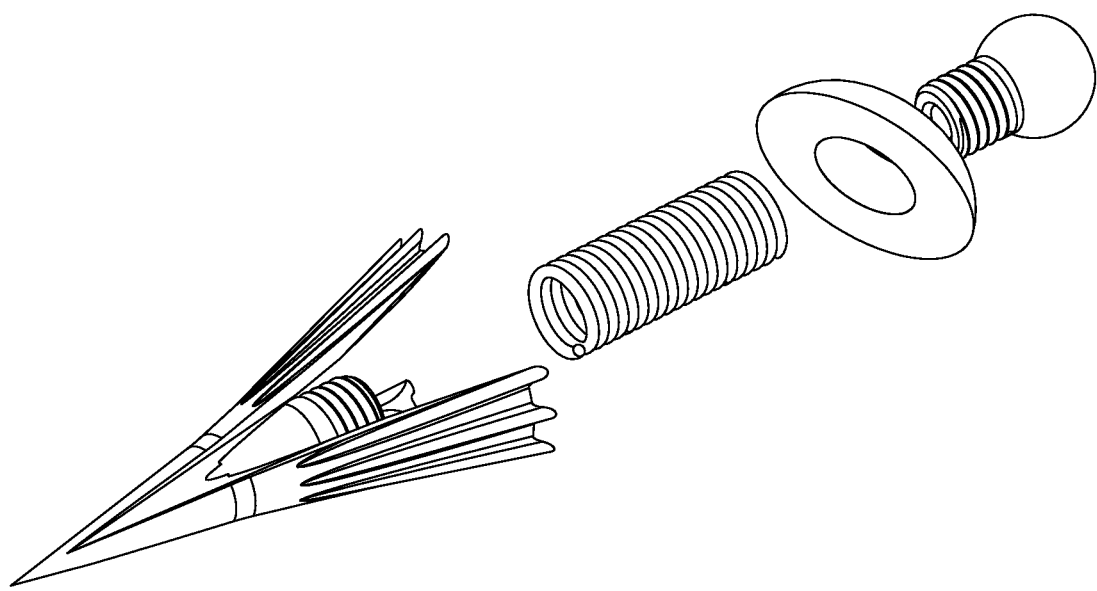
FIG. 21D is an exploded view of the 'ball and socket embodiment' illustrating the components of TCAT anchor 2101 individually, as though prior to assembly.
Figure 22A:
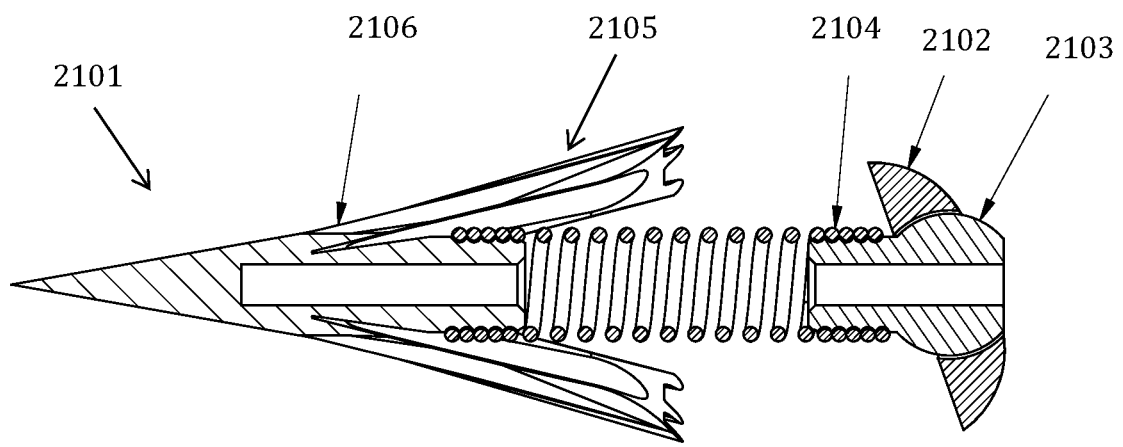
FIG. 22A is a cross-sectional illustration of the 'ball and socket embodiment' of TCAT anchor 2101, in its tensioned state, which demonstrates components: anchor cap 2102, anchor cap swivel 2103, tension spring 2104, three barbs 2105, and anchor head 2106.
Figure 22B:
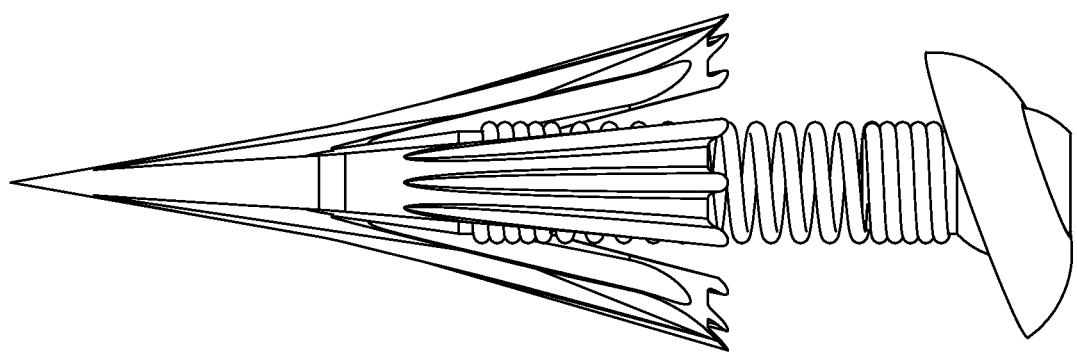
FIG. 22B is an illustration of TCAT anchor 2101 per the same embodiment and tensioned state as FIG. 22A.
Figure 22C:
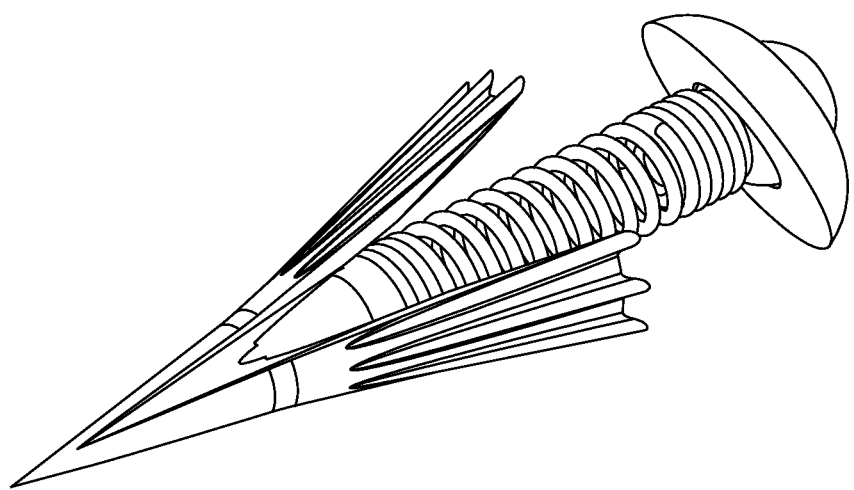
FIG. 22C is an isometric illustration of FIG. 22 A.
Figure 22D:
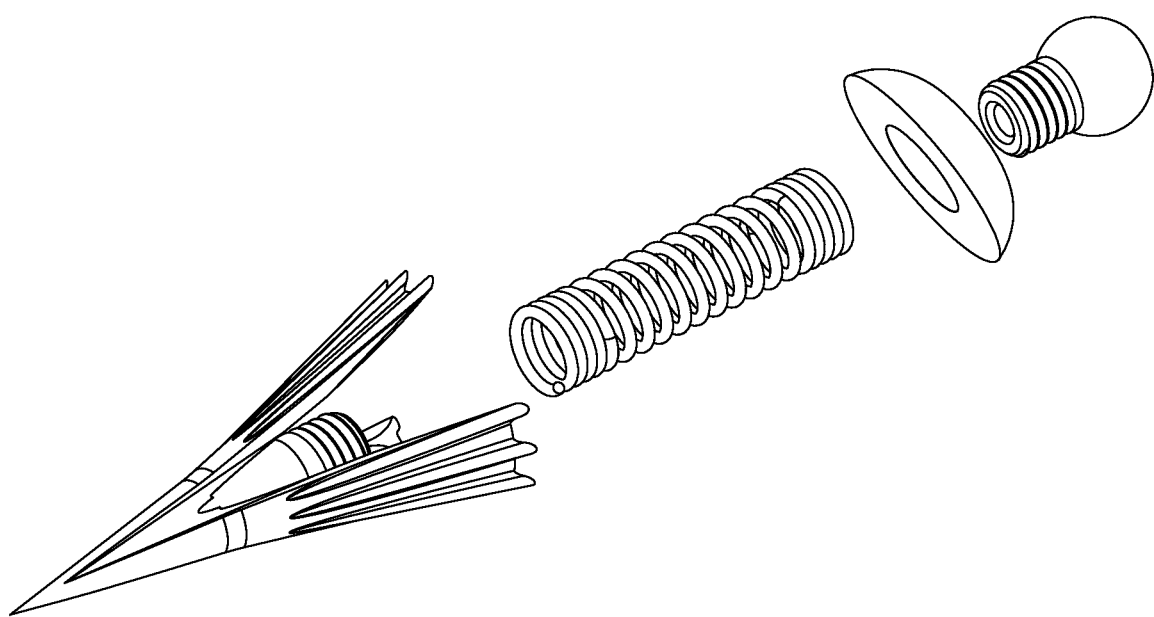
FIG. 22D is an exploded view of FIG. 22A.
Figure 23A:
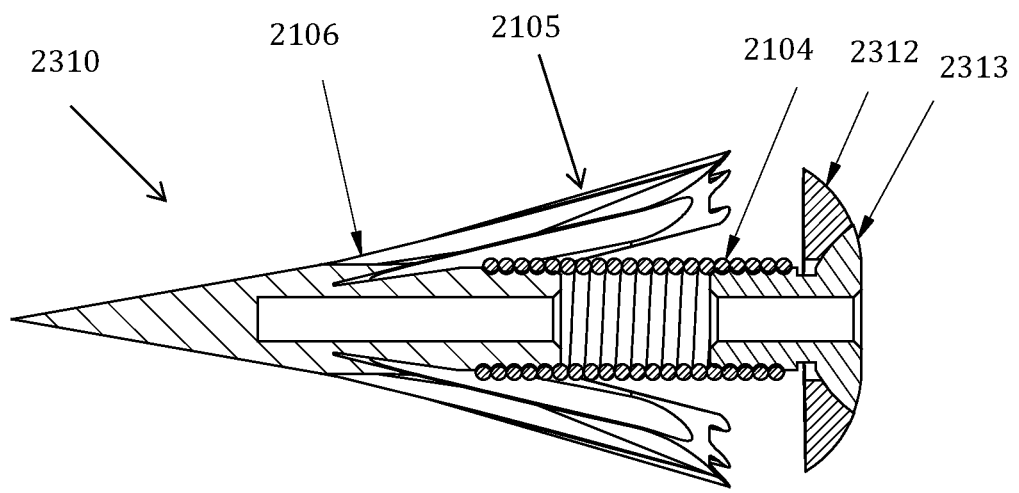
FIG. 23A is a cross-sectional depiction of the 'angular' embodiment of TCAT anchor 2310 in its relaxed position, with components anchor head 2106, anchor cap 2312, anchor cap swivel 2313, tension spring 2104 and barbs 2105 labeled.
Figure 23B:
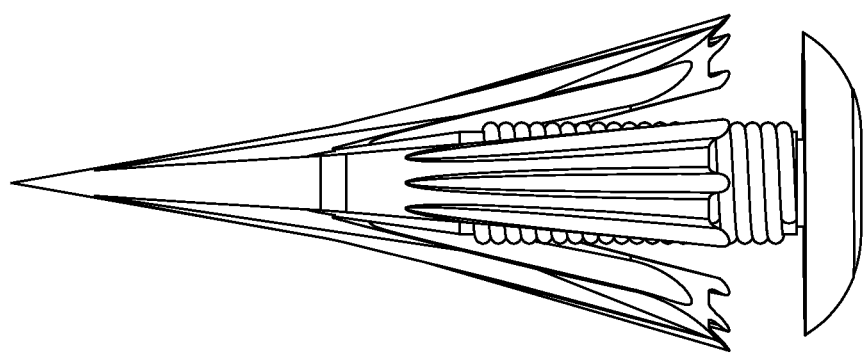
FIG. 23B is a conventional demonstration of the same embodiment described in FIG. 23A.
Figure 23C:
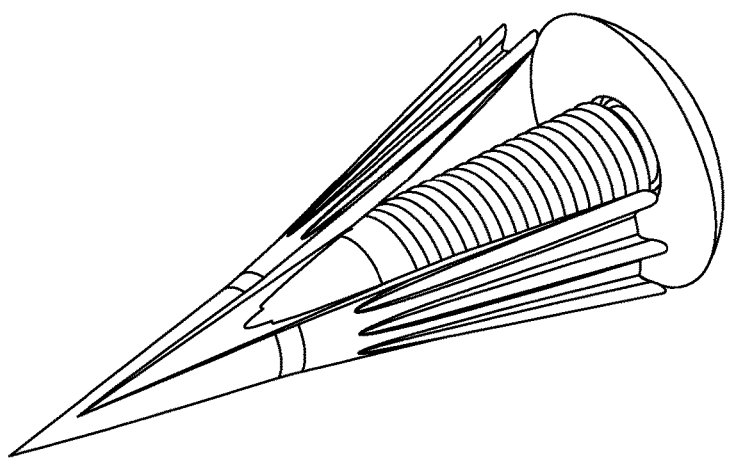
FIG. 23C is an isometric depiction of TCAT anchor 2310, as show in FIG. 23A.
Figure 23D:
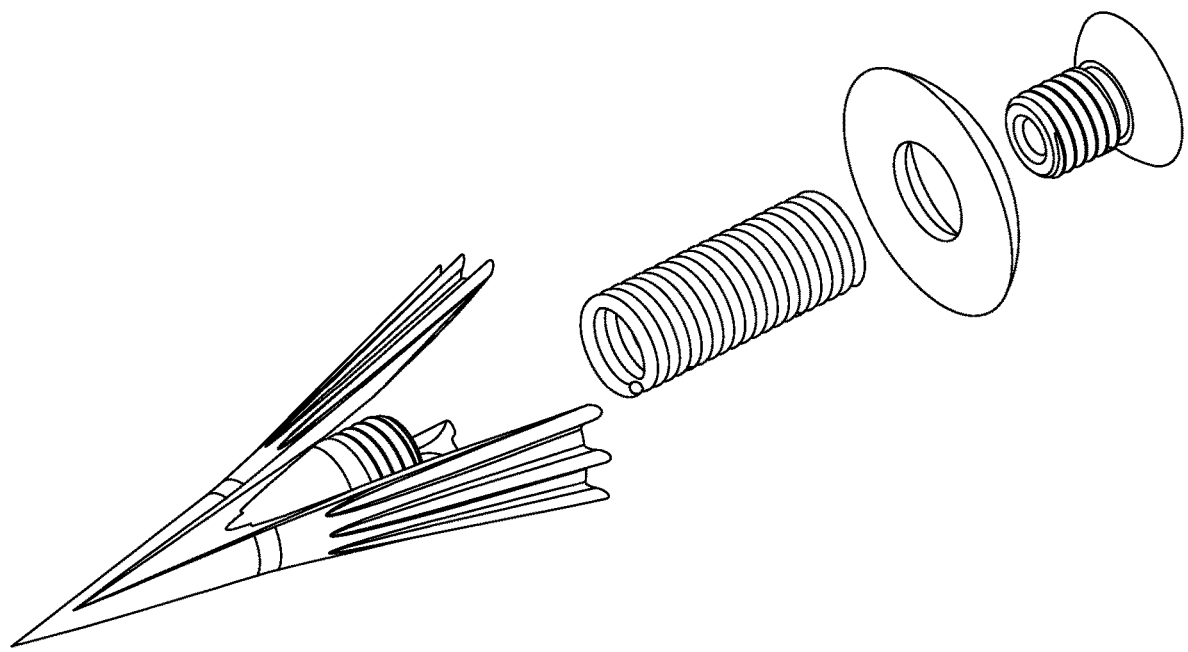
FIG. 23D illustrates TCAT anchor 2310 components individually, with tension spring 2104 in a relaxed state.
Figure 24A:
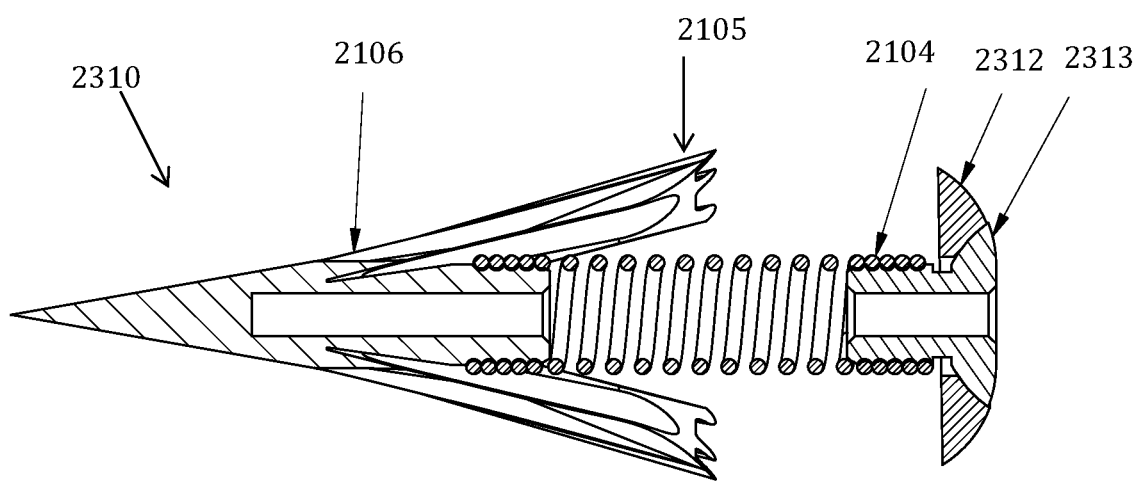
FIG. 24A is a cross-sectional drawing of TCAT anchor 2310, an 'angular' embodiment of the anchor, with tension spring 2104 in a tensioned state, and with anchor head 2106, anchor cap 2312, anchor cap swivel 2313, and barbs 2105 labeled.
Figure 24B:
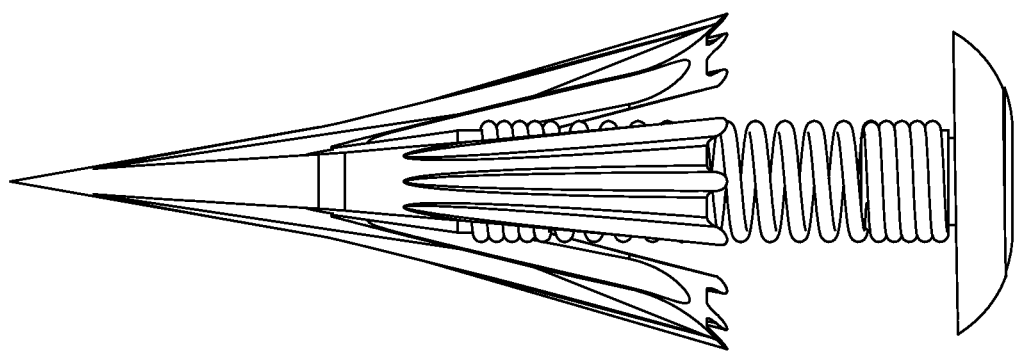
FIG. 24B is the same TCAT anchor 2310 in FIG. 24A demonstrated conventionally.
Figure 24C:
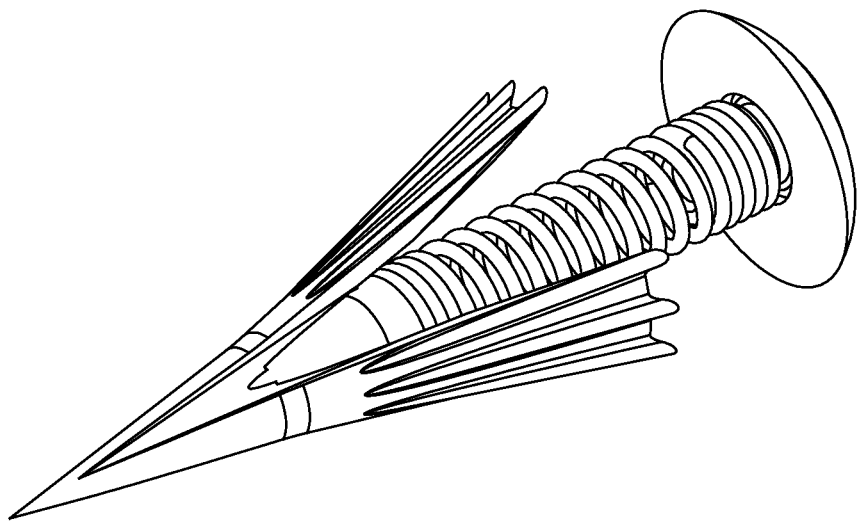
FIG. 24C is an alternate perspective of TCAT anchor 2310 from FIG. 24A.
Figure 24D:
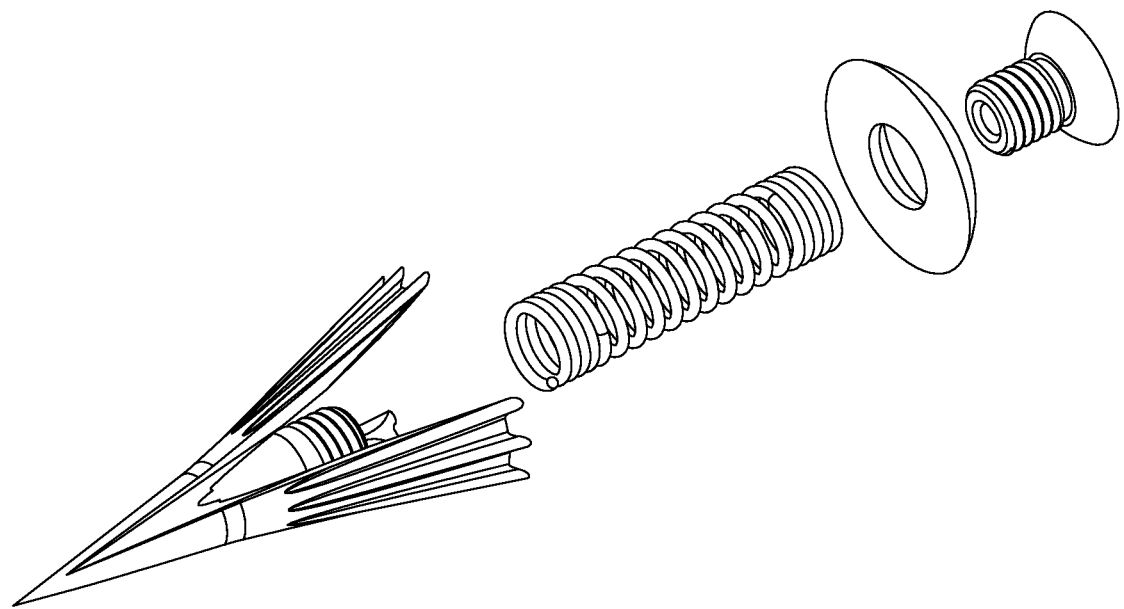
FIG. 24D is an exploded view of FIG. 24A.

The TCAT deployment mechanisms in FIG. 25A, FIG. 28A, and FIG. 29A and the TCAT anchors in FIG. 21A, FIG. 23A, and FIG. 26A are both described below. TCAT deployment mechanism 100 is a flexible embodiment and can be utilized with the 'ball and socket' formulation, the 'angular' formulation, and the 'socket' formulation, respectively. By no means should these particular examples be interpreted as conceptually exhaustive, but rather, any combination or rearrangement of the material contained in these examples should be considered as having been disclosed.

Accordingly, the embodiment of TCAT deployment mechanism 100, demonstrated in FIGS. 25A, B & C, may be utilized to affix a prosthesis securely to the tissues of the human heart, by means of TCAT anchors 2101. Once a prosthesis has been placed appropriately within the heart, the TCAT deployment mechanism 100 may approach the sight transeptally, transfemorally, or otherwise depending on the circumstances. The deployment mechanism 100 features a low profile, steerable catheter 112, this instantiation measures 12 French in diameter, which can be utilized to effectively navigate to the site of the prosthesis.

This catheter 112 may be steered through artery, vein, or incision in order to bring the TCAT anchor 2101 into alignment with a prosthesis, which may feature a receptive anchoring site, and once aligned the TCAT deployment mechanism 100 is fired by means of release button 110. In this formulation, pushing release button 110 triggers the rapid decompression of the deployment compression spring 102, by means of release button compression spring 103 transitioning that force onto latch 106, which thereby releases deployment compression spring 102 from its compressed state. The force exerted by compression spring 102's rapid expansion acts on cam 101, which in turn drives pusher wire 108 in a proximal direction that maintains the current curvature of the catheter 112, yet delivers said driving force to TCAT anchor 2101 at the firing site.

As illustrated in FIG. 21A, this version of the TCAT anchor 2101 features anchor 2101, anchor cap 2102, and anchor cap swivel 2103 with aligned, hollow segments that are designed to house pusher wire 108 prior to deployment. Tension spring 2104, in FIG. 21A, is also hollow by nature of being a spring, and so can be threaded by pusher wire 108 despite not necessarily having an internal tube of the same diameter. The firing process terminates once the pusher wire 108 has delivered its distal, driving force onto the TCAT anchor 2101. After the distally directed force of the pusher wire 108 has driven TCAT anchor 2101 to its desired depth, the pusher wire 108 is withdrawn from the TCAT anchor 2101, and the tension spring 2104 pulls anchor 2101 in a proximal direction, such that an opposing force is applied to the anchor cap 2102 and anchor cap swivel 2103 in a distal direction. The result of these opposing forces is two-fold: the retraction of anchor 2101 forces its barbs 2105 to set firmly within the soft tissues of the heart, whilst anchor cap 2102 and anchor cap swivel 2103 are pulled flush with the prosthesis, i.e. assuring a non-obstructing position within the prosthesis's interior profile.

The TCAT deployment mechanism 100 may be used to fire as many TCAT anchors 2101 as is necessary to best secure the prosthesis being implanted. In this embodiment, the TCAT deployment mechanism 100 can be prepared for successive firings by means of simply reloading an anchor and recoiling the deployment compression spring 102. The device is 'rearmed' by turning rearm knob 109, that circular motion turns the internally attached cam 101. Cam 101's circular motion forces the deployment compression spring back into a compressed state by means of its angled exterior grooves forcing the cam 101 portion of the device to move distally away from rearm knob 109. This design ensures that after the deployment of one TCAT anchor 2101, the TCAT deployment mechanism simply requires a new TCAT anchor 2101 to be reloaded and the rearm knob 109 to be twisted several times to ready the device for a second deployment.

Two alternate embodiments of the TCAT deployment mechanism, 2800 and 2900, which are featured in FIGS. 28A-28C and FIGS. 29A-29C, respectively, make use of the same firing sequence described above to fire multiple TCAT anchors 2620 whilst the prosthesis 2700 is held in place. These embodiments may be used in a transeptal procedure, and would serve to eliminate certain variables in the anchoring process. A primary benefit of these articulations, TCAT deployment mechanism 2800 and 2900, is that the prosthesis could be set in place, held and anchored by means of one device. That is, as described in FIG. 28C, TCAT deployment mechanism 2800 would employ prosthetic grips 2803 on prosthetic holder 2802 so as to hold the prosthesis 2700 firmly in place prior to and during anchor deployment. This will better ensure that the prosthesis 2700 remains at the target location throughout the deployment process, which may consist of any sequence of individual or plural anchor deployments.

Furthermore, this design may serve to overcome problems relating to the size discrepancy between the mitral valve and the prosthesis 2700 being implanted. It is common for the body of operable patients requiring a mitral valve replacement, for example, for the mitral valve to have relaxed outward, or expanded in size. It is, in fact, one of the primary reasons that surgical intervention is required; the mitral valve prosthesis may be needed to bring the valve back to its ideal size and structure. This has been known to create a problem for anchoring technologies, when anchors are fired individually, as the first anchoring will bring the prosthesis into apposition with one edge of the valve, while necessarily pulling it further from its opposite anchoring site. However, TCAT deployment mechanism 2800 circumvents this dilemma by firing TCAT anchors into the prosthesis while it is still held by the deployment mechanism, as in the FIG. 29 embodiment. This feature allows for the surgeon to fire TCAT anchor 2620 into one wall of the mitral valve, yet maintain a grip on the prosthesis via release latch 2905, in order to pull the prosthesis into apposition with the opposite wall before deploying a second TCAT anchor 2620. The repetition of this method would allow for each of the anchors to be fired while the prosthesis is held in apposition with the surrounding tissues and without the aid of a secondary device for holding or positioning the prosthesis.

Figure 28A:
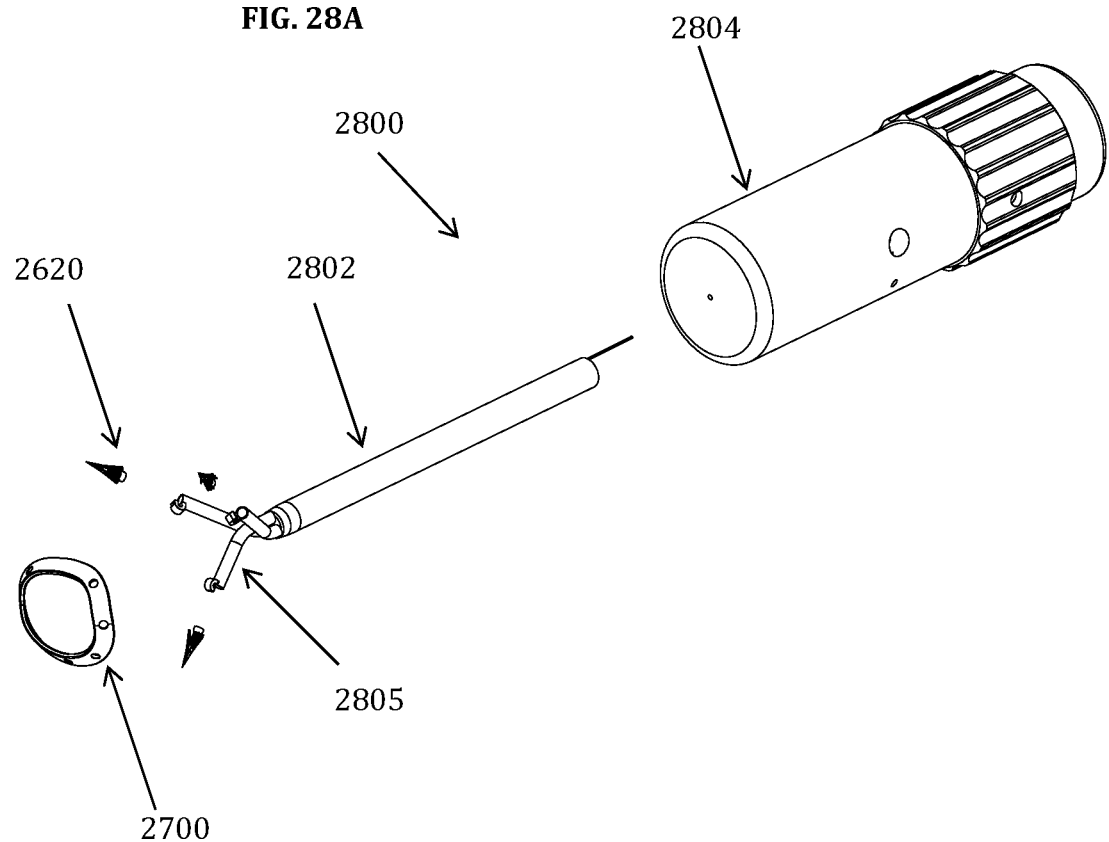
FIG. 28A is a component-specific, 'blown-out' view of the TCAT deployment mechanism 2800, the 'tri-anchor' embodiment, and prosthesis 2700, with TCAT anchors 2620, deployment arms 2805, prosthesis holder 2802, and handle 2804 described.
Figure 28B:
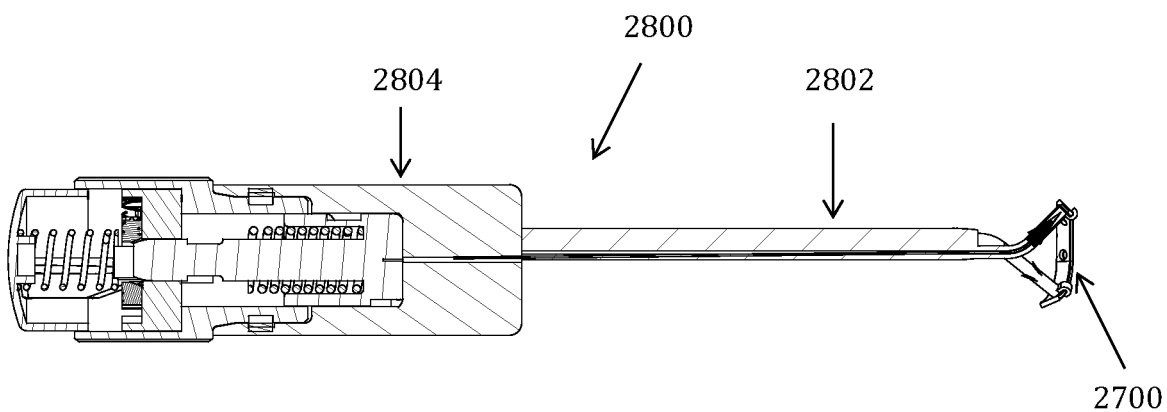
FIG. 28B is a cross-sectional depiction of FIG. 28A.
Figure 28C:
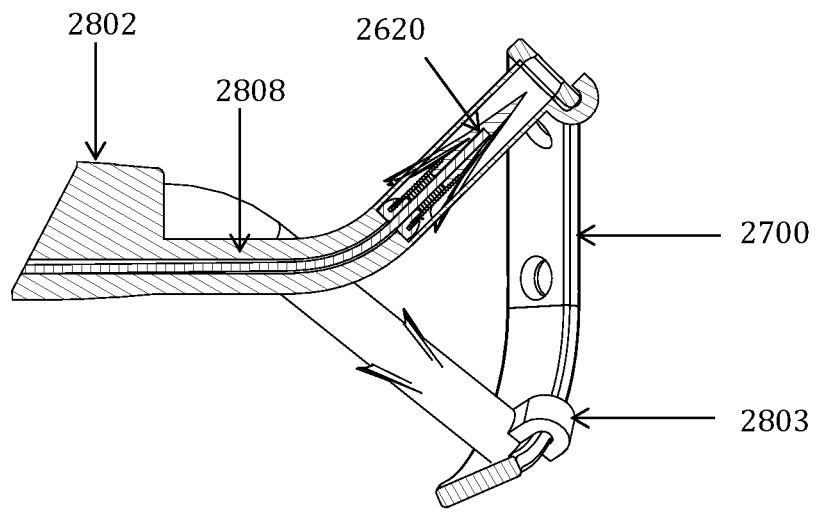
FIG. 28C shows a close-up, cross-sectional illustration of the proximal end of TCAT deployment mechanism 2800 holding prosthesis 2700. TCAT anchor 2620, prosthesis holder 2802, prosthesis grips 2803, and pusher wire 2808 are each denoted.
Figure 29A:
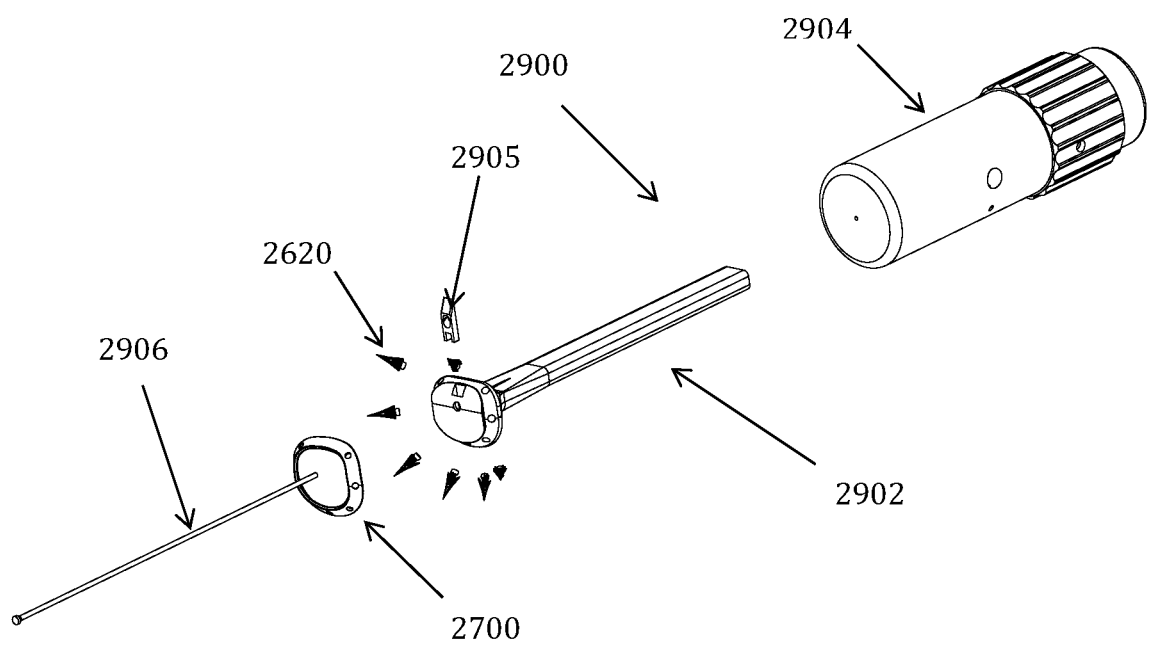
FIG. 29A illustrates the 'septi-anchor' embodiment of TCAT deployment mechanism 2900 in a 'blown-out' format. The following are each identified: release rod 2906, prosthesis 2700, TCAT anchor 2620, release latch 2905, prosthesis holder 2902, and handle 2904.
Figure 29B:
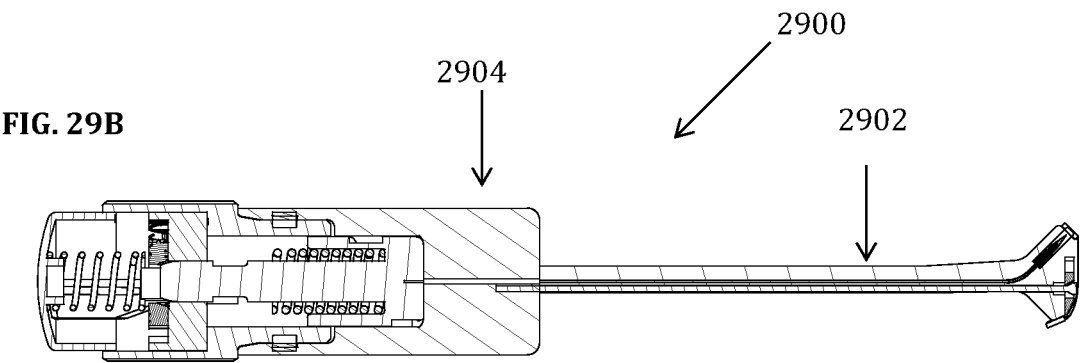
FIG. 29B is a cross-sectional version of FIG. 29A.
Figure 29C:
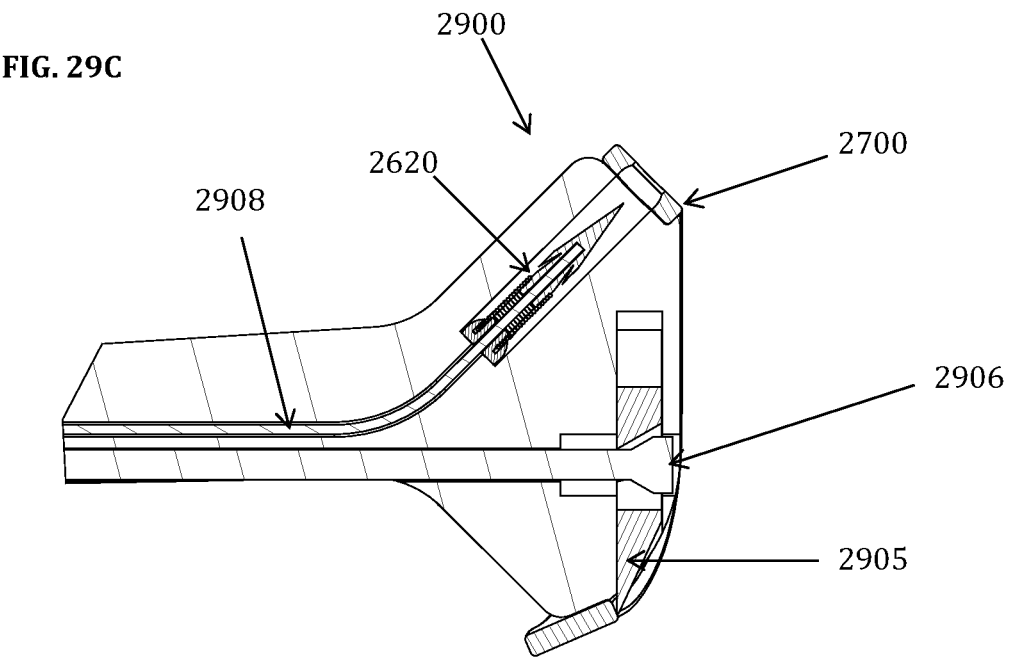
FIG. 29C is a close-up, cross-sectional view of the proximal end of TCAT deployment mechanism 2900 engaging prosthesis 2700. Pusher wire 2908, TCAT anchor 2620, release rod 2906, and release latch 2905 are numbered.

The initial firing sequence described for the TCAT deployment mechanism 100 might be similar in the embodiments described in FIGS. 28A-28C and FIGS. 29A-29C up until the point at which the proximal force is transitioned onto the pusher wire 108. The force applied to the pusher wire 108 may be transferred onto one or more individual pusher wire branches 2808 within prosthetic holder 2802 for example. Each of those pusher wires 2808 terminates within the receptacle cylinder within TCAT anchors 2620, much like previously described embodiments, yet with each anchor housed in one of a multitude of deployment arms 2805, where FIG. 28A shows three. The deployment arms 2805 may be angled so as to enact a deployment force at opposing angulations in order to best secure the prosthesis after the first deployment, thereby overcoming the deployment difficulties previously described. The firing sequence may also be amended so as to deploy any number of anchors at a time and to deploy those anchors at any of a wide range of angulations.

Figure 30A:
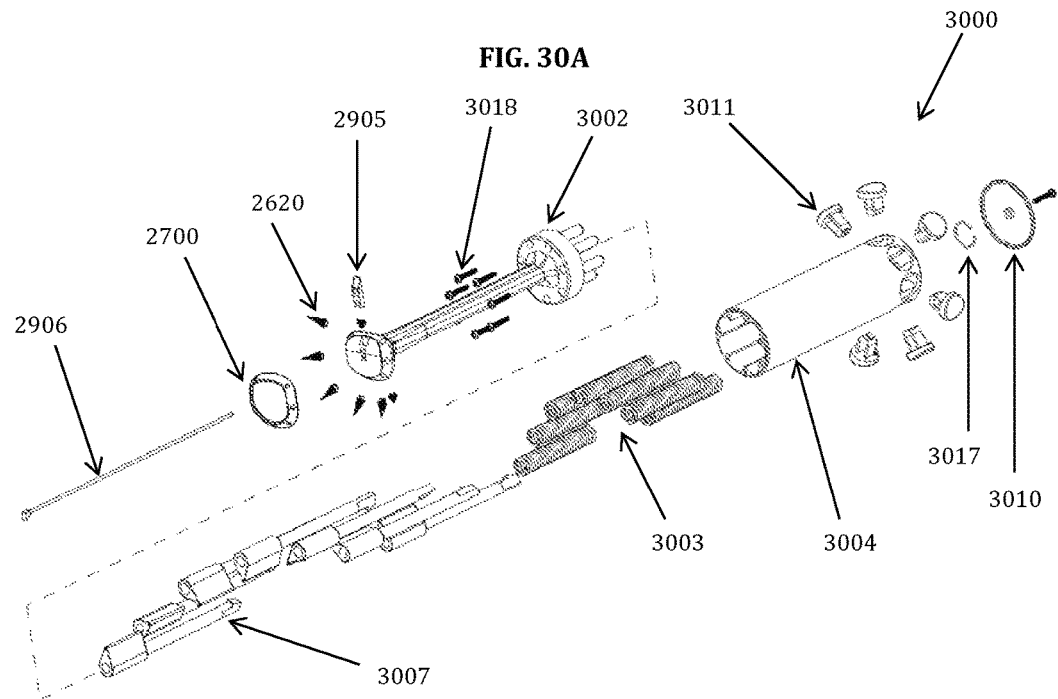
FIG. 30A is a component-specific illustration of the 'pre-armed' TCAT deployment mechanism 3000, shown as though prior to assembly.
Figure 30B:
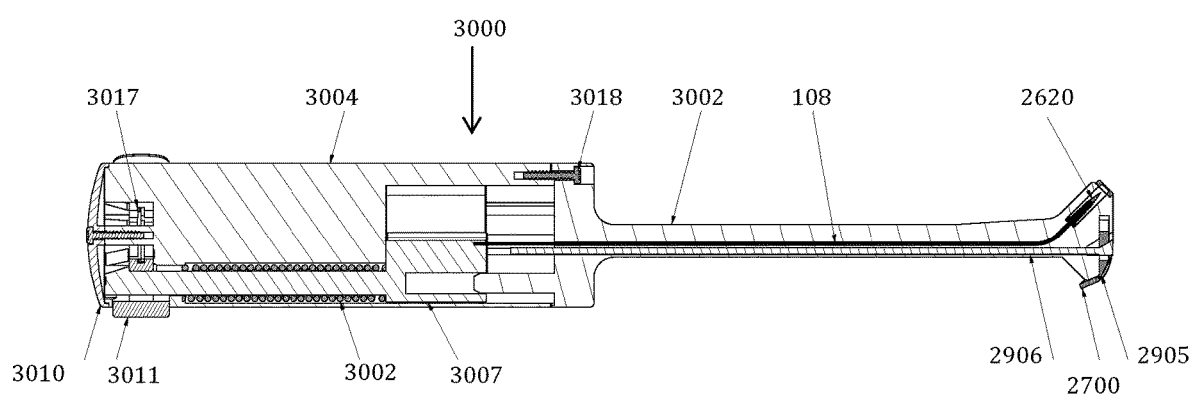
FIG. 30B is a cross-sectional rendering of the device from FIG. 30A.
Figure 30C:
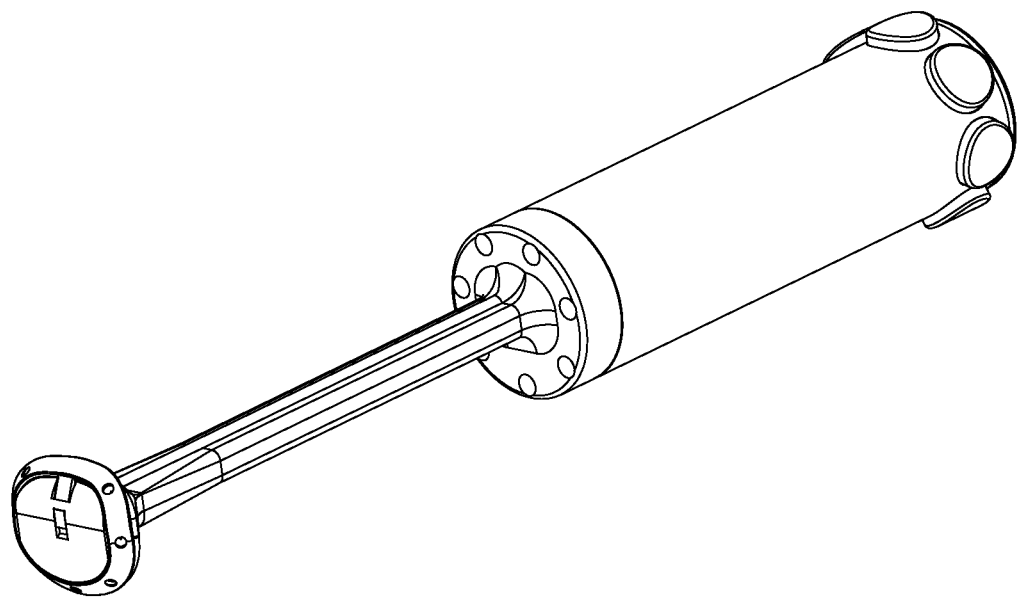
FIG. 30C is an alternate view of FIG. 30A.
Figure 30D:
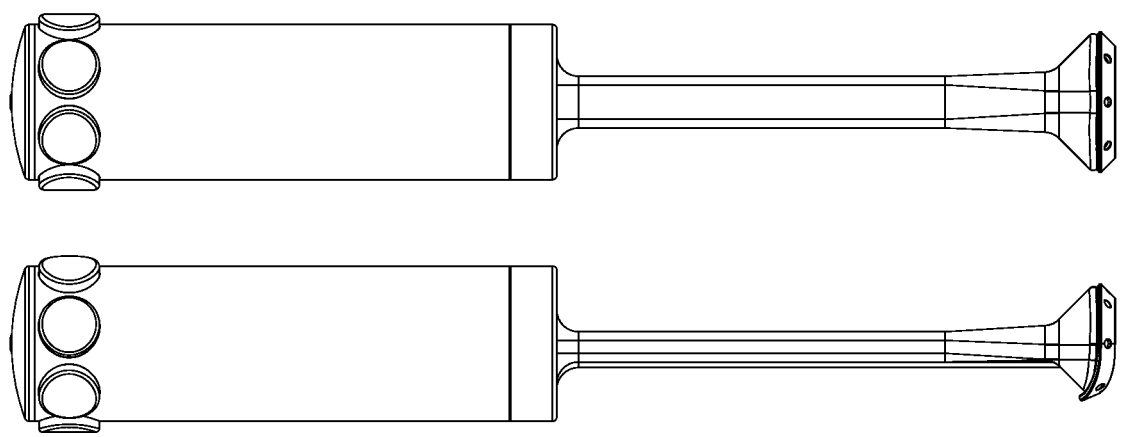
FIG. 30D offers two different view of the same embodiment in FIG. 30A.
Figure 31A:
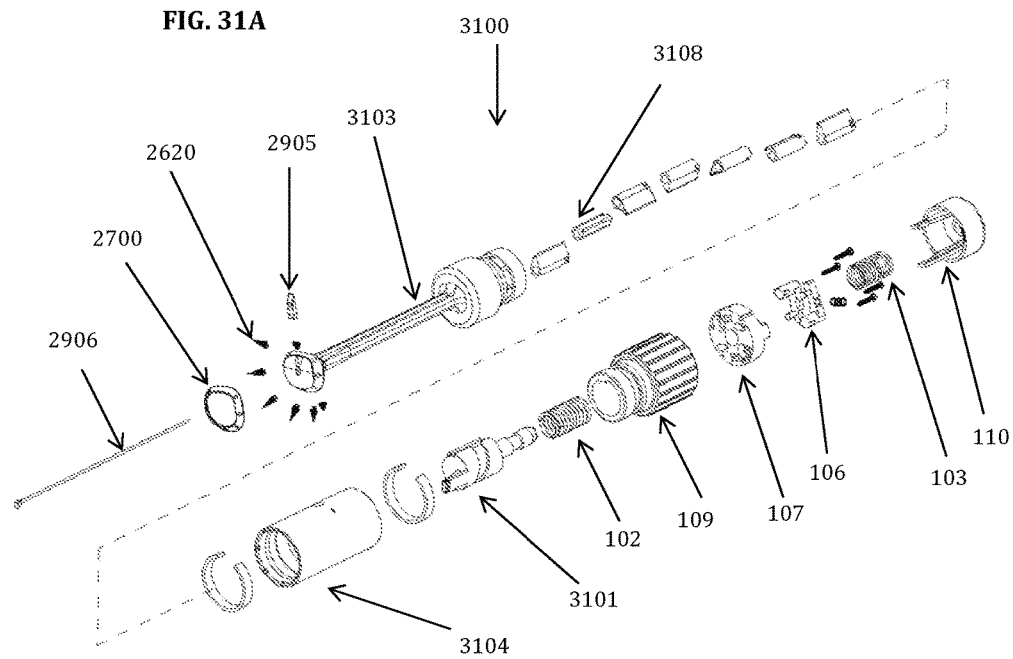
FIG. 31A is a component-specific illustration of the 're-armable' TCAT deployment mechanism 3100, shown as though prior to assembly.
Figure 31B:
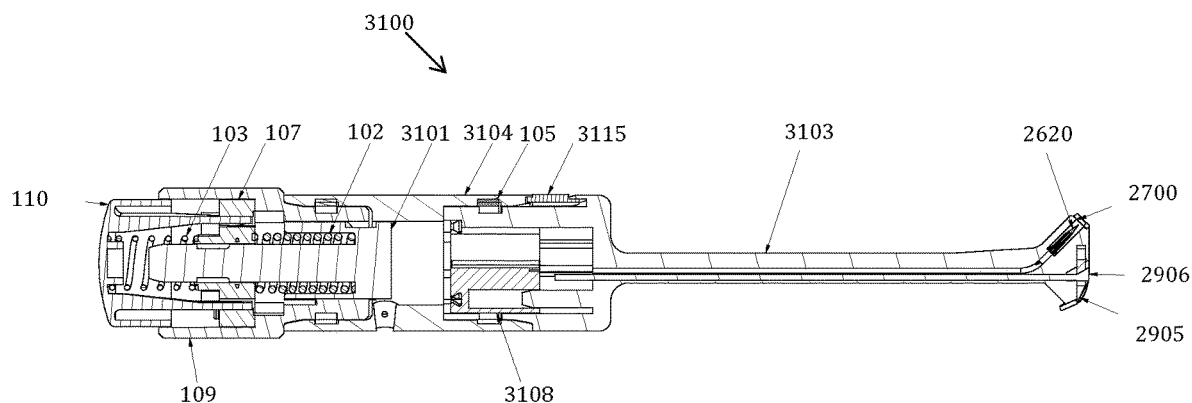
FIG. 31B is a cross-sectional drawing of the device in FIG. 31A.
Figure 31C:
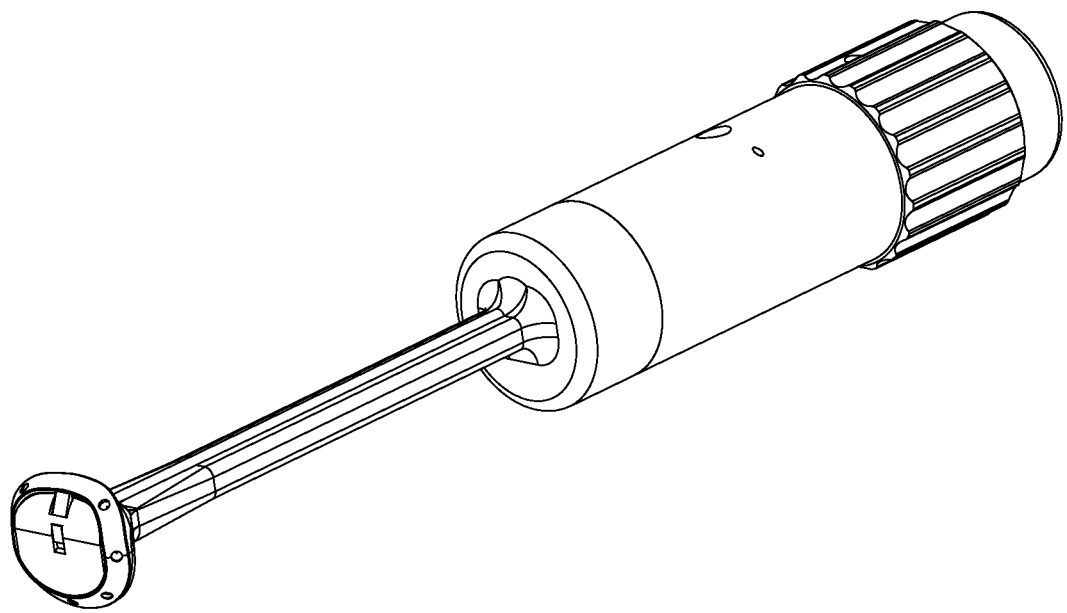
FIG. 31C is a standard depiction of the device in FIG. 31A.
Figure 31D:
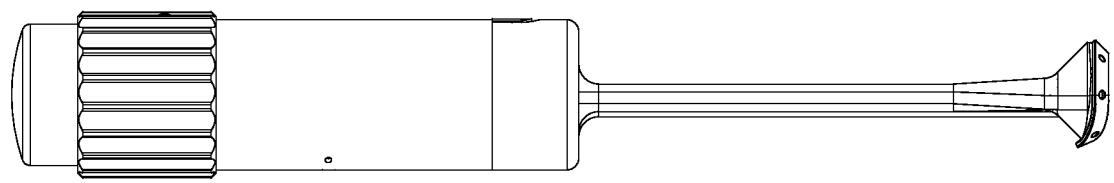
FIG. 31D is an illustration of the device in FIG. 31A, from an alternate viewpoint.

The TCAT deployment mechanism 3000 is depicted in FIGS. 30A-30D, per a 'pre-armed' embodiment of the device. In accordance with the illustrations of this particular design, deployment mechanism 3000 would not require a rearm knob 109 to compress deployment compression spring 102 between anchor deployments. Instead, handle 3004 could be assembled such that individual deployment compression springs 3003 would be housed in contact with pushers 3007, such that each individual deployment compression spring 3002 could be released, by means of buttons 3011, and fire the various anchors in whatever sequence necessary and without the need to rearm the device between firings. The rest of the components on the 'pre-armed' device might look similar those depicted in FIGS. 29A-29D of the 'septi-anchor' embodiment. That is, prosthesis 2700 might still be secured by means of release latch 2905 and release rod 2906, and prosthesis holder 3002 could, similarly to prosthesis holder 2902, house a plurality of pusher wires 2908 and corresponding TCAT anchors 2620 prior to deployment. The prosthesis holder 3002 may differ from prior variations in that its distal end might be designed to receive a plurality of pushers 3007 and transition their deployment force onto internal pusher wires 108. FIG. 30A shows a configuration, which utilizes screws 3018 to secure prosthetic holder 3002 to handle 3004. The 'pre-armed' exemplary embodiment described above could serve to cut down on surgical times by allowing the surgeon to house all TCAT anchors 2620 in the same device and not require him or her to rearm the device between each employment.

TCAT deployment mechanism 3100 is illustrated from various perspectives in FIGS. 31A-31D, and while it is itself an alternate formulation of the technology, it can be considered as a variation of the 'septi-anchor' deployment mechanism 2900 from FIGS. 29A-29D. As was the case in those Figures, the 're-armable' embodiment shown in FIGS. 31A-31D also entails seven TCAT anchors 2620, though any plurality of anchors might be utilized. The 're-armable' TCAT deployment mechanism 3100 has a similar initial firing sequence to TCAT deployment mechanism 100, up to the point at which deployment compression spring 102 transfers its force onto cam 3101. Cam 3101, here, may be designed to deliver the force from deployment compression spring 102 onto one of a plurality of pushers 3108, seven pushers 3108 per FIG. 31A. Those pushers 3108 could be aligned with each of the corresponding pusher wires 2908 housed in the prosthetic holder 3103, and the firing sequence would again be consistent with the deployment mechanism 2900 descriptions above. The device might be rearmed by twisting rearm knob 109, as previously described, but is unique from other designs in that it features index latch 3115 in FIG. 31B. Because cam 3101 is keyed rotationally to the interior of the handle 3104, index latch 3115 can be triggered to allow the handle, and accordingly cam 3101, to spin relative to pushers 3108 and prosthetic holder 3103. This feature would allow the user of the device 3100 to select which of the various anchors he or she would like to fire, perhaps by alignment of index latch 3115 with the anchor selected or perhaps by some indicative markings on the handle which might align with markings on the prosthetic holder 3103. After anchor deployment, the device could be rearmed by means of rearm knob 109 and then the handle rotated by means of index latch 3115, in order to select the next TCAT anchor 2620 to be deployed.

FIG. 32A illustrates a frame for a prosthetic valve, which may be a unibody, self-expanding, complaint, transcatheter valve. Frame 3200 includes inflow cells 3210, annular cells 3220, enhanced strength annular cells 3225, leaflet posts or valve struts 3230, anchor receptacles 3240 and tissue engagement members 3250. In an embodiment, frame 3200 illustrates a "flattened" version of the frame that will eventually be deployed with the prosthetic valve. In other words, frame 3200 depicts the frame for the prosthetic valve before it is connected in a cylindrical manner. Once formed cylindrically, the inflow cells 3210 receive the inflow for the prosthetic valve. The annular cells 3220 correspond to the cells of the frame that would receive the outflow from the prosthetic valve. Leaflet posts 3230 are provided to hold the frame 3200 in proper position. Further, in an example embodiment, the leaflet posts 3230 also hold the leaflets, which are connected to a ring of the prosthetic valve, in proper position. The valve leaflets (not shown) are situated against the leaflet posts 3230 such that fluid flowing in a first fluid flow direction urges the leaflets toward each other, closing the valve and preventing the flow of fluid in the first fluid flow direction, and fluid flowing in a second fluid flow direction urges the leaflets away from each other, opening the valve and permitting the flow of fluid in the second fluid flow direction. In an exemplary embodiment, enhanced strength annular cells 3225 are disposed between two of the leaflet posts 3230 of the frame 3200. Further, each leaflet post 3230 is associated with a corresponding anchor receptacle 3240 to affix the frame 3200 and the corresponding prosthetic valve to the surrounding tissue. Tissue engagement members 3250, which are disposed between the annular cells 3220, enhanced strength annular cells 3225 and leaflet posts 3230, are further provided to affix the frame 3200 to the surrounding tissue. In an embodiment, the elements of frame 3200 may contain one or more shape-memory alloys, e.g., nitinol, spring-loaded steel or other alloy or material with appropriate properties. Further, the elements of frame 3200 may be covered in a thin wall of an elastomer (e.g., thermoplastic polyurethane or "TPU"). In another embodiment, the frame 3200 could be utilized without the enhanced strength annular cells 3225 and, instead, just utilize the annular cells 3220 between each of the leaflet posts 3230.

Figure 32B:
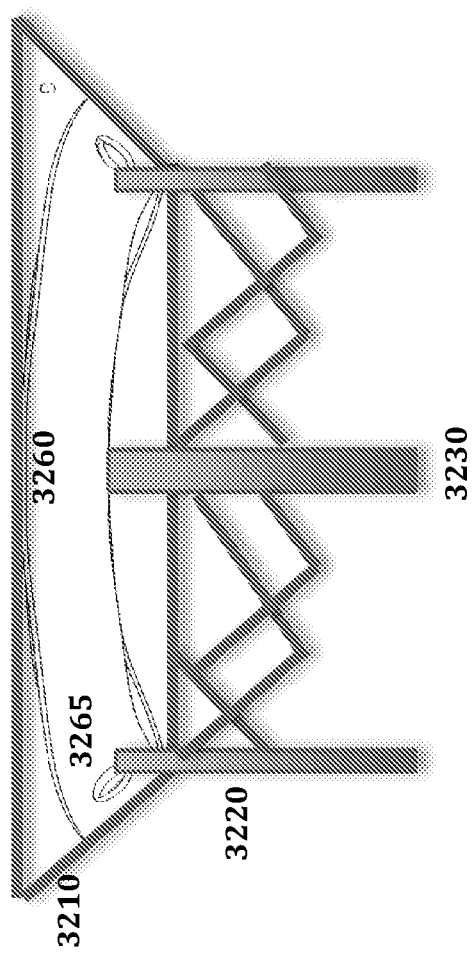
FIG. 32B is an illustration of the prosthetic valve, in accordance with an example embodiment of the present invention.

FIG. 32B illustrates the prosthetic valve. Prosthetic valve 3205 includes the inflow cells 3210, the annular cells 3220, the leaflet posts 3230, ring 3260 and ring eyelets 3265. In an embodiment, ring 3260 is similar to ring 10. FIG. 32B shows valve 3205 and the frame 3200 after it is connected in a cylindrical manner. In an exemplary embodiment, the inflow cells 3210, after they are connected in a cylindrical manner, extend radially in a distal direction. Further, in an embodiment, each of the leaflet posts 3230 is configured to fit the eyelets 3265 of the ring 3260.

Figure 32C:
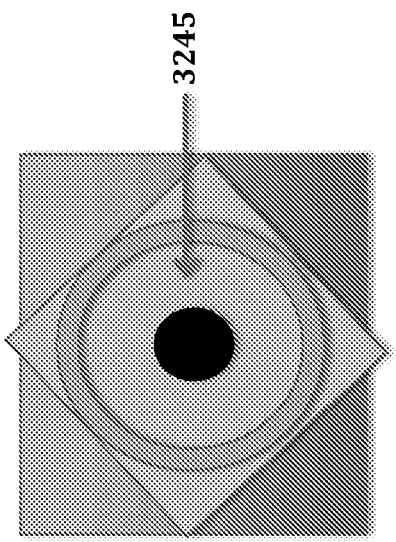
FIG. 32C is an illustration of an anchor receptacle at the prosthetic valve, in accordance with an example embodiment of the present invention.

FIG. 32C illustrates an anchor receptacle at the prosthetic valve. As depicted in FIG. 32C, each of the anchor receptacles 3240 includes an anchor target 3245 to receive a anchor. In an example embodiment, to affix the prosthetic valve to the surrounding tissue, the anchor receptacles 3240 could be placed on the ring of the prosthetic valve (e.g., ring 3260 of FIG. 32B). Thus, anchors may be driven through the ring 3260, and into surrounding tissue of the implant site, fixing or fastening the ring 3260 to the tissue of the implant site. In another example embodiment, the anchor receptacles 3240 are placed between the inflow cells 3210 and the leaflet posts 3230 of frame 3200 of FIG. 32A.

Inflow cells 3210 may be made softer and more malleable than annular cells 3220 or leaflet posts 3230, for example, by varying the wall thickness of the unibody from which the valve frame is cut. Once formed to the tubular valve shape, the inflow cells 3210, of a thinner wall thickness, remain soft and malleable to the surrounding native tissue of the heart valve. This allows the inflow cells 3210 to form more precisely to, and take the shape of, the native tissue, which allows for a tighter seal of the inflow track and better tissue in-growth into the prosthesis. On the other hand, the frame may transition from the thinner inflow cells to the thicker annular cells 3220, which are more rigid than the inflow cells 3210, and then further transition to the thicker and more rigid leaflet posts 3230. As the outflow side of the valve experiences more of valve fatigue, the increased rigidity of the annular cells 3220 and leaflet posts 3230 provide more support to the native valve tissue. The active fixation systems (i.e., the anchor deployment) described herein allow for this valve structure having varying levels or rigidity.

Figure 33A:
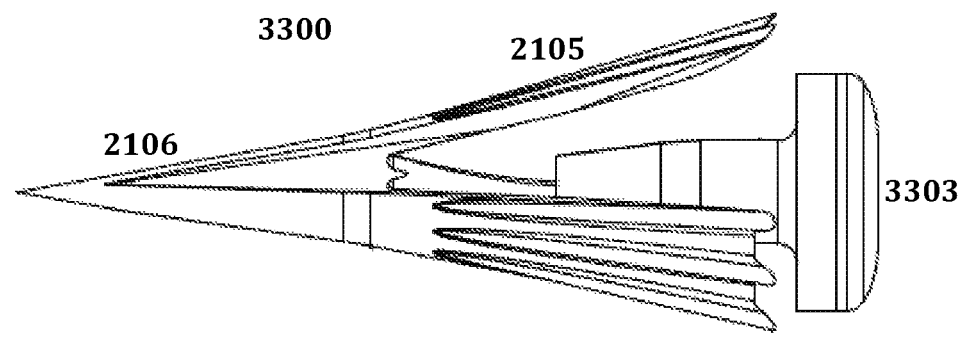
FIG. 33A is an illustration of a TCAT anchor, in accordance with an example embodiment of the present invention.
Figure 33B:
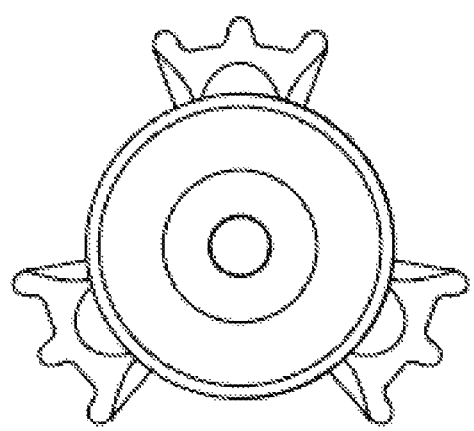
FIG. 33B is an axial view from the proximal end of the TCAT anchor of FIG. 33A.
Figure 33C:
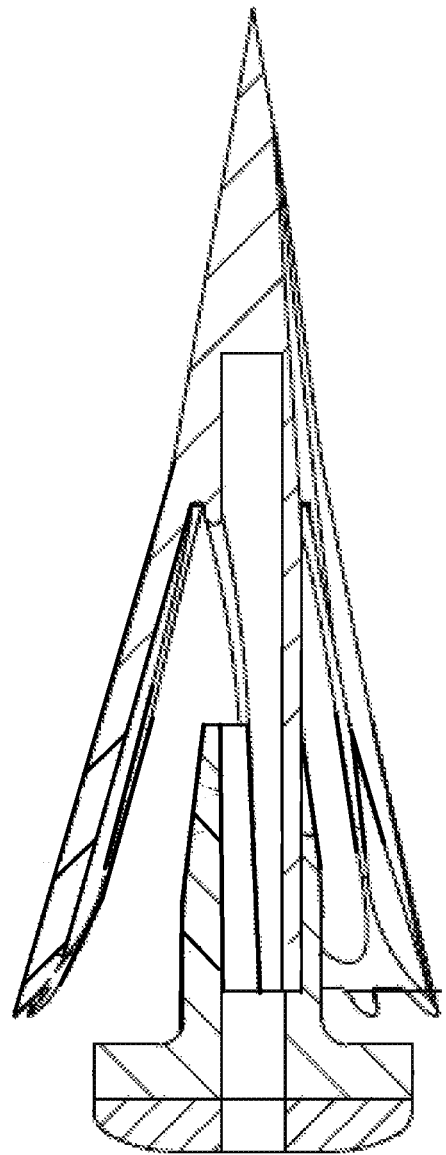
FIG. 33C is a cross-section view of the TCAT anchor of FIG. 33A.

FIGS. 33A to 33C illustrates anchor 3300 including an anchor head 2106, with barbs 2105, and an anchor cap 3303. In an example embodiment, anchor cap 3303 is overmolded over the proximal end of anchor head 2106. In an example embodiment, anchor cap 3303 may be made from thermoplastic urethane, silicon, or other elastomer material with tensioning properties, and may further include a non-deformable proximal end. The non-deformable prosthetic end is used to allow the tensioning component to apply force against the proximal end when the proximal end is brought into apposition with, e.g., a prosthetic valve device, to bring the prosthetic valve device into apposition with tissue. Accordingly, the anchor cap 3303 exerts a pulling force against the anchor head component in a proximal direction after deployment, allowing the barbs to set more securely and the prosthesis to remain in more constant contact with the tissue, despite the fluctuation of the tissue throughout the cardiac cycle.

In an exemplary embodiment, anchor head 2106 (i.e., the distal end of the anchor) of anchors 2101, 2310, 2620 and 3300 is tapered to a distal tip configured to pierce tissue. Further, barb(s) 2105 of anchors 2101, 2310, 2620 and 3300 extends proximally and radially outward from a distal end to a free end. Further, anchor cap swivels 2103 (of anchors 2101 and 2620) and 2313 (of anchor 2310) as well as anchor caps 2102 (of anchors 2101), 2312 (of anchor 2310) and 3303 (of anchor 3300) all include a width that is greater than the width of an anchor receptacle (i.e., 3240 of FIGS. 32A and 32C). Thus, the proximal end of the anchor (i.e., 2102, 2103, 2312, 2313 and/or 3303) may fit securely within the anchor receptacle at any number of various angles of deployment.

FIGS. 34A to 34E illustrate a prosthetic valve delivery system. Prosthetic deployment mechanism 3400 includes a handle 3401, retractable sheath 3402 and valve 3403. The valve 3403 of the present invention may be delivered to an implant site by first collapsing the valve 3403 into a collapsed or folded position, such that the prosthesis fits within a cavity of a catheter (e.g., within retractable sheath 3402). In an embodiment, in a first mode, the collapsed valve 3403 remains covered within the retractable sheath 3402. In a second mode, the retractable sheath 3402 retracts towards a proximal end and exposes the collapsed valve 3403. Once exposed, the collapsed valve 3403 may elastically return to an un-collapsed or expanded state.

Figure 34A:
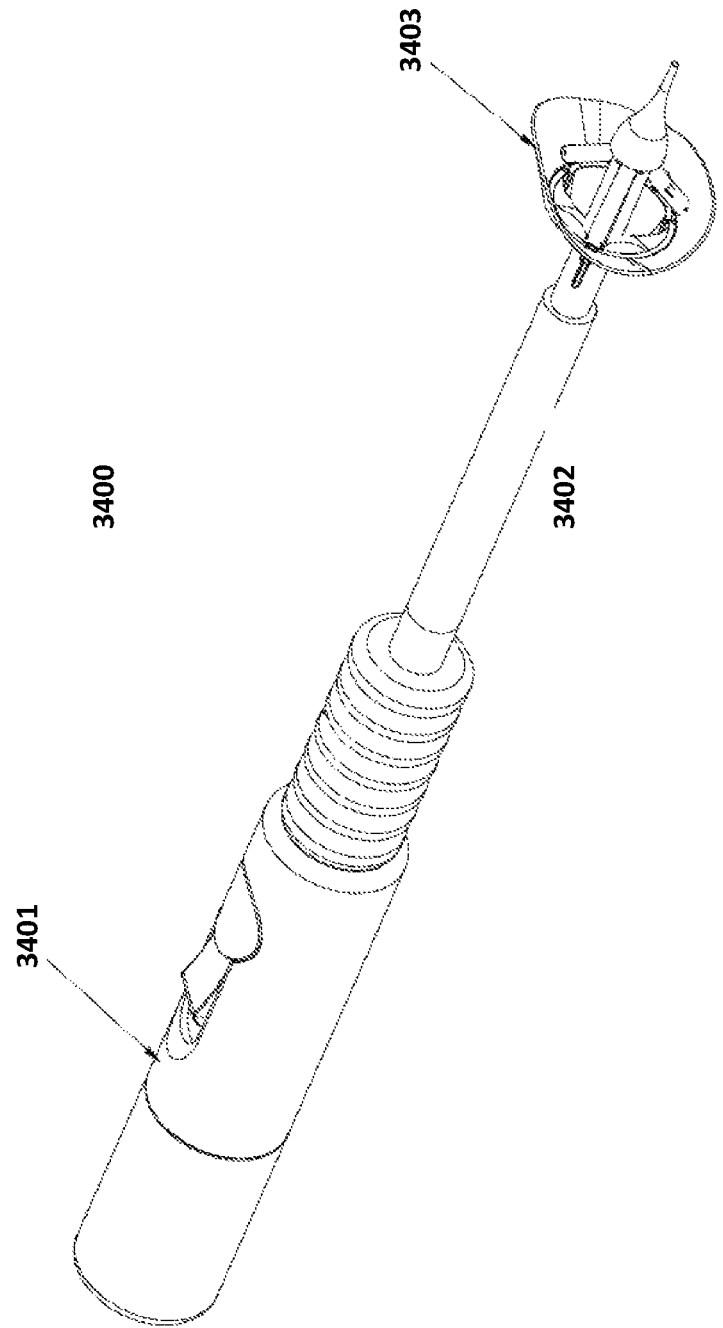
FIG. 34A is an illustration of a prosthetic valve delivery system, in accordance with an example embodiment of the present invention.
Figure 34B:
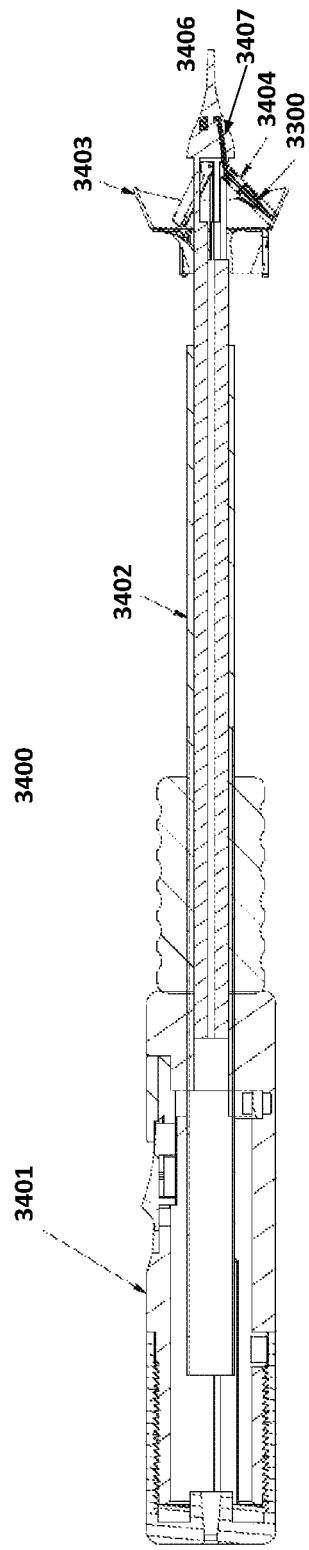
FIG. 34B is an illustration of the prosthetic valve delivery system of FIG. 34A prior to anchor deployment.
Figure 34C:
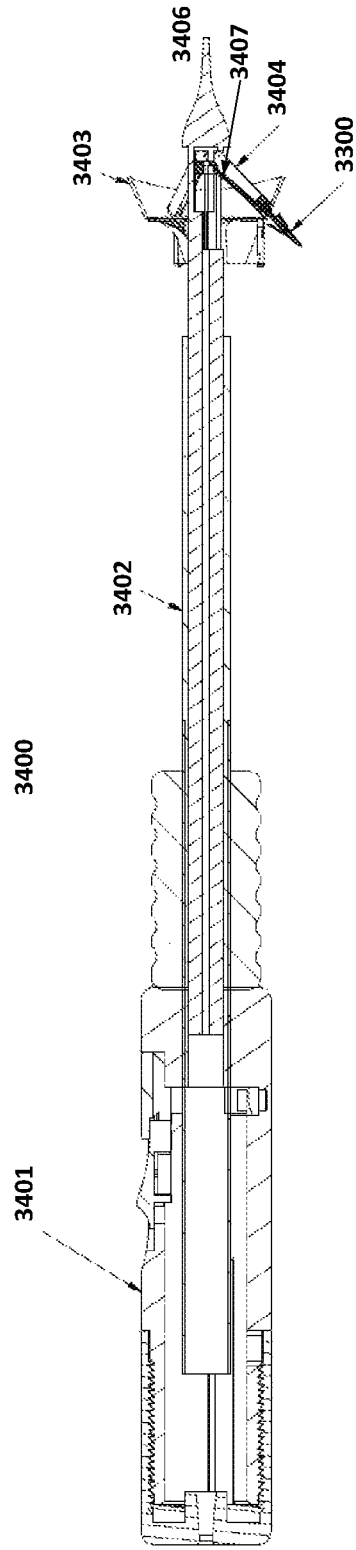
FIG. 34C is an illustration of the prosthetic valve delivery system of FIG. 34A after anchor deployment.
Figure 34D:
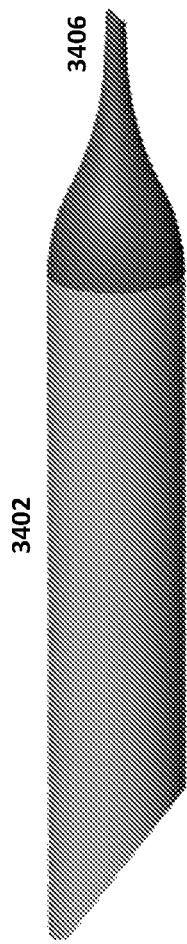
FIG. 34D is an illustration of the prosthetic valve delivery system of FIG. 34A prior to retracting the retractable sheath.
Figure 34E:
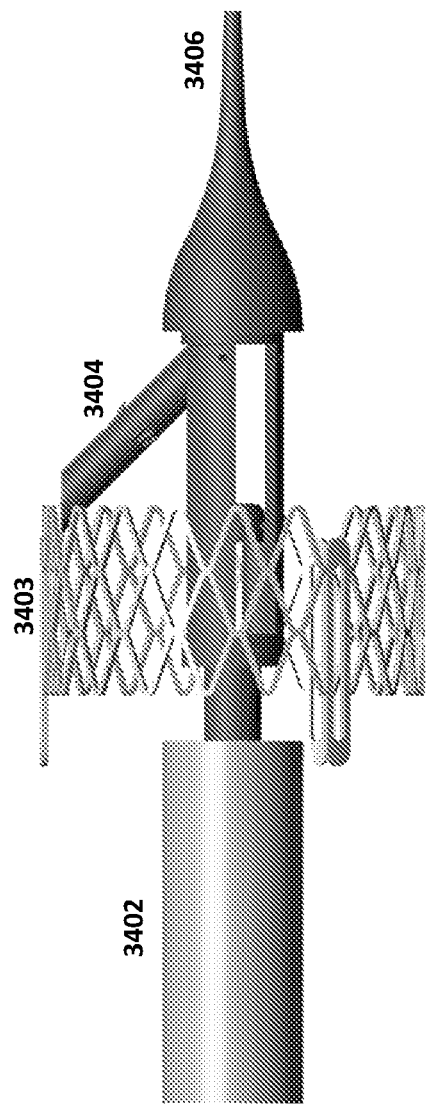
FIG. 34E is an illustration of the prosthetic valve delivery system of FIG. 34A after the retractable sheath is retracted.

FIG. 34B illustrates the prosthetic valve delivery system of FIG. 34A prior to anchor deployment. As depicted in FIG. 34B, prosthetic deployment mechanism 3400 further includes deployment arms 3404 (i.e., firing arms), anchors 3300 and distal tip 3406. A force delivery system may be used to fire the anchors. The force delivery system may use any mechanisms of nearly instantaneous force transfer, such as springs, gas, compressed fluid, or the like. Force is transferred through the shaft of a driver, which may be a rigid shaft or a flexible shaft, depending on the application. The force is used to displace a firing mechanism at the distal end of the shaft, which in turn exerts a driving force on the anchors to drive the anchors from the deployment arms and into the valve 3403 and the surrounding tissue. This driving force may be transferred by pin 3407, exerting a force on the proximal end of the anchor 3300. The driving force may result from a pushing force delivery system, which directs force in the distal direction of the driver, or a pulling force delivery system, which directs force in the proximal direction of the driver, depending on the application. In an exemplary embodiment, the prosthetic valve delivery system 3400 utilizes a pulling force delivery system in order to fire the anchors 3300 into the prosthetic valve 3403. In an example embodiment, anchors 3300 may be fired by deployment arms 3404 at the same time. In another example embodiment, anchors 3300 are fired at different times. In an example embodiment, the deployment arms 3404 are in a retracted position (i.e., parallel to the retractable sheath 3402) when covered by the retractable sheath 3402 and maneuver into a firing position after the prosthetic valve 3403 returns to the expanded state. In other words, the deployment arms 3404 are configured to rotate from a position aligned with the axis defined by the retractable sheath 3402 to a position directed radially away from the retractable sheath 3402, so that the deployment arms are directed towards the anchor receptacles of the valve 3404. In an example embodiment, after the anchors 3300 have been deployed, the deployment arms 3404 return to their position aligned with the retractable sheath 3402 and pass through the valve 3403 (along with the distal tip 3406) toward the direction of the handle 3401. As such, at some point after the distal tip 3406 passes through the valve 3403, the retractable sheath 3402 extends back to its original state and, thus, covers the retracted the deployment arms 3404.

Figure 35:
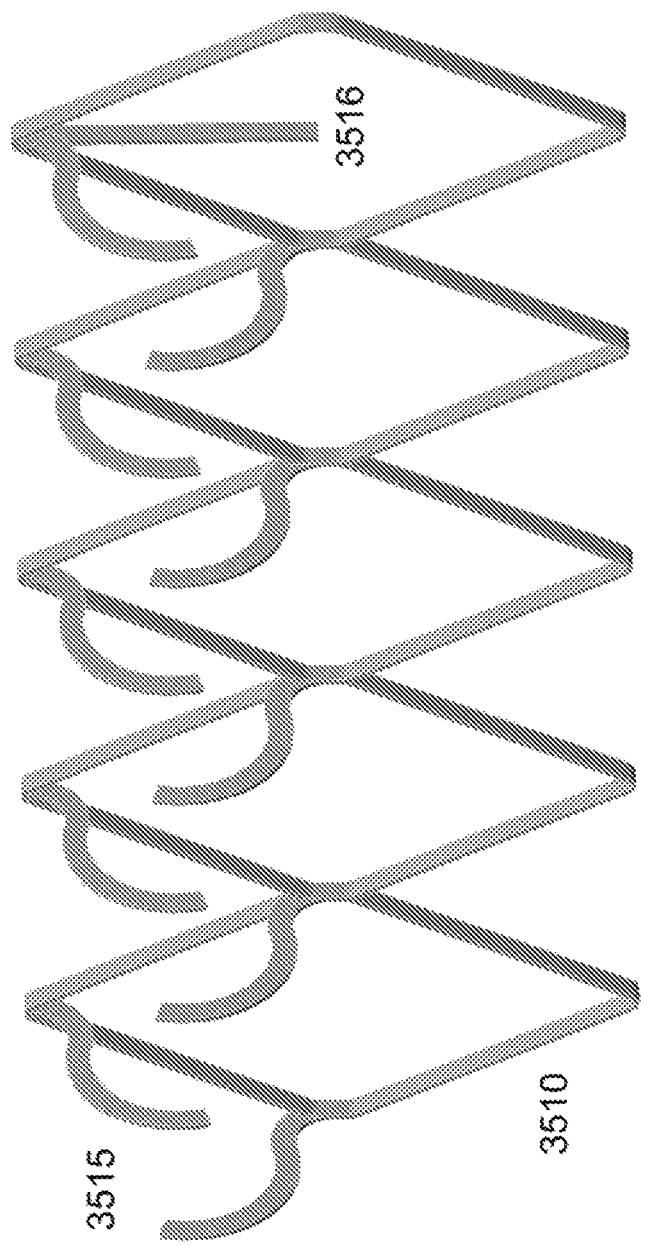
FIG. 35 is an illustration of a frame for a prosthetic valve, in accordance with an example embodiment of the present invention.

While valves used in open surgery generally include such a ring or collar, such a collar has not previously been achievable in retractable and deployable valves used in transcatheter mitral valve repair and transcatheter aortic valve repair. FIG. 35 illustrates another example embodiment of the valve frame. Inflow cells 3510 include ring struts 3515, which extend radially away from the valve body. In the retracted or collapsed state of the valve, ring struts 3515 are flush with the valve body. When the valve is deployed, however, the ring struts expand, in an alternating pattern distally and proximally, as illustrated. Ring struts may be made of spring-loaded steel or shape-memory alloys, such as nitinol. In the deployed state, the ring struts form a ring or collar around the inflow track of the valve body, helping to exert a sealing pressure on the surrounding tissue, and allowing for better in-growth of tissue to the valve. An example of the ring strut 3516 in the straight, flat, retracted position is also illustrated in FIG. 35.

In an embodiment, any of anchors 50, 200, 2101, 2310, 2620, 3300 and 4200 could be utilized with any of deployment mechanisms 100, 2800, 2900, 3000, 3100 and 3400 of the present invention. In another exemplary embodiment, after the distal end of any of anchors 2101, 2310, 2620 and 3300 is driven through the corresponding anchor receptacle into the surrounding tissue, the proximal end of the respective anchor is configured to be brought into apposition with the corresponding anchor receptacle, such that the proximal end exerts a pulling force on the distal end of the anchor.

Further, any of the implantable elements described herein, e.g., anchors 50, 200, 2101, 2310, 2620, 3300 and 4200, rings 10 and 3265, leaflets 30, valve struts 31 or leaflet posts 3230, or any other element of heart valve replacement prosthesis 1 or prosthetic valves 3205 and 3403, may be formed wholly or partly of a material absorbable into the patient's body, or of a nonabsorbable material, depending on, e.g., the specific application. For example, these elements may be formed of polyglycolic acid (PGA), or a PGA copolymer. These elements may also, or alternatively, be formed of copolymers of polyester and/or nylon and/or other polymer(s). Moreover, these elements may contain one or more shape-memory alloys, e.g., nitinol, spring-loaded steel or other alloy or material with appropriate properties.

Absorbable materials may be advantageous where there is a potential for misfiring or improper locating of the various implants. For example, in a situation where the driver drives an anchor 50, 200, 2101, 2310, 2620, 3300 and 4200 at an unintended location, or where the tissue does not properly receive the anchor 50, 200, 2101, 2310, 2620, 3300 and 4200, the anchor 50, 200, 2101, 2310, 2620, 3300 and 4200, even where not needed, would be relatively harmless, as it would eventually absorb into the patient's body.

Although the present invention has been described with reference to particular examples and exemplary embodiments, it should be understood that the foregoing description is in no manner limiting. Moreover, the features described herein may be used in any combination.

What is claimed is:

1. A surgical anchor, comprising:
   a distal end and a proximal end, wherein the distal end comprises an anchor head that is tapered to a distal tip configured to pierce and anchor into tissue;
   an anchor cap swivel provided at the proximal end; and
   a coil spring connecting the anchor head and the anchor cap swivel;
   wherein the coil spring is configured to exert a force on the anchor head when the anchor head is anchored into the tissue.

2. The surgical anchor of claim 1, wherein the anchor resists proximal movement when engaged with the tissue.

3. The surgical anchor of claim 1, wherein the coil spring exerts the force on the anchor cap swivel when the anchor is deployed in the tissue, urging the anchor cap swivel of the anchor in a distal direction.

4. The surgical anchor of claim 1, wherein the anchor cap swivel includes a non-deforming material.

5. The surgical anchor of claim 1, wherein the surgical anchor is configured to be received by one of a plurality of anchor receptacles of a prosthetic valve,
   wherein the prosthetic valve comprises:
   a plurality of inflow cells situated in the proximal direction of the prosthetic valve, wherein the inflow cells are malleable; and
   a plurality of annular cells situated medially in the prosthetic valve, forming a circular outflow track,
   wherein the annular cells are more rigid that the inflow cells; and a plurality of leaflet posts integral to, and extending distally beyond, the annular cells in the outflow direction of the prosthetic valve,
   wherein the leaflet posts are more rigid than the annular cells.

6. The surgical anchor of claim 1, further comprising a plurality of barbs extending proximally from the anchor head.

7. The surgical anchor of claim 1, wherein the anchor head comprises a threaded proximal portion and the anchor cap swivel comprises a threaded distal portion and the coil spring is connected to the threaded proximal portion of the anchor head and the threaded distal portion of the anchor cap swivel.

8. The surgical anchor of claim 1, wherein the anchor head, anchor cap swivel, and the coil spring each comprise a hollow lumen; and the anchor head, the coil spring, and the anchor cap swivel are arranged to align the hollow lumens for receiving a pusher wire of an anchor deployment device.

9. A surgical device, comprising:
   an anchor, wherein the anchor includes:
   a distal end and a proximal end, wherein the distal end comprises an anchor head that is tapered to a distal tip configured to pierce and anchor into tissue;
   a an anchor cap swivel provided at the proximal end that has a width greater than a width of a corresponding anchor receptacle of a prosthetic valve; and
   a coil spring connected with the anchor head and the anchor cap swivel;
   wherein the distal end of the anchor is configured to be driven by a deployment device through the corresponding anchor receptacle of the prosthetic valve into the tissue adjacent to the prosthetic valve, and further wherein a proximal end of the proximal head of the deployed anchor is configured to be brought into apposition with the corresponding anchor receptacle, such that, after deployment of the anchor into the tissue, the coil spring is in a tensioned state to exert a pulling force on the anchor head of the anchor so that the anchor head acting on the anchor receptacle of the prosthetic valve will approximate the prosthetic valve with the tissue.

10. The surgical device of claim 9, wherein the prosthetic valve comprises:
   a plurality of inflow cells situated in the proximal direction of the prosthetic valve, wherein the inflow cells are malleable; and
   a plurality of annular cells situated medially in the prosthetic valve, forming a circular outflow track, wherein the annular cells are more rigid than the inflow cells; and
   a plurality of leaflet posts integral to, and extending distally beyond, the annular cells in the outflow direction of the prosthetic valve, wherein the leaflet posts are more rigid than the annular cells.

11. A surgical anchor, comprising:
   a distal end and a proximal end, wherein the distal end comprises an anchor head that is tapered to a distal tip configured to pierce and anchor into tissue;
   a plurality of barbs extending proximally from the anchor head;
   an anchor cap swivel provided at the proximal end; and
   a tension spring connecting the anchor head and the anchor cap swivel;
   wherein the tension spring is configured to exert a force on the anchor head when the anchor head is anchored into the tissue.

12. The surgical anchor of claim 11, wherein the barbs resist proximal movement of the surgical anchor when the surgical anchor is engaged with the tissue.

13. The surgical anchor of claim 11, wherein the tension spring exerts the force on the anchor cap swivel when the surgical anchor is deployed in the tissue, urging the anchor cap swivel in a distal direction.

* * * * *